US011458325B2

(12) United States Patent
Simon et al.

(10) Patent No.: US 11,458,325 B2
(45) Date of Patent: *Oct. 4, 2022

(54) NON-INVASIVE NERVE STIMULATION TO PATIENTS

(71) Applicant: ElectroCore, Inc., Basking Ridge, NJ (US)

(72) Inventors: Bruce J. Simon, Mountain Lakes, NJ (US); Joseph P. Errico, Warren, NJ (US); John T. Raffle, Austin, TX (US); Steven Mendez, Chester, NJ (US)

(73) Assignee: ELECTROCORE, INC, Rockaway, NJ (US)

( * ) Notice: Subject to any disclaimer, the term of this patent is extended or adjusted under 35 U.S.C. 154(b) by 196 days.

This patent is subject to a terminal disclaimer.

(21) Appl. No.: 16/830,607

(22) Filed: Mar. 26, 2020

(65) Prior Publication Data

US 2020/0222708 A1 Jul. 16, 2020

Related U.S. Application Data

(60) Continuation of application No. 16/030,368, filed on Jul. 9, 2018, now Pat. No. 10,639,490, which is a
(Continued)

(51) Int. Cl.
*A61N 1/36* (2006.01)
*A61N 1/378* (2006.01)
(Continued)

(52) U.S. Cl.
CPC .............. *A61N 2/002* (2013.01); *A61H 23/00* (2013.01); *A61H 23/02* (2013.01); *A61H 31/00* (2013.01);
(Continued)

(58) Field of Classification Search
None
See application file for complete search history.

(56) References Cited

U.S. PATENT DOCUMENTS 3,590,810 A 7/1971 Kopecky
4,196,737 A 4/1980 Bevilacqua
(Continued)

FOREIGN PATENT DOCUMENTS

EP 1967226 10/2008
EP 2777764 8/2015
(Continued)

OTHER PUBLICATIONS

Europe Office Action dated Jul. 26, 2018 in related Application No. 11818591.7 filed Aug. 12, 2011 (8 pages).
(Continued)

*Primary Examiner* — Brian T Gedeon
(74) *Attorney, Agent, or Firm* — Farber LLC

(57) ABSTRACT

Devices, systems and methods are provided for treating a disease or disorder in a patient. The methods include positioning a surface of a housing in contact with an outer skin surface of the patient and applying sufficient energy to an energy transmitter within the housing via a power supply to generate an electrical impulse at or near a vagus nerve of the patient. The electrical impulse is sufficient to modulate fibers of the vagus nerve and treat the disease or disorder.

20 Claims, 17 Drawing Sheets

Related U.S. Application Data continuation of application No. 15/419,058, filed on Jan. 30, 2017, now Pat. No. 10,016,615, which is a continuation of application No. 15/145,767, filed on May 30, 2016, now Pat. No. 9,555,260, which is a continuation of application No. 14/337,612, filed on Jul. 22, 2014, now Pat. No. 9,327,118, which is a division of application No. 12/859,568, filed on Aug. 19, 2010, now Pat. No. 9,037,247.

(51) Int. Cl.

| | | |
|---|---|---|
| *A61N 1/375* | (2006.01) | |
| *A61N 2/00* | (2006.01) | |
| *A61N 1/40* | (2006.01) | |
| *A61H 23/00* | (2006.01) | |
| *A61H 23/02* | (2006.01) | |
| *A61H 31/00* | (2006.01) | |
| *A61H 39/00* | (2006.01) | |
| *A61N 2/02* | (2006.01) | |
| *A61N 5/06* | (2006.01) | |
| *A61N 7/00* | (2006.01) | |

(52) U.S. Cl.
CPC ......... *A61H 39/002* (2013.01); *A61N 1/3601* (2013.01); *A61N 1/36014* (2013.01); *A61N 1/3758* (2013.01); *A61N 1/3787* (2013.01); *A61N 1/40* (2013.01); *A61N 2/006* (2013.01); *A61N 2/02* (2013.01); *A61N 5/0603* (2013.01); *A61N 5/0622* (2013.01); *A61N 5/0625* (2013.01); *A61N 7/00* (2013.01); *A61H 23/004* (2013.01); *A61H 23/0236* (2013.01); *A61H 2201/123* (2013.01); *A61H 2201/1604* (2013.01); *A61H 2201/165* (2013.01); *A61H 2201/1609* (2013.01); *A61N 1/36114* (2013.01); *A61N 2005/063* (2013.01); *A61N 2005/0605* (2013.01); *A61N 2007/0026* (2013.01)

(56) References Cited

U.S. PATENT DOCUMENTS

| | | | |
|---|---|---|---|
| 4,989,605 A | 2/1991 | Rossen | |
| 5,109,847 A | 5/1992 | Liss et al. | |
| 5,458,141 A | 10/1995 | Neil | |
| 5,487,759 A | 1/1996 | Bastyr et al. | |
| 5,782,874 A | 7/1998 | Loos | |
| 5,899,922 A | 5/1999 | Loos | |
| 5,983,131 A | 11/1999 | Weaver et al. | |
| 6,341,236 B1 | 1/2002 | Osorio et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 6,631,297 B1 | 10/2003 | Mo | |
| 7,254,444 B2 | 8/2007 | Moore | |
| 7,294,101 B2* | 11/2007 | Fischell | A61N 2/02 600/13 |
| 7,734,340 B2 | 6/2010 | De Ridder | |
| 7,797,041 B2 | 9/2010 | Libbus et al. | |
| 8,676,324 B2* | 3/2014 | Simon | A61N 1/40 607/42 |
| 8,676,330 B2* | 3/2014 | Simon | A61N 1/36021 607/46 |
| 9,037,247 B2* | 5/2015 | Simon | A61N 2/02 607/42 |
| 9,119,953 B2* | 9/2015 | Simon | A61N 5/0622 |
| 9,358,281 B2* | 6/2016 | Littman | C07K 14/005 |
| 10,639,490 B2* | 5/2020 | Simon | A61N 5/0622 |
| 2002/0099417 A1 | 7/2002 | Naritoku et al. | |
| 2002/0183237 A1 | 12/2002 | Puskas | |
| 2002/0183804 A1 | 12/2002 | Malaney et al. | |
| 2003/0212311 A1 | 11/2003 | Nova et al. | |
| 2004/0073271 A1 | 4/2004 | Harry et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 | 5/2005 | Fox et al. | |
| 2005/0137644 A1 | 6/2005 | Boveja et al. | |
| 2005/0165458 A1 | 7/2005 | Boveja | |
| 2005/0187590 A1 | 8/2005 | Boveja et al. | |
| 2005/0216062 A1 | 9/2005 | Herbst | |
| 2005/0267544 A1 | 12/2005 | Lee et al. | |
| 2006/0074284 A1 | 4/2006 | Juola et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1* | 2/2007 | Parnis | A61N 1/3601 607/42 |
| 2007/0038264 A1 | 2/2007 | Jaax et al. | |
| 2007/0106337 A1 | 5/2007 | Errico et al. | |
| 2007/0123952 A1* | 5/2007 | Strother | A61N 1/0456 607/48 |
| 2007/0142886 A1 | 6/2007 | Fischell et al. | |
| 2007/0150006 A1 | 6/2007 | Libbus et al. | |
| 2007/0156182 A1 | 7/2007 | Castel et al. | |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0077192 A1 | 3/2008 | Harry et al. | |
| 2008/0114199 A1 | 5/2008 | Riehl et al. | |
| 2008/0132964 A1 | 6/2008 | Cohen et al. | |
| 2008/0177190 A1 | 7/2008 | Libbus et al. | |
| 2008/0208266 A1 | 8/2008 | Lesser et al. | |
| 2008/0306325 A1 | 12/2008 | Burnett et al. | |
| 2009/0036945 A1 | 2/2009 | Chancellor | |
| 2009/0099622 A1 | 4/2009 | Fowler | |
| 2009/0112283 A1 | 4/2009 | Kriksunov et al. | |
| 2009/0132018 A1 | 5/2009 | DiUbaldi et al. | |
| 2009/0157149 A1 | 6/2009 | Wahlgren et al. | |
| 2009/0234417 A1 | 9/2009 | Pastena et al. | |
| 2009/0234419 A1 | 9/2009 | Maschino et al. | |
| 2009/0240297 A1 | 9/2009 | Shavit et al. | |
| 2009/0287035 A1 | 11/2009 | Dietrich et al. | |
| 2010/0030299 A1 | 2/2010 | Covalin | |
| 2010/0152794 A1 | 6/2010 | Radivojevic et al. | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0060304 A1 | 3/2013 | LaTendresse et al. | |
| 2013/0245486 A1 | 9/2013 | Simon et al. | |
| 2014/0005743 A1 | 1/2014 | Giuffrida et al. | |
| 2014/0172041 A1 | 6/2014 | Draghici | |
| 2014/0222102 A1 | 8/2014 | Lemus | |
| 2014/0236040 A1 | 8/2014 | Moon | |
| 2014/0031895 A1 | 10/2014 | Rahimi | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| JP | 2006-515192 | 11/2006 |
| JP | 2009-125263 | 6/2009 |
| JP | 2012-52385 | 9/2013 |
| JP | 2014-510586 | 5/2014 |
| KR | 10-1242190 | 3/2013 |
| KR | 101242190 | 3/2013 |
| WO | WO1993/01862 | 2/1993 |
| WO | WO2008/042902 | 4/2003 |
| WO | WO2005/007120 | 1/2005 |
| WO | WO2007/092062 | 8/2007 |

(56) References Cited

FOREIGN PATENT DOCUMENTS

| WO | WO2007/058780 | 5/2008 |
| --- | --- | --- |
| WO | WO2009/021080 | 2/2009 |
| WO | WO2009/064641 | 5/2009 |
| WO | WO2009/135693 | 11/2009 |
| WO | WO 2012/174330 | 12/2012 |
| WO | WO2013066135 | 5/2013 |

OTHER PUBLICATIONS

Europe Office Action dated Apr. 24, 2018 in related Application No. 15796247.3 filed May 20, 2015 (6 pages).

Greicius et al., Functional connectivity in the resting brain: A network analysis of the default mode hypothesis, PNAS, Jan. 2003, vol. 100, No. 1, pp. 253-258.

Heneka et al., Locus ceruleus controls Alzheimer's disease pathology by modulating microglial functions through norepinephrine, PNAS, Mar. 2010, vol. 107, No. 13, pp. 6058-6063.

International Search Report and Written Opinion dated Jan. 29, 2014 in related PCT Application No. PCT/US2013/068804 filed Nov. 6, 2013 (10 pages).

International Search Report and Written Opinion dated Mar. 26, 2008 in related PCT Application No. PCT/US2006/042752 filed Nov. 1, 2006 (7 pages).

International Search Report and Written Opinion dated Apr. 30, 2013 in related PCT Application No. PCT/US2013/023014 filed Jan. 24, 2013 (7 pages).

International Search Report and Written Opinion dated May 8, 2007 in related PCT Application No. PCT/US2006/042823 filed Nov. 2, 2006 (5 pages).

International Search Report and Written Opinion dated Aug. 25, 2015 in related Application No. PCT/US15/31847 filed May 20, 2015 (10 pages).

International Search Report and Written Opinion dated Sep. 17, 2007 in related PCT Application No. PCT/US2006/042828 filed Nov. 2, 2006 (5 pages).

International Search Report and Written Opinion dated Dec. 11, 2013 in related PCT Application No. PCT/US2013/058079 filed Sep. 4, 2013 (8 pages).

International Search Report and Written Opinion dated Dec. 22, 2011 in related PCT Application No. PCT/US2011/049844 filed Aug. 31, 2011 (9 pages).

KR101242190 dated Mar. 25, 2013, Espacenet computer generated English translation (11 pages).

Lee et al., Clustering of Resting State Networks, PLoS One, Jul. 2012, vol. 7, Issue 7, pp. 1-12.

\* cited by examiner

FIG. 18

| Patient ID | Initial FEV1 % Predicted | Historical FEV1 % Predicted | Peak % Increase FEV1 from initial | Elapsed Time (min) to Peak FEV1 increase | Elapsed Time until 12% FEV1 increase |
|---|---|---|---|---|---|
| 03-001 | 61 | | 43.9 | 75 | 15 |
| 01-001 | 51 | | 41.2 | 150 | 30 |
| 04-001* | 16 | | 131.3 | 150 | 15 |
| 01-002 | 66 | | 19.7 | 90 | 90 |
| 04-002** | 52 | | 19.2 | 15 | 15 |
| *Average* | 49.2 | | 51.1 | 96.0 | 33.0 |

Data minus patient 04-001 and 04-002

| Patient ID | Initial FEV1 % Predicted | Historical FEV1 % Predicted | Peak % Increase FEV1 from initial | Elapsed Time (min) to Peak FEV1 increase | Elapsed Time until 12% FEV1 increase |
|---|---|---|---|---|---|
| 03-001 | 61 | | 43.9 | 75 | 15 |
| 01-001 | 51 | | 41.2 | 150 | 30 |
| 01-002 | 66 | | 19.7 | 90 | 90 |
| *Average* | 59.3 | | 34.9 | 105.0 | 45.0 |

NON-INVASIVE NERVE STIMULATION TO PATIENTS

CROSS REFERENCE TO RELATED APPLICATIONS

This application is a Continuation of U.S. Nonprovisional application Ser. No. 16/030,368, filed Jul. 9, 2018, which is a continuation of U.S. Nonprovisional application Ser. No. 15/419,058 filed 30 Jan. 2017, now U.S. Pat. No. 10,016,615, issued Jul. 10, 2018; which is a Continuation of U.S. Nonprovisional application Ser. No. 15/145,767 filed 3 May 2016, now U.S. Pat. No. 9,555,260 issued 31 Jan. 2017; which is a Continuation of U.S. Nonprovisional application Ser. No. 14/337,612 filed 22 Jul. 2014, now U.S. Pat. No. 9,327,118 issued 3 May 2016; which is a Divisional of U.S. Nonprovisional application Ser. No. 12/859,568, filed 19 Aug. 2010, now U.S. Pat. No. 9,037,247 issued 19 May 2015, each of which is herein fully incorporated by reference for all purposes.

BACKGROUND OF THE INVENTION

The field of the present invention relates to the delivery of energy impulses (and/or fields) to bodily tissues for therapeutic purposes, and more specifically to non-invasive devices and methods for treating conditions associated with bronchial constriction. The energy impulses (and/or fields) comprise electrical and/or magnetic, mechanical and/or acoustic, and optical and/or thermal energy.

There are a number of treatments for various infirmities that require the destruction of otherwise healthy tissue in order to affect a beneficial effect. Malfunctioning tissue is identified, and then lesioned or otherwise compromised in order to affect a beneficial outcome, rather than attempting to repair the tissue to its normal functionality. While there are a variety of different techniques and mechanisms that have been designed to focus lesioning directly onto the target nerve tissue, collateral damage is usually inevitable.

Still other treatments for malfunctioning tissue can be medicinal in nature, in many cases leaving patients to become dependent upon artificially synthesized chemicals. Examples of this are anti-asthma drugs such as albuterol, proton pump inhibitors such as omeprazole (Prilosec), spastic bladder relievers such as Ditropan, and cholesterol reducing drugs like Lipitor and Zocor. In many cases, these medicinal approaches have side effects that are either unknown or quite significant. For example, at least one popular diet pill of the late 1990's was subsequently found to cause heart attacks and strokes. Unfortunately, the beneficial outcomes of surgery and medicines are, therefore, often realized at the cost of function of other tissues, or risks of side effects.

The use of electrical stimulation for treatment of medical conditions has been well known in the art for nearly two thousand years. It has been recognized that electrical stimulation of the brain and/or the peripheral nervous system and/or direct stimulation of the malfunctioning tissue, which stimulation is generally a wholly reversible and non-destructive treatment, holds significant promise for the treatment of many ailments.

Electrical stimulation of the brain with implanted electrodes has been approved for use in the treatment of various conditions, including pain and movement disorders including essential tremor and Parkinson's disease. The principle behind these approaches involves disruption and modulation of hyperactive neuronal circuit transmission at specific sites in the brain. As compared with the very dangerous lesioning procedures in which the portions of the brain that are behaving pathologically are physically destroyed, electrical stimulation is achieved by implanting electrodes at these sites to, first sense aberrant electrical signals and then to send electrical pulses to locally disrupt the pathological neuronal transmission, driving it back into the normal range of activity. These electrical stimulation procedures, while invasive, are generally conducted with the patient conscious and a participant in the surgery.

Brain stimulation, and deep brain stimulation in particular, is not without some drawbacks. The procedure usually requires penetrating the skull, and inserting an electrode into the brain matter using a catheter-shaped lead, or the like. While monitoring the patient's condition (such as tremor activity, etc.), the position of the electrode is adjusted to achieve significant therapeutic potential. Next, adjustments are made to the electrical stimulus signals, such as frequency, periodicity, voltage, current, etc., again to achieve therapeutic results. The electrode is then permanently implanted and wires are directed from the electrode to the site of a surgically implanted pacemaker. The pacemaker provides the electrical stimulus signals to the electrode to maintain the therapeutic effect. While the therapeutic results of deep brain stimulation are promising, there are significant complications that arise from the implantation procedure, including stroke induced by damage to surrounding tissues and the neurovasculature.

One of the most successful modern applications of this basic understanding of the relationship between muscle and nerves is the cardiac pacemaker. Although its roots extend back into the 1800's, it was not until 1950 that the first practical, albeit external and bulky pacemaker was developed. Dr. Rune Elqvist developed the first truly functional, wearable pacemaker in 1957. Shortly thereafter, in 1960, the first fully implanted pacemaker was developed.

Around this time, it was also found that the electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to Deno, et al., the disclosure of which is incorporated herein by reference).

Another application of electrical stimulation of nerves has been the treatment of radiating pain in the lower extremities by means of stimulation of the sacral nerve roots at the bottom of the spinal cord (see U.S. Pat. No. 6,871,099 to Whitehurst, et al., the disclosure of which is incorporated herein by reference).

Nerve stimulation is thought to be accomplished directly or indirectly by depolarizing a nerve membrane, causing the discharge of an action potential; or by hyperpolarization of a nerve membrane, preventing the discharge of an action potential. Such stimulation may occur after electrical energy, or also other forms of energy, are transmitted to the vicinity of a nerve [F. RATTAY. The basic mechanism for the electrical stimulation of the nervous system. Neuroscience Vol. 89, No. 2, pp. 335-346, 1999; Thomas HEIMBURG and Andrew D. Jackson. On soliton propagation in biomembranes and nerves. PNAS vol. 102 (no. 28, Jul. 12, 2005): 9790-9795]. Nerve stimulation may be measured directly as an increase, decrease, or modulation of the activity of nerve fibers, or it may be inferred from the physiological effects that follow the transmission of energy to the nerve fibers.

The present disclosure involves medical procedures that stimulate nerves by non-invasively transmitting different forms of energy to nerves. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that the invasive procedures insert a substance or device into or through the skin (or other surface of the body, such as a wound bed) or into an internal body cavity beyond a body orifice. The following paragraphs give examples of non-invasive medical procedures, contrasting some of them with corresponding invasive medical procedures.

For example, transcutaneous electrical stimulation of a nerve is non-invasive because it involves attaching electrodes to the surface of the skin (or using a form-fitting conductive garment) without breaking the skin. In contrast, percutaneous electrical stimulation of a nerve is minimally invasive because it involves the introduction of an electrode under the skin, via needle-puncture of the skin.

Another form of non-invasive electrical stimulation, known as magnetic stimulation, involves the generation (induction) of an eddy current within tissue, which results from an externally applied time-varying magnetic field. The principle of operation of magnetic stimulation, along with a list of medical applications of magnetic stimulation, is described in: Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006. As described in that Guide, applications of magnetic stimulation include the stimulation of selected peripheral nerves, as well as stimulation of selected portions of the brain (transcranial magnetic stimulation). Mechanisms underlying biological effects that result from applying such time-varying magnetic fields are reviewed in: PILLA, A. A. Mechanisms and therapeutic applications of time varying and static magnetic fields. In Barnes F and Greenebaum B (eds), Biological and Medical Aspects of Electromagnetic Fields. Boca Raton Fla.: CRC Press, 351-411 (2006).

Diathermy includes non-invasive methods for the heating of tissue, in which the temperature of tissues is raised by high frequency current, ultrasonic waves, or microwave radiation originating outside the body. With shortwave, microwave and radiofrequency diathermy, the tissue to be treated is irradiated with electromagnetic fields having a carrier frequency of typically 13.56, 27.12, 40.68, 915 or 2450 MHz, modulated at frequencies of typically 1 to 7000 Hz. The heating effects may be dielectric, wherein molecules in tissues try to align themselves with the rapidly changing electric field, and/or induced, wherein rapidly reversing magnetic fields induce circulating electric currents and electric fields in the body tissues, thereby generating heat. With ultrasound diathermy, high-frequency acoustic vibrations typically in the range of 800 to 1,000 KHz are used to generate heat in deep tissue.

Devices similar to those used with diathermy deliver electromagnetic waves non-invasively to the body for therapeutic purposes, without explicitly intending to heat tissue. For example, U.S. Pat. No. 4,621,642, entitled Microwave apparatus for physiotherapeutic treatment of human and animal bodies, to Chen, describes apparatus for performing acupuncture treatment with microwaves. U.S. Pat. No. 5,131,409, entitled Device for microwave resonance therapy, to Lobarev et al. discloses the transmission of an electromagnetic wave that is propagated along a slotted transmission line in free space toward the patient's skin, for applications analogous to laser acupuncture. U.S. Pat. No. 7,548,779, entitled Microwave energy head therapy, to Konchitsky, discloses the transmission of high frequency electromagnetic pulses non-invasively to a patient's head, for purposes of treating headaches, epilepsy, and depression, wherein the brain behaves as an antenna for receiving electromagnetic energy at certain wavelengths.

Acupuncture (meridian therapy) may be non-invasive if the acupuncture tool does not penetrate the skin, as practiced in Toyohari acupuncture and the pediatric acupuncture style Shonishin. Other forms of acupuncture may also be non-invasive when they use the Teishein, which is one of the acupuncture needles described in classical texts of acupuncture. Even though it is described as an acupuncture needle, the Teishein does not pierce or puncture the skin. It is used to apply rapid percussion pressure to the meridian point being treated, so its use may also be described as a form of acupressure. Electroacupuncture is often performed as a non-invasive transcutaneous form of electrostimulation. Laser acupuncture and colorpuncture are also non-invasive in that acupuncture meridian points are stimulated at the surface of the skin with light, rather than mechanically or electrically. Although it is possible to compare the effectiveness of acupuncture treatment with the effectiveness of Western types of treatments for recognized disorders such as asthma, it is always possible to ascribe any differences in effectiveness to differences in mechanisms. This is because acupuncture treats patients by stimulating acupuncture meridian points, not tissue such as nerves or blood vessels as identified by modern western medicine. Furthermore, acupuncture endeavors to produce effects that are not contemplated by modern western medicine, such as the de qi sensation, and results using acupuncture may be confounded by the individualized selection of meridian points, as well as by the simultaneous treatment with herbal medicines. For example, acupuncture is not considered to be effective for the treatment of asthma [McCARNEY R W, Brinkhaus B, Lasserson T J, Linde K. Acupuncture for chronic asthma (Review). The Cochrane Library 2009, Issue 3. John Wiley & Sons, Ltd.; Michael Y. SHAPIRA, Neville Berkman, Gila Ben-David, Avraham Avital, Elat Bardach and Raphael Breuer. Short-term Acupuncture Therapy Is of No Benefit in Patients With Moderate Persistent Asthma. CHEST 2002; 121:1396-1400; W GRUBER, E Eber, D Malle-Scheid, A Pfleger, E Weinhandl, L Dorfer, M S Zach. Laser acupuncture in children and adolescents with exercise induced asthma. Thorax 2002; 57:222-225], but even if were to have been shown effective, such effectiveness would, by definition, be attributable only to the stimulation of meridian points, as interpreted in terms of theories related to oriental medicine (e.g., restoration of Qi balance in Traditional Chinese Medicine).

Other forms of non-invasive medical procedures direct mechanical vibrations to selected organs or are used to massage muscles. For example, mechanical vibrations applied to the chest are used by physiotherapists to dislodge mucus in the lungs. [M. J. GOODWIN. Mechanical chest stimulation as a physiotherapy aid. Med. Eng. Phys., 1994, Vol. 16, 267-272; Harriet SHANNON, Rachael Gregson, Janet Stocks, Tim J. Cole, Eleanor Main. Repeatability of physiotherapy chest wall vibrations applied spontaneously breathing adults. Physiotherapy 95 (2009) 36-42; McCA- RREN B, Alison J A and Herbert R D (2006): Vibration and its effect on the respiratory system. Australian Journal of Physiotherapy 52: 39-43]. It is believed that such vibration stimulates the skeletal muscles involved in breathing, although vibration at 100, 105, or 120 Hz might also potentially excite intrapulminary receptors [A. P. BINKS, E. Bloch-Salisbury, R. B. Banzett, R. M. Schwartzstein. Oscillation of the lung by chest-wall vibration. Respiration Physiology 126 (2001) 245-249; Ikuo HOMMA. Inspiratory inhibitory reflex caused by the chest wall vibration in man. Respiration Physiology (1980) 39, 345-353]. Similarly, non-invasive mechanical ventilators use a face mask, an upper body shell known as a cuirass, or a Hayek Oscillator to force air in and out of the lungs, thereby avoiding the use of an invasive endotracheal tube.

The mechanical larynx is another example of a non-invasive mechanical device, which is placed under the mandible so as to produce vibrations that the patient uses to create speech. Similarly, a hearing aid directs mechanical vibrations (acoustical or sound vibrations) to the eardrum. Because it is placed in a natural orifice (the ear canal or external auditory meatus), the hearing aid is considered to be non-invasive. Extracorporeal shock wave lithotripsy is another non-invasive mechanical treatment, which is used to break-up kidney stones by focusing onto the stones a high-intensity acoustic pulse that originates from outside the body.

Imaging procedures that require the insertion of an endoscope or similar device through the skin or into a cavity beyond a natural orifice (e.g., bronchoscopy or colonoscopy) are invasive. But capsule endoscopy, in which a camera having the size and shape of a pill is swallowed, is non-invasive because the capsule endoscope is swallowed rather than inserted into a body cavity. Such a swallowed capsule could also be used to perform non-invasive stimulation of tissue in its vicinity from within the digestive tract. Similarly, administration of a drug or biologic through a transdermal patch is non-invasive, whereas administration of a drug or biologic through a hypodermic needle is invasive. The acts of taking a drug or biologic orally or through inhalation are not considered to be medical procedures in the strict sense (so the issue of invasiveness does not arise), because those acts are functionally indistinguishable from the normal acts of eating, drinking, or breathing substances that may be metabolized or otherwise disposed of by the body.

Radiological procedures, such as X-ray imaging (fluoroscopy), magnetic resonance imaging and ultrasound imaging, are non-invasive unless a transducer is inserted into a body cavity or under the skin (e.g., when an ultrasound transducer is inserted into the patient's esophagus). However, a non-invasive radiological procedure may be a component of a larger procedure having invasive components. For example, a component of the procedure is invasive when the formation of an image or delivery of energy relies on the presence of a contrast agent, enhancer, tissue-specific label or radio-active emitter that is inserted into the patient with a hypodermic needle.

In the present application, the non-invasive delivery of energy is intended ultimately to dilate bronchial passages, by relaxing bronchial smooth muscle. The smooth muscles that line the bronchial passages are controlled by a confluence of vagus and sympathetic nerve fiber plexuses. Spasms of the bronchi during asthma attacks and anaphylactic shock can often be directly related to pathological signaling within these plexuses. Anaphylactic shock and asthma are major health concerns.

Asthma, and other airway occluding disorders resulting from inflammatory responses and inflammation-mediated bronchoconstriction, affects an estimated eight to thirteen million adults and children in the United States. A significant subclass of asthmatics suffers from severe asthma. An estimated 5,000 persons die every year in the United States as a result of asthma attacks. Up to twenty percent of the populations of some countries are affected by asthma, estimated at more than a hundred million people worldwide. Asthma's associated morbidity and mortality are rising in most countries despite increasing use of anti-asthma drugs.

Asthma is characterized as a chronic inflammatory condition of the airways. Typical symptoms are coughing, wheezing, tightness of the chest and shortness of breath. Asthma is a result of increased sensitivity to foreign bodies such as pollen, dust mites and cigarette smoke. The body, in effect, overreacts to the presence of these foreign bodies in the airways. As part of the asthmatic reaction, an increase in mucous production is often triggered, exacerbating airway restriction. Smooth muscle surrounding the airways goes into spasm, resulting in constriction of airways. The airways also become inflamed. Over time, this inflammation can lead to scarring of the airways and a further reduction in airflow. This inflammation leads to the airways becoming more irritable, which may cause an increase in coughing and increased susceptibility to asthma episodes.

Two medicinal strategies exist for treating this problem for patients with asthma. The condition is typically managed by means of inhaled medications that are taken after the onset of symptoms, or by injected and/or oral medication that are taken chronically. The medications typically fall into two categories; those that treat the inflammation, and those that treat the smooth muscle constriction. The first is to provide anti-inflammatory medications, like steroids, to treat the airway tissue, reducing its tendency to over-release the molecules that mediate the inflammatory process. The second strategy is to provide a smooth muscle relaxant (e.g. an anticholinergic) to reduce the ability of the muscles to constrict.

It has been highly preferred that patients rely on avoidance of triggers and anti-inflammatory medications, rather than on the bronchodilators as their first line of treatment. For some patients, however, these medications, and even the bronchodilators are insufficient to stop the constriction of their bronchial passages, and more than five thousand people suffocate and die every year as a result of asthma attacks.

Anaphylaxis likely ranks among the other airway occluding disorders of this type as the most deadly, claiming many deaths in the United States every year. Anaphylaxis (the most severe form of which is anaphylactic shock) is a severe and rapid systemic allergic reaction to an allergen. Minute amounts of allergens may cause a life-threatening anaphylactic reaction. Anaphylaxis may occur after ingestion, inhalation, skin contact or injection of an allergen. Anaphylactic shock usually results in death in minutes if untreated. Anaphylactic shock is a lifethreatening medical emergency because of rapid constriction of the airway. Brain damage sets in quickly without oxygen.

The triggers for these fatal reactions range from foods (nuts and shellfish), to insect stings (bees), to medication (radio contrasts and antibiotics). It is estimated that 1.3 to 13 million people in the United States are allergic to venom associated with insect bites; 27 million are allergic to antibiotics; and 5-8 million suffer food allergies. All of these individuals are at risk of anaphylactic shock from exposure to any of the foregoing allergens. In addition, anaphylactic shock can be brought on by exercise. Yet all are mediated by a series of hypersensitivity responses that result in uncontrollable airway occlusion driven by smooth muscle constriction, and dramatic hypotension that leads to shock. Cardiovascular failure, multiple organ ischemia, and asphyxiation are the most dangerous consequences of anaphylaxis.

Anaphylactic shock requires advanced medical care immediately. Current emergency measures include rescue breathing; administration of epinephrine; and/or intubation if possible. Rescue breathing may be hindered by the closing airway but can help if the victim stops breathing on his own. Clinical treatment typically consists of antihistamines (which inhibit the effects of histamine at histamine receptors) which are usually not sufficient in anaphylaxis, and high doses of intravenous corticosteroids. Hypotension is treated with intravenous fluids and sometimes vasoconstrictor drugs. For bronchospasm, bronchodilator drugs such as salbutamol are employed.

Given the common mediators of both asthmatic and anaphylactic bronchoconstriction, it is not surprising that asthma sufferers are at a particular risk for anaphylaxis. Still, estimates place the numbers of people who are susceptible to such responses at more than 40 million in the United States alone.

Tragically, many of these patients are fully aware of the severity of their condition, and die while struggling in vain to manage the attack medically. Many of these incidents occur in hospitals or in ambulances, in the presence of highly trained medical personnel who are powerless to break the cycle of inflammation and bronchoconstriction (and life-threatening hypotension in the case of anaphylaxis) affecting their patient.

Unfortunately, prompt medical attention for anaphylactic shock and asthma are not always available. For example, epinephrine is not always available for immediate injection. Even in cases where medication and attention is available, life saving measures are often frustrated because of the nature of the symptoms. Constriction of the airways frustrates resuscitation efforts, and intubation may be impossible because of swelling of tissues.

Typically, the severity and rapid onset of anaphylactic reactions does not render the pathology amenable to chronic treatment, but requires more immediately acting medications. Among the most popular medications for treating anaphylaxis is epinephrine, commonly marketed in so-called "Epipen" formulations and administering devices, which potential sufferers carry with them at all times. In addition to serving as an extreme bronchodilator, epinephrine raises the patient's heart rate dramatically in order to offset the hypotension that accompanies many reactions. This cardiovascular stress can result in tachycardia, heart attacks and strokes.

Chronic obstructive pulmonary disease (COPD) is a major cause of disability, and is the fourth leading cause of death in the United States. More than 12 million people are currently diagnosed with COPD. An additional 12 million likely have the disease and don't even know it. COPD is a progressive disease that makes it hard for the patient to breathe. COPD can cause coughing that produces large amounts of mucus, wheezing, shortness of breath, chest tightness and other symptoms. Cigarette smoking is the leading cause of COPD, although longterm exposure to other lung irritants, such as air pollution, chemical fumes or dust may also contribute to COPD. In COPD, less air flows in and out of the bronchial airways for a variety of reasons, including loss of elasticity in the airways and/or air sacs, inflammation and/or destruction of the walls between many of the air sacs and overproduction of mucus within the airways.

The term COPD includes two primary conditions: emphysema and chronic obstructive bronchitis. In emphysema, the walls between many of the air sacs are damaged, causing them to lose their shape and become floppy. This damage also can destroy the walls of the air sacs, leading to fewer and larger air sacs instead of many tiny ones. In chronic obstructive bronchitis, the patient suffers from permanently irritated and inflamed bronchial tissue that is slowly and progressively dying. This causes the lining to thicken and form thick mucus, making it hard to breathe. Many of these patients also experience periodic episodes of acute airway reactivity (i.e., acute exacerbations), wherein the smooth muscle surrounding the airways goes into spasm, resulting in further constriction and inflammation of the airways. Acute exacerbations occur, on average, between two and three times a year in patients with moderate to severe COPD and are the most common cause of hospitalization in these patients (mortality rates are 11%). Frequent acute exacerbations of COPD cause lung function to deteriorate quickly, and patients never recover to the condition they were in before the last exacerbation. Similar to asthma, current medical management of these acute exacerbations is often insufficient.

Unlike cardiac arrhythmias, which can be treated chronically with pacemaker technology, or in emergent situations with equipment like defibrillators (implantable and external), there is virtually no commercially available medical equipment that can chronically reduce the baseline sensitivity of the smooth muscle tissue in the airways to reduce the predisposition to asthma attacks, reduce the symptoms of COPD or to break the cycle of bronchial constriction associated with an acute asthma attack or anaphylaxis.

Therefore, there is a need in the art for new products and methods for treating the immediate symptoms of bronchial constriction resulting from pathologies such as anaphylactic shock, asthma and COPD. In particular, there is a need in the art for non-invasive devices and methods to treat the immediate symptoms of bronchial constriction. Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are generally painless and may be performed without the need for even local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace, and the cost of non-invasive procedures may be reduced relative to comparable invasive procedures.

SUMMARY OF THE INVENTION

The present invention involves products and methods for the treatment of asthma, COPD, anaphylaxis, and other pathologies involving the constriction of the primary airways, utilizing an energy source (comprising electrical and/or magnetic, mechanical and/or acoustic, and optical and/or thermal energy), that may be transmitted non-invasively to, or in close proximity to, a selected nerve to temporarily stimulate, block and/or modulate the signals in the selected nerve. The present invention is particularly useful for the acute relief of symptoms associated with bronchial constriction, i.e., asthma attacks, COPD exacerbations and/or anaphylactic reactions. The teachings of the present invention provide an emergency response to such acute symptoms, by producing immediate airway dilation and/or heart function increase to enable subsequent adjunctive measures (such as the administration of epinephrine) to be effectively employed.

In one aspect of the present invention, a method of treating bronchial constriction comprises stimulating selected nerve fibers responsible for reducing the magnitude of constriction of smooth bronchial muscle to increase the activity of the selected nerve fibers.

In a preferred embodiment, the selected nerve fibers comprise those that send a parasympathetic, afferent vagal signal to the brain, which then triggers an efferent sympathetic signal to stimulate the release of catecholamines (comprising endogenous beta-agonists, epinephrine and/or norepinephrine) from the adrenal glands and/or from nerve endings that are distributed throughout the body. In yet other embodiments, the method includes stimulating, inhibiting, blocking or otherwise modulating other nerves that release systemic bronchodilators or nerves that directly modulate parasympathetic ganglia transmission (by stimulation or inhibition of preganglionic to postganglionic transmissions). In an alternative embodiment, the fibers responsible for bronchodilation are interneurons that are completely contained within the walls of the bronchial airways. These interneurons are responsible for modulating the cholinergic nerves in the bronchial passages. In this embodiment, the increased activity of the interneurons will cause inhibition or blocking of the cholinergic nerves responsible for bronchial constriction, thereby facilitating opening of the airways.

The stimulating step is preferably carried out without substantially stimulating excitatory nerve fibers, such as parasympathetic cholinergic nerve fibers, that are responsible for increasing the magnitude of constriction of smooth muscle. In this manner, the activity of the nerve fibers responsible for bronchodilation are increased without increasing the activity of the cholinergic fibers which would otherwise induce further constriction of the smooth muscle. Alternatively, the method may comprise the step of actually inhibiting or blocking these cholinergic nerve fibers such that the nerves responsible for bronchodilation are stimulated while the nerves responsible for bronchial constriction are inhibited or completely blocked. This blocking/inhibiting signal may be separately applied to the inhibitory nerves; or it may be part of the same signal that is applied to the nerve fibers responsible for bronchodilation.

In an alternative embodiment, a method of treating bronchial constriction comprises stimulating, inhibiting, blocking or otherwise modulating selected efferent sympathetic nerves responsible for mediating bronchial passages either directly or indirectly. The selected efferent sympathetic nerves may be nerves that directly innervate the bronchial smooth muscles. It has been postulated that asthma patients typically have more sympathetic nerves that directly innervate the bronchial smooth muscle than individuals that do not suffer from asthma.

In another aspect of the invention, a method of treating bronchial constriction includes applying an energy impulse to a target region in the patient and acutely reducing the magnitude of bronchial constriction in the patient. The energy impulse is transmitted non-invasively from an energy source, comprising electrical and/or magnetic, mechanical and/or acoustic, and optical and/or thermal sources of energy. As used herein, the term acutely means that the energy impulse immediately begins to interact with one or more nerves to produce a response in the patient. The energy impulse is preferably sufficient to promptly and quantitatively ameliorate a symptom, for example, to increase the Forced Expiratory Volume in about 1 second ($FEV_1$) of the patient by a clinically significant amount in a period of time less than about 6 hours, preferably less than about 3 hours and more preferably less than about 90 minutes and even more preferably less that about 15 minutes. A clinically significant amount is defined herein as at least an about 12% increase in the patient's $FEV_1$ versus the $FEV_1$ measured prior to application of the energy impulse. In an exemplary embodiment, the energy impulse is sufficient to increase the $FEV_1$ by at least about 19% over the $FEV_1$ as predicted.

In another aspect of the invention, a method for treating bronchial constriction comprises applying one or more energy impulse(s) of a frequency from about 15 Hz to about 50 Hz to a selected region within a patient to reduce a magnitude of constriction of bronchial smooth muscle. In a preferred embodiment, the method includes positioning the coil of a magnetic stimulator non-invasively on or above a patient's neck and applying a magnetically-induced electrical impulse non-invasively to the target region within the neck to stimulate, inhibit or otherwise modulate selected nerve fibers that interact with bronchial smooth muscle. Preferably, the target region is adjacent to, or in close proximity with, the carotid sheath.

In one embodiment of the present invention, the source of stimulation energy is a magnetic stimulator that preferably operates to induce an electrical signal within the tissue, where the induced electrical signal has a frequency from about 1 Hz to about 3000 Hz, a pulse duration from between about 10 to about 1000 microseconds, and an amplitude from about 1 to about 20 volts. The induced electrical signal may be one or more of: a full or partial sinusoid, a square wave, a rectangular wave, and triangle wave. By way of example, the at least one induced electrical signal may be of a frequency from about 15 Hz to about 35 Hz. By way of example, at least one induced electrical signal may have a pulsed on-time from about 50 to about 1000 microseconds, such as from about 100 to about 300 microseconds, or about 200 microseconds. By way of example, the at least one induced electrical signal may have an amplitude from about 5 to about 15 volts, such as about 12 volts.

Applicant has made the unexpected discovered that applying an electrical impulse to a selected region of a patient's neck within this particular frequency range results in almost immediate and significant improvement in bronchodilation, as discussed in further detail below. Applicant has further discovered that applying electrical impulses outside of the selected frequency range (from about 15 Hz to about 50 Hz) does not result in significant improvement and, in some cases, may worsen the patient's bronchoconstriction. Preferably, the frequency is about 25 Hz. In this embodiment, the electrical impulse(s) have an amplitude from about 0.5 to about 12 volts and have a pulsed on-time from about 50 to about 500 microseconds, preferably from about 200 to about 400 microseconds. The preferred voltage will depend on the size and shape of the apparatus used to deliver the electrical impulse and the distance between that apparatus and the target nerves. In certain embodiments the electrical impulse preferably has an amplitude of at least about 6 volts and more preferably from about 7 to about 12 volts. In other embodiments the amplitude is preferably lower, i.e., less than about 6 volts and more preferably from about 0.1 to about 2 volts.

The energy impulse(s) are applied in a manner that reduces the constriction of the smooth muscle lining the bronchial passages to relieve the spasms that occur during anaphylactic shock, acute exacerbations of COPD or asthma attacks. In some embodiments, the mechanisms by which the appropriate impulse is applied to the selected region within the patient include positioning a magnetic stimulator coil non-invasively on or above the patient's neck in the vicinity of the nervous tissue controlling the pulmonary and/or cardiac muscles, which coil is coupled to an external magnetic impulse/eddy-current generating device. The electric field and/or eddy-currents induced by the coil of the magnetic stimulator creates a field of effect that permeates the target nerve fibers and causes the stimulating, blocking and/or modulation of signals to the subject smooth muscles, and/or the blocking and/or affecting of histamine response. It shall be understood that leadless impulses as shown in the art may be utilized for applying impulses to the target regions.

In other embodiments, a magnetic stimulator coil is positioned non-invasively on or above an anatomical location other than the patient's neck, in the vicinity of nervous tissue controlling bronchodilation, which coil is coupled to an external magnetic-field impulse/eddy-current impulse generating device. The electromagnetic field and/or eddy-currents induced as energy impulses by the coil of the magnetic stimulator create a field of effect that permeates the target nerve fibers and cause the stimulating, blocking, and/or modulation of signals to the subject smooth muscles, and/or the blocking and/or affecting of histamine response.

In other embodiments, the mechanisms by which the appropriate energy impulse is applied to the selected region within the patient comprise positioning a mechanical or acoustical vibrator (or mechanical-vibration/sound conducting form-fitting garment) non-invasively, on or above the patient's neck, on or above the patient's ear or ear-canal orifice, or on or above some other anatomical location in the vicinity of nervous tissue controlling bronchodilation, which mechanical or acoustical vibrator is coupled to an external mechanical-impulse or sound-impulse generating device. The mechanical or acoustical vibrations transmitted non-invasively by the vibrator creates a field of effect that permeates the target nerve fibers and cause the stimulating, blocking, and/or modulation of signals to the subject smooth muscles, and/or the blocking and/or affecting of histamine response.

In other embodiments, the mechanisms by which the appropriate energy impulse is applied to the selected region within the patient comprise positioning a light or heat emitting device (or a light-conducting or heat-conducting form-fitting garment) non-invasively, on or above the patient's ear or ear-canal orifice, or on or above some other anatomical location in the vicinity of nervous tissue controlling bronchodilation, which light or heat emitting device is coupled to an external light or heat generating source, said source being a device that can generate light or heat as impulses of energy corresponding to electromagnetic radiation having wavelengths in the infra-red, far-infrared, visible, or ultra-violet ranges of electromagnetic radiation (having wavelengths in the range of about 10-8 meters to about 10-3 meters, inclusive). The light or heat transmitted non-invasively from the light or heat emitting device creates a field of effect that permeates the target nerve fibers and cause the stimulating, blocking, and/or modulation of signals to the subject smooth muscles, and/or the blocking and/or affecting of histamine response.

In other embodiments, the mechanisms by which the appropriate energy impulse is applied to the selected region within the patient comprise positioning the distal ends of one or more electrical lead (or electrically conducting form-fitting garment) non-invasively, on or above the patient's neck, on or above the patient's ear or ear-canal orifice, or on or above some other anatomical location in the vicinity of nervous tissue controlling bronchodilation, which lead or leads are coupled to an external electrical impulse generating device, for example via an electrode. The electric field generated non-invasively at the distal tip of the lead creates a field of effect that permeates the target nerve fibers and cause the stimulating, blocking, and/or modulation of signals to the subject smooth muscles, and/or the blocking and/or affecting of histamine response.

The novel systems, devices and methods for treating bronchial constriction are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference. If any disclosures are incorporated herein by reference and such disclosures conflict in part and/or in whole with the present disclosure, then to the extent of conflict, and/or broader disclosure, and/or broader definition of terms, the present disclosure controls. If such disclosures conflict in part and/or in whole with one another, then to the extent of conflict, the later-dated disclosure controls.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIGS. 15-18 graphically illustrate exemplary experimental data obtained on human patients in accordance with multiple embodiments of the present invention.

DETAILED DESCRIPTION OF THE PREFERRED EMBODIMENTS

Figure 1:
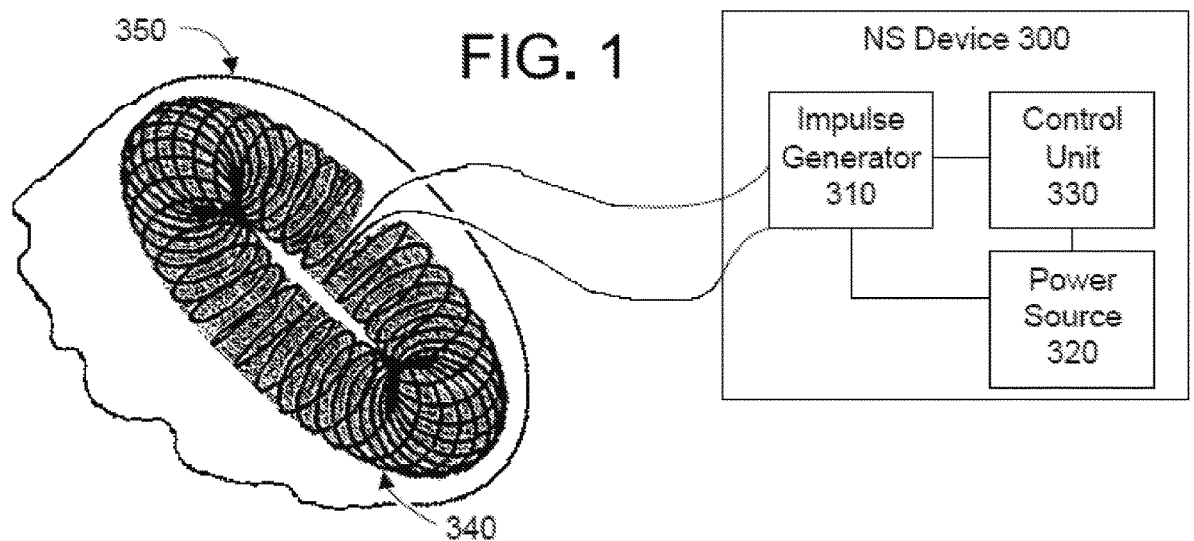
FIG. 1 is a schematic view of a nerve modulating device according to the present invention, which supplies controlled pulses of electrical current to a magnetic stimulator coil.

In the present invention, energy is transmitted non-invasively to a patient. Transmission of energy is defined herein to mean the macroscopic transfer of energy from one point to another point through a medium, including possibly a medium that is free space, such that in going from a point of origin to a point of destination, the energy is transferred successively to the medium at points along a path connecting the points of origin and destination. Some energy at the point of origin will ordinarily be lost to the medium before arriving at the point of destination. If energy is radiated in all directions from the point of origin, then only that energy following a path from the point of origin to the destination point is considered to be transmitted. According to this definition, electrical, magnetic, electromagnetic, mechanical, acoustical, and thermal energy may be transmitted. But chemical energy in the form of chemical bonds would ordinarily not fall under this definition of energy transmission, because when moving macroscopically between two points, e.g., by diffusion, the energy contained within chemical bonds would not ordinarily be transferred to a medium at intervening points. Thus, the diffusion of chemical substances would ordinarily be considered to be a flux of mass ($kg \cdot m-2 \cdot s-1$) rather than a flux of energy ($J \cdot m-2 \cdot s-1$).

One aspect of the present invention teaches non-invasive methods for treating bronchial constriction by stimulating selected nerve fibers that are responsible for reducing the magnitude of constriction of smooth bronchial muscle, such that the activity of those selected nerve fibers is increased and smooth bronchial muscle is dilated. Prominent among such nerve fibers are some that are associated with the vagus nerve.

As described below in connection with different embodiments of the present invention, non-invasive methods involving the transmission of magnetic and/or electrical energy as well as mechanical and/or acoustic energy have been used to stimulate nerves that could be responsible for bronchodilation, particularly the vagus nerve. However, to the knowledge of the present applicants, they have never been performed in such a way as to achieve bronchodilation. Conversely, energy has been applied to patients in such a way as to bring about bronchodilation, but those applications involve methods that are invasive, not non-invasive. For example, U.S. Pat. No. 7,740,017, entitled Method for treating an asthma attack, to Danek et al., discloses an invasive method for directing radio frequency energy to the lungs to bring about bronchodilation. U.S. Pat. No. 7,264,002, entitled Methods of treating reversible obstructive pulmonary disease, to Danek et al., discloses methods of treating an asthmatic lung invasively, by advancing a treatment device into the lung and applying energy. Those invasive methods attempt to dilate the bronchi directly, rather than to stimulate nerve fibers that in turn bring about bronchodilation. However, our own experiments, which are described below, demonstrate that minimally invasive electrical stimulation of nerve fibers can in fact achieve bronchodilation. They motivate the present application that discloses several methods and devices to stimulate such nerve fibers non-invasively, in order to produce bronchodilation.

In the preferred embodiments, a time-varying magnetic field originating outside of a patient is applied to a patient, such that the magnetic field generates an electromagnetic field and/or induces eddy currents within tissue of the patient. The invention is particularly useful for inducing applied electrical impulses that interact with the signals of one or more nerves, or muscles, to achieve a therapeutic result, such as relaxation of the smooth muscle of the bronchia. In particular, the present invention provides methods and devices for immediate relief of acute symptoms associated with bronchial constriction such as asthma attacks, COPD exacerbations and/or anaphylactic reactions.

For convenience, much of the remaining disclosure will be directed specifically to treatment in or around the carotid sheath with devices positioned non-invasively on or near a patient's neck, but it will be appreciated that the systems and methods of the present invention can be applied equally well to other tissues and nerves of the body, including but not limited to other parasympathetic nerves, sympathetic nerves, spinal or cranial nerves. In addition, the present invention can be used to directly or indirectly stimulate or otherwise modulate nerves that innervate bronchial smooth muscle. While the exact physiological causes of asthma, COPD and anaphylaxis have not been determined, the present invention postulates that the direct mediation of the smooth muscles of the bronchia is the result of activity in one or more nerves near or in the carotid sheath. In the case of asthma, it appears that the airway tissue has both (i) a hypersensitivity to the allergen that causes the overproduction of the cytokines that stimulate the cholinergic receptors of the nerves and/or (ii) a baseline high parasympathetic tone or a high ramp up to a strong parasympathetic tone when confronted with any level of cholinergic cytokine. The combination can be lethal. Anaphylaxis appears to be mediated predominantly by the hypersensitivity to an allergen causing the massive overproduction of cholinergic receptor activating cytokines that overdrive the otherwise normally operating vagus nerve to signal massive constriction of the airways. Drugs such as epinephrine drive heart rate up while also relaxing the bronchial muscles, effecting temporary relief of symptoms from these conditions. Experience has shown that severing the vagus nerve (an extreme version of reducing the parasympathetic tone) has an effect similar to that of epinephrine on heart rate and bronchial diameter in that the heart begins to race (tachycardia) and the bronchial passageways dilate. One aspect of the present invention is that it may produce an effect similar to that of epinephrine in relaxing the contraction of smooth muscle in bronchial passageways. However, the present invention is not intended to reverse hypersensitivity to an allergen or to modulate the production of cytokines.

To investigate the mechanism by which vagal (or vagus) nerve stimulation (VNS) can result in bronchodilation, the present applicant and colleagues performed experiments that are reported herein [published as conference proceedings: Bruce J. SIMON, Charles W. Emala, Lawrence M. Lewis, Daniel Theodoro, Yanina Purim-Shem-Tov, Pedro Sepulveda, Thomas J. Hoffmann, Peter Staats. Vagal Nerve Stimulation for Relief of Bronchoconstriction: Preliminary Clinical Data and Mechanism of Action. Proceedings page 119 of Neuromodulation: 2010 and Beyond; North American Neuromodulation Society 13th Annual Meeting, Dec. 3-6, 2009]. The experiments are described in detail later in the present application, but the following is a summary of their design, results, and interpretation.

Animal studies were first performed. Under IACUC approved protocols, male Hartley guinea pigs were anesthetized with i.p. urethane and ventilated through a tracheostomy. Bronchoconstriction was induced via iv histamine or acetylcholine with or without simultaneous, bilateral VNS at 25 Hz, 200 ms, 1-3 V. Selective antagonists (L-NAME/iNANC, propranolol/sympathetic) and vagal ligation were used to elucidate the neural pathways responsible for the bronchodilation response. The results of these animal studies were as follows. Ligating both vagus nerves caudal to the stimulating electrodes did not block the VNS-mediated attenuation of bronchoconstriction while ligating rostrally did block the attenuation of bronchoconstriction. This suggests that the mechanism was mediated through an afferent neural pathway. Blockade of nitric oxide synthesis by pretreatment with L-NAME (a primary mediator of inhibitory non-adrenergic, non-cholinergic (iNANC) bronchodilator pathways) had no effect on VNS-mediated attenuation of bronchoconstriction while pretreatment with propranolol reversibly blocked the effect.

Human studies were also performed. Under an FDA IDE with IRB approval, six adult patients were studied who were seen in the emergency department for moderate to severe asthma (FEV1 16%-69%) and who failed to respond to conventional pharmacologic therapy, including β2-adrenergic receptor agonists (6/6) and oral steroid treatment (5/6). Following consent, patients were prepped, draped, and using only local anesthesia, underwent percutaneous placement of an electrode lead in the vicinity of the carotid sheath, assisted by ultrasound guidance. Treatment consisted of up to 180 minutes of continuous electrical stimulation at 25 Hz, 200 ms, 1-12 V. Benefit was determined by changes in FEV1. The results of these clinical studies were as follows. Within 30 minutes of VNS therapy, the mean % predicted FEV1 increased from 49.8±7.8 to 58.8±7.5 (p=0.003). FEV1 continued to improve during treatment (mean maximum increase of ~44%) and benefit remained after treatment ended (at 30 minutes post, % predicted FEV1 was 67.1±8.1, p=0.004). There were no episodes of hypotension, bradycardia, diaphoresis, or increased tachycardia during stimulation, nor complications within the one week follow-up.

We therefore conclude the following from the animal and clinical studies. Preliminary data suggests that VNS can safely induce significant bronchodilation in humans during an exacerbation of asthma in those who with a poor response to standard pharmacological treatment. Preliminary animal data indicates that VNS activates afferent nerves and may act through a sympathetic reflex pathway to mediate bronchodilation. Thus, we found that bronchodilation resulting from stimulation of the vagus nerve works by causing the systemic release of the natural, endogenous β-agonists, epinephrine and norepinephrine. These catecholamines can reach the constricted bronchial smooth muscle through an internal, systemic pathway, thereby overcoming any potential problems with inhaled β-agonists, for example, due to mucus congestion. The electrical field delivered to the vagus nerve was optimized to stimulate the release of these hormones into the circulation at concentrations that produce bronchial smooth muscle relaxation, but have little effect on heart rate or blood pressure. The data suggest that the release of these catecholamines is mediated by a parasympathetic, afferent vagal signal to the brain, which then triggers an efferent sympathetic signal to stimulate the release of catecholamines from the adrenal glands. These animal data show that the stimulator is effective even if the vagus nerve is tied off distal to the electrode and that the bronchodilation effect can be blocked with the β-blocker propranolol. In addition, stimulation was found to be ineffective in animals that have had their adrenal glands removed.

In accordance with the present invention, the delivery, in a patient suffering from severe asthma, COPD or anaphylactic shock, of an impulse of energy sufficient to stimulate, block and/or modulate transmission of signals of selected nerve fibers will result in relaxation of the bronchi smooth muscle, dilating airways and/or counteract the effect of histamine on the vagus nerve. Depending on the placement of the impulse, the stimulating, blocking and/or modulating signal can also raise the heart function.

Stimulating, blocking and/or modulating the signal in selected nerves to reduce parasympathetic tone provides an immediate emergency response, much like a defibrillator, in situations of severe asthma or COPD attacks or anaphylactic shock, providing immediate temporary dilation of the airways and optionally an increase of heart function until subsequent measures, such as administration of epinephrine, rescue breathing and intubation can be employed. Moreover, the teachings of the present invention permit immediate airway dilation and/or heart function increase to enable subsequent life saving measures that otherwise would be ineffective or impossible due to severe constriction or other physiological effects. Treatment in accordance with the present invention provides bronchodilation and optionally increased heart function for a long enough period of time so that administered medication such as epinephrine has time to take effect before the patient suffocates.

In a preferred embodiment, a method of treating bronchial constriction comprises stimulating selected nerve fibers responsible for reducing the magnitude of constriction of smooth bronchial muscle to increase the activity of the selected nerve fibers. Certain signals of the parasympathetic nerve fibers cause a constriction of the smooth muscle surrounding the bronchial passages, while other signals of the parasympathetic nerve fibers carry the opposing signals that tend to open the bronchial passages. Specifically, it should be recognized that certain signals, such as cholinergic fibers mediate a response similar to that of histamine, while other signals generate an effect similar to epinephrine. [CANNING, Brendan J. Reflex regulation of airway smooth muscle tone. J Appl Physiol 101: 971-985, 2006.] As described in connection with our experiments summarized above, the latter fibers include those that may directly or indirectly cause the systemic release of catecholamines from the adrenal glands and/or from nerve endings distributed throughout the body, so in what follows, those latter fibers will be called collectively "epinephrine-like-effect" fibers. Repeated stimulation of some such fibers may cause the repeated pulsatile systemic release of epinephrine (and/or other catecholamies), leading eventually to circulating steady state concentrations of catecholamines that are determined by the stimulation frequency as well as the half-life of circulating catecholamines. Given the postulated balance between these signals, stimulating the "epinephrine-like-effect" nerve fibers and/or blocking or removing the cholinergic signals should create an imbalance emphasizing bronchodilation.

In one embodiment of the present invention, the selected nerve fibers are "epinephrine-like-effect" nerve fibers which are generally responsible for bronchodilation. Stimulation of these "epinephrine-like-effect" fibers increases their activity, thereby increasing bronchodilation and facilitating opening of the airways of the mammal. The stimulation may occur through direct stimulation of the efferent "epinephrine-like-effect" fibers that cause bronchodilation or indirectly through stimulation of the afferent sympathetic or parasympathetic nerves which carry signals to the brain and then back down through the "epinephrine-like-effect" nerve fibers to the bronchial passages.

In certain embodiments, the "epinephrine-like-effect" nerve fibers are associated with the vagus nerve and are thus directly responsible for bronchodilation. Alternatively, the "epinephrine-like-effect" fibers may be interneurons that are completely contained within the walls of the bronchial airways. These interneurons are responsible for modulating the cholinergic nerves in the bronchial passages. In this embodiment, the increased activity of the "epinephrine-like-effect" interneurons will cause inhibition or blocking of the cholinergic nerves responsible for bronchial constriction, thereby facilitating opening of the airways.

As discussed above, certain parasympathetic signals mediate a response similar to histamine, thereby causing a constriction of the smooth muscle surrounding the bronchial passages. Accordingly, the stimulating step of the present invention is preferably carried out without substantially stimulating the parasympathetic nerve fibers, such as the cholinergic nerve fibers associated with the vagus nerve, that are responsible for increasing the magnitude of constriction of smooth muscle. In this manner, the activity of the "epinephrine-like-effect" nerve fibers are increased without increasing the activity of the adrenergic fibers which would otherwise induce further constriction of the smooth muscle. Alternatively, the method may comprise the step of actually inhibiting or blocking these cholinergic nerve fibers such that the nerves responsible for bronchodilation are stimulated while the nerves responsible for bronchial constriction are inhibited or completely blocked. This blocking signal may be separately applied to the inhibitory nerves; or it may be part of the same signal that is applied to the "epinephrine-like-effect" nerve fibers.

While it is believed that there are little to no direct sympathetic innervations of the bronchial smooth muscle in most individuals, recent evidence has suggested asthma patients do have such sympathetic innervations within the bronchial smooth muscle. In addition, the sympathetic nerves may have an indirect effect on the bronchial smooth muscle.

Accordingly, alternative embodiments of the prevent invention contemplate a method of stimulating selected efferent sympathetic nerves responsible for mediating bronchial passages either directly or indirectly. The selected efferent sympathetic nerves may be nerves that directly innervate the smooth muscles, nerves that release systemic bronchodilators or nerves that directly modulate parasympathetic ganglia transmission (by stimulation or inhibition of preganglionic to postganglionic transmissions).

Method and devices of the present invention are particularly useful for providing substantially immediate relief of acute symptoms associated with bronchial constriction such as asthma attacks, COPD exacerbations and/or anaphylactic reactions. One of the key advantages of the present invention is the ability to provide almost immediate dilation of the bronchial smooth muscle in patients suffering from acute bronchoconstriction, opening the patient's airways and allowing them to breathe and more quickly recover from an acute episode (i.e., a relatively rapid onset of symptoms that are typically not prolonged or chronic).

The magnitude of bronchial constriction in a patient is typically expressed in a measurement referred to as the Forced Expiratory Volume in 1 second ($FEV_1$). $FEV_1$ represents the amount of air a patient exhales (expressed in liters) in the first second of a pulmonary function test, which is typically performed with a spirometer. The spirometer compares the $FEV_1$ result to a standard for the patient, which is based on the predicted value for the patient's weight, height, sex, age and race. This comparison is then expressed as a percentage of the $FEV_1$ as predicted. Thus, if the volume of air exhaled by a patient in the first second is 60% of the predicted value based on the standard, the $FEV_1$ will be expressed in both the actual liters exhaled and as a percentage of predicted (i.e., 60% of predicted). In practice, a baseline value of FEV1 is measured, and after a therapeutic intervention, a second value of FEV1 is measured in order to ascertain the efficacy of the intervention. It should be noted that interventions known to dilate the bronchi (e.g., administration of epinephrine or the teachings of the present invention) are most likely to succeed when the patient's baseline FEV1 value is in the range −1 to −5 standard deviations of the statistical distribution of values of FEV1 for individuals in the population at large. This is because if the baseline value is outside that range, the patient's breathing problem is less likely to be due to bronchoconstriction and more likely to be due to something else, such as inflammatory mechanisms.

Certain other measurements may act as surrogates for the measurement of $FEV_1$. Those other non-invasive measurements are particularly useful for patients who cannot cooperate to perform measurements made by spirometry, or for settings in which it is not possible to perform spirometry. Because those other measurements may be used to generate a non-invasive, continuous signal that indicates the efficacy of stimulating the selected nerves, they will be discussed below in connection with their use to provide a feedback signal in the present invention, for adjusting the power of the applied impulse, as well as for adjustment of other stimulation parameters. It should be noted here that one of them, the interrupter technique (Rint) measures airway resistance, which according to Poiseuille's Law for laminar air flow, is inversely proportional to the fourth power of the caliber of dilation of the bronchi.

The measurement of $FEV_1$ entails first measuring forced expiration volume as a function of time (the maximum expiratory flow-volume curve, or MEFV, which may be depicted in different ways, e.g., normalized to percentage of vital capacity), then reading the value of the MEFV curve at the one second point. Because a single parameter such as $FEV_1$ cannot characterize the entire MEFV curve, it is understood that the MEFV curve itself (or a set of parameters derived from it) more accurately represents the patient's respiratory status than the $FEV_1$ value alone [Francois HAAS, Kenneth Axen, and John Salazar Schicchi. Use of Maximum Expiratory Flow-Volume Curve Parameters in the Assessment of Exercise-induced Bronchospasm. Chest 1993; 103:64-68]. Furthermore, it is understood that in order to understand the functional relationship between the magnitude of bronchoconstriction (literally, a reduction in the average caliber of bronchial lumen) and $FEV_1$, one does so by first considering the relation of each of them to the MEFV curve [Rodney K. LAMBERT and Theodore A. Wilson. Smooth muscle dynamics and maximal expiratory flow in asthma. J Appl Physiol 99: 1885-1890, 2005].

As will be discussed below in connection with a detailed description of our experiments that were only summarized above, applicants have disclosed a system and method for increasing a patient's $FEV_1$ in a relatively short period of time. Preferably, the impulse of energy applied to the patient is sufficient to increase the $FEV_1$ of the patient by a clinically significant amount in a period of time less than about 6 hours, preferably less than 3 hours and more preferably less than 90 minutes. In an exemplary embodiment, the clinically significant increase in $FEV_1$ occurs in less than 15 minutes. A clinically significant amount is defined herein as at least a 12% increase in the patient's $FEV_1$ versus the $FEV_1$ prior to application of the electrical impulse.

In the preferred embodiment of the present invention, a magnetic stimulator is used to stimulate selected nerve fibers, particularly the vagus nerve. Magnetic stimulation has been used by several investigators to non-invasively stimulate the vagus nerve. As indicated above, such magnetic stimulation involves the application of a time-varying magnetic field to induce electric currents and fields within tissue. However, none of the following reports of magnetic stimulation of the vagus nerve were related to the treatment of bronchoconstriction. In a series of articles beginning in 1992, Aziz and colleagues describe using non-invasive magnetic stimulation to electrically stimulate the vagus nerve in the neck. [Q. AZIZ et al. Magnetic Stimulation of Efferent Neural Pathways to the Human Oesophagus. Gut 33: S53-S70 (Poster Session F218) (1992); AZIZ, Q., J. C. Rothwell, J. Barlow, A. Hobson, S. Alani, J. Bancewicz, and D. G. Thompson. Esophageal myoelectric responses to magnetic stimulation of the human cortex and the extracranial vagus nerve. Am. J. Physiol. 267 (Gastrointest. Liver Physiol. 30): G827-G835, 1994; Shaheen HAMDY, Qasim Aziz, John C. Rothwell, Anthony Hobson, Josephine Barlow, and David G. Thompson. Cranial nerve modulation of human cortical swallowing motor pathways. Am. J. Physiol. 272 (Gastrointest. Liver Physiol. 35): G802-G808, 1997; Shaheen HAMDY, John C. Rothwell, Qasim Aziz, Krishna D. Singh, and David G. Thompson. Long-term reorganization of human motor cortex driven by short-term sensory stimulation. Nature Neuroscience 1 (issue 1, May 1998):64-68.] SIMS and colleagues stimulated the vagus nerve at and near the mastoid tip. [H. Steven SIMS, Toshiyuki Yamashita, Karen Rhew, and Christy L. Ludlow. Assessing the clinical utility of the magnetic stimulator for measuring response latencies in the laryngeal muscles. Otolaryngol Head Neck Surg 1996; 114:761-7]. KHEDR and colleagues also used a magnetic stimulator to stimulate the vagus nerve at the tip of the mastoid bone [E. M. KHEDR and E-E. M. Aref Electrophysiological study of vocal-fold mobility disorders using a magnetic stimulator. European Journal of Neurology 2002, 9: 259-267; KHEDR, E. M., Abo-Elfetoh, N., Ahmed, M. A., Kamel, N. F., Farook, M., El Karn, M. F. Dysphagia and hemispheric stroke: A transcranial magnetic study. Neurophysiologie Clinique/Clinical Neurophysiology (2008) 38, 235-242)]. SHAFIK stimulated the vagus nerve in the neck, placing the magnetic stimulator on the neck between the sternomastoid muscle and the trachea. [A. SHAFIK. Functional magnetic stimulation of the vagus nerve enhances colonic transit time in healthy volunteers. Tech Coloproctol (1999) 3:123-12]. Among these investigations, the one by SHAFIK stimulated the vagus nerve for the longest period of time. He stimulated at 175 joules per pulse, 40 Hz frequency, 10 seconds on, 10 seconds off for 20 minutes duration and followed by 60 minutes of rest, and this sequence was performed for 5 cycles in each subject. Also, in U.S. Pat. No. 7,657,310, entitled Treatment of reproductive endocrine disorders by vagus nerve stimulation, to William R. Buras, there is mention of electrical stimulation of the vagus nerve "in combination with a magnetic signal, such as transcranial magnetic stimulation (TMS)". However, that patent relates to invasive nerve stimulation and is unrelated to the treatment of bronchoconstriction, as are all the other above-mentioned magnetic stimulations of the vagus nerve.

The vagus is not the only nerve that may be stimulated non-invasively in the neck using magnetic stimulation. For example, the phrenic nerve has also been magnetically stimulated. [SIMILOWSKI, T., B. Fleury, S. Launois, H. P. Cathala, P. Bouche, and J. P. Derenne. Cervical magnetic stimulation: a new painless method for bilateral phrenic nerve stimulation in conscious humans. J. Appl. Physiol. 67(4): 1311-1318, 1989; Gerrard F. RAFFERTY, Anne Greenough, Terezia Manczur, Michael I. Polkey, M. Lou Harris, Nigel D. Heaton, Mohamed Rela, and John Moxham. Magnetic phrenic nerve stimulation to assess diaphragm function in children following liver transplantation. Pediatr Crit Care Med 2001, 2:122-126; W.D-C. MAN, J. Moxham, and M. I. Polkey. Magnetic stimulation for the measurement of respiratory and skeletal muscle function. Eur Respir J 2004; 24: 846-860].

FIG. 1 is a schematic diagram of a nerve modulating device 300 for delivering impulses of energy to nerves for the treatment of bronchial constriction or hypotension associated with anaphylactic shock, COPD or asthma. As shown, device 300 may include an impulse generator 310; a power source 320 coupled to the impulse generator 310; a control unit 330 in communication with the impulse generator 310 and coupled to the power source 320; and a magnetic stimulator coil 340 coupled via wires to impulse generator coil 310. The control unit 330 may control the impulse generator 310 for generation of a signal suitable for amelioration of the bronchial constriction or hypotension when the signal is applied to the nerve non-invasively via the magnetic stimulator coil 340. It is noted that nerve modulating device 300 may be referred to by its function as a pulse generator. U.S. Patent Application Publications 2005/0075701 and 2005/0075702, both to Shafer, both of which are incorporated herein by reference, relating to stimulation of neurons of the sympathetic nervous system to attenuate an immune response, contain descriptions of pulse generators that may be applicable to the present invention, when adapted for use with a magnetic stimulator coil.

In the preferred embodiment, the vagus nerve will be stimulated in the patient's neck, where it is situated within the carotid sheath, near the carotid artery and the interior jugular vein. The carotid sheath is located at the lateral boundary of the retropharyngeal space on each side of the neck and deep to the sternocleidomastoid muscle. The left vagus nerve is selected for stimulation because stimulation of the right vagus nerve may produce unwanted effects on the heart.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line would pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein is the preferred location for non-invasive stimulation of the vagus nerve. In the preferred embodiment, the magnetic stimulator coil would be centered on such a point, at the level of about the fifth to sixth cervical vertebra.

Signal generators for magnetic stimulators have been described for commercial systems [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006], as well as for custom designs for a control unit 330, impulse generator 310 and power source 320 [Eric BASHAM, Zhi Yang, Natalia Tchemodanov, and Wentai Liu. Magnetic Stimulation of Neural Tissue: Techniques and System Design. pp 293-352, In: Implantable Neural Prostheses 1, Devices and Applications, D. Zhou and E. Greenbaum, eds., New York: Springer (2009); U.S. Pat. No. 7,744,523, entitled Drive circuit for magnetic stimulation, to Charles M. Epstein; U.S. Pat. No. 5,718,662, entitled Apparatus for the magnetic stimulation of cells or tissue, to Reza Jalinous; U.S. Pat. No. 5,766,124, entitled Magnetic stimulator for neuro-muscular tissue, to Polson]. Magnetic nerve stimulators use a high current impulse generator 310 that may produce discharge currents of 5,000 amps or more, which is passed through the stimulator coil 340, and which thereby produces a magnetic pulse. Typically, a transformer charges a capacitor in the impulse generator 310, which also contains circuit elements that limit the effect of undesirable electrical transients. Charging of the capacitor is under the control of a control unit 330, which accepts information such as the capacitor voltage, power and other parameters set by the user, as well as from various safety interlocks within the equipment that ensure proper operation, and the capacitor is then discharged through the coil via an electronic switch (e.g., a controlled rectifier) when the user wishes to apply the stimulus.

Greater flexibility is obtained by adding to the impulse generator a bank of capacitors that can be discharged at different times. Thus, higher impulse rates may be achieved by discharging capacitors in the bank sequentially, such that recharging of capacitors is performed while other capacitors in the bank are being discharged. Furthermore, by discharging some capacitors while the discharge of other capacitors is in progress, by discharging the capacitors through resistors having variable resistance, and by controlling the polarity of the discharge, the control unit may synthesize pulse shapes that approximate an arbitrary function.

The control unit 330 also comprises a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard and computer mouse as well as externally supplied physiological signals, analog-to-digital converters for digitizing externally supplied analog signals, communication devices for the transmission and receipt of data to and from external devices such as printers and modems that comprise part of the system, hardware for generating the display of information on monitors that comprise part of the system, and busses to interconnect the above-mentioned components. Thus, the user operates the system primarily by typing instructions for the control unit 330 at a device such as a keyboard and views the results on a device such as the system's computer monitor, or directs the results to a printer, modem, and/or storage disk.

Parameters of stimulation include power level, frequency and train duration (or pulse number). The stimulation characteristics of each magnetic pulse, such as depth of penetration, strength and accuracy, depend on the rise time, peak electrical energy transferred to the coil and the spatial distribution of the field. The rise time and peak coil energy are governed by the electrical characteristics of the magnetic stimulator and stimulating coil, whereas the spatial distribution of the induced electric field depends on the coil geometry and the anatomy of the region of induced current flow. In one embodiment of the invention, pulse parameters are set in such as way as to account for the detailed anatomy surrounding the nerve that is being stimulated [Bartosz SAWICKI, Robert Szmurlo, Przemyslaw Plonecki, Jacek Starzynski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. A single pulse may be monophasic (no current reversal within the coil), biphasic or polyphasic. For rapid rate stimulators, biphasic systems are used wherein energy is recovered from each pulse in order to help energize the next. Embodiments of the invention include those that are fixed frequency, where each pulse in a train has the same inter-stimulus interval, and those that have modulated frequency, where the intervals between each pulse in a train can be varied.

Embodiments of the magnetic stimulator coil 340 include circular, parabolic, figure-of-eight (butterfly), and custom designs that are available commercially [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006]. Additional embodiments of the magnetic stimulator coil 340 have been described [U.S. Pat. No. 6,179,770, entitled Coil assemblies for magnetic stimulators, to Stephen Mould; Kent DAVEY. Magnetic Stimulation Coil and Circuit Design. IEEE Transactions on Biomedical Engineering, Vol. 47 (No. 11, November 2000): 1493-1499].

The preferred embodiment of magnetic stimulator coil 340 comprises a toroidal winding around a core consisting of high-permeability material (e.g., Supermendur), embedded in an electrically conducting medium [Rafael CARBUNARU and Dominique M. Durand. Toroidal coil models for transcutaneous magnetic stimulation of nerves. IEEE Transactions on Biomedical Engineering. 48 (No. 4, April 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999. (UMI Microform Number: 9940153, UMI Company, Ann Arbor Mich.)].

Toroidal coils with high permeability cores have been theoretically shown to greatly reduce the currents desired for transcranial (TMS) and other forms of magnetic stimulation, but only if the toroids are embedded in a conducting medium and placed against tissue with no air interface. This is difficult to do in practice because the tissue contours (head for TMS, arms, legs, neck, etc. for peripheral nerve stimulation) are not planar. To solve this problem, in the preferred embodiment of the present invention, the toroidal coil is embedded in a balloon-like structure which is filled with a conducting medium (e.g., a saline solution) with the same conductivity as muscle tissue. The container itself is made of a conducting elastomer. In other embodiments of the invention, the conducting medium may be a balloon filled with a conducting gel or conducting powders, or the balloon may be constructed extensively from deformable conducting elastomers. The balloon conforms to the skin surface removing any air, thus allowing for high impedance matching and conduction of large electric fields in to the tissue. A device such as that disclosed in U.S. Pat. No. 7,591,776, entitled Magnetic stimulators and stimulating coils, to Phillips et al. may conform the coil itself to the contours of the body, but in the preferred embodiment, such a curved coil is also enclosed by a container that is filled with a conducting medium.

The container of electrically conducting medium is identified as 350 in FIG. 1. As shown there, the container of electrically conducting medium 350 not only encloses the magnetic stimulator coil, but in the preferred embodiment is also deformable such that it is form-fitting when applied to the surface of the body. Thus, the sinuousness or curvature shown at the outer surface of the container of electrically conducting medium 350 correspond also to sinuousness or curvature on the surface of the body, against which the container 350 is applied so as to make the container and body surface contiguous. Use of the container of conducting medium 350 allows one to generate (induce) electric fields in tissue (and electric field gradients and electric currents) that are equivalent to those generated using current magnetic stimulation devices, but with 1/10 to 1/1000 of the current applied to the magnetic coil. This allows for minimal heating and deeper tissue stimulation.

The design and methods of use of impulse generators, control units, and stimulator coils for magnetic stimulators are informed by the designs and methods of use of impulse generators, control units, and electrodes (with leads) for comparable completely electrical nerve stimulators, but design and methods of use of the magnetic stimulators can take into account many special considerations, making it generally not straightforward to transfer knowledge of completely electrical stimulation methods to magnetic stimulation methods. Such considerations include determining the anatomical location of the stimulation and determining the appropriate pulse configuration [OLNEY R K, So Y T, Goodin D S, Aminoff M J. A comparison of magnetic and electric stimulation of peripheral nerves. Muscle Nerve 1990:13:957-963; J. NILSSON, M. Panizza, B. J. Roth et al. Determining the site of stimulation during magnetic stimulation of the peripheral nerve, Electroencephalographs and clinical neurophysiology. vol 85, pp. 253-264, 1992; Nafia AL-MUTAWALY, Hubert de Bruin, and Gary Hasey. The Effects of Pulse Configuration on Magnetic Stimulation. Journal of Clinical Neurophysiology 20(5):361-370, 2003].

Furthermore, a potential practical disadvantage of using magnetic stimulator coils is that they may overheat when used over an extended period of time. Use of the above-mentioned toroidal coil and container of electrically conducting medium addresses this potential disadvantage. However, because of the poor coupling between the stimulating coils and the nerve tissue, large currents are nevertheless desired to reach threshold electric fields. At high repetition rates, these currents can heat the coils to unacceptable levels in seconds to minutes depending on the power levels and pulse durations and rates. Two approaches to overcome heating are to cool the coils with flowing water or air or to increase the magnetic fields using ferrite cores (thus allowing smaller currents). For some applications where relatively long treatment times at high stimulation frequencies may be desired, e.g. treating acute asthma attacks by stimulating the vagus nerve, neither of these two approaches are adequate. Water-cooled coils overheat in a few minutes. Ferrite core coils heat more slowly due to the lower currents and heat capacity of the ferrite core, but also cool off more slowly and do not allow for water-cooling since the ferrite core takes up the volume where the cooling water would flow.

A solution to this problem is to use a fluid which contains ferromagnetic particles in suspension like a ferrofluid, or magnetorheological fluid as the cooling material. Ferrofluids are colloidal mixtures composed of nanoscale ferromagnetic, or ferrimagnetic, particles suspended in a carrier fluid, usually an organic solvent or water. The ferromagnetic nanoparticles are coated with a surfactant to prevent their agglomeration (due to van der Waals forces and magnetic forces). Ferrofluids have a higher heat capacity than water and will thus act as better coolants. In addition, the fluid will act as a ferrite core to increase the magnetic field strength. Also, since ferrofluids are paramagnetic, they obey Curie's law, and thus become less magnetic at higher temperatures. The strong magnetic field created by the magnetic stimulator coil will attract cold ferrofluid more than hot ferrofluid thus forcing the heated ferrofluid away from the coil. Thus, cooling may not require pumping of the ferrofluid through the coil, but only a simple convective system for cooling. This is an efficient cooling method which may require no additional energy input [U.S. Pat. No. 7,396,326 and published applications US2008/0114199, US2008/0177128, and US2008/0224808, all entitled Ferrofluid cooling and acoustical noise reduction in magnetic stimulators, respectively to Ghiron et al., Riehl et al., Riehl et al. and Ghiron et al.].

Magnetorheological fluids are similar to ferrofluids but contain larger magnetic particles which have multiple magnetic domains rather than the single domains of ferrofluids. [U.S. Pat. No. 6,743,371, Magneto sensitive fluid composition and a process for preparation thereof, to John et al.]. They can have a significantly higher magnetic permeability than ferrofluids and a higher volume fraction of iron to carrier. Combinations of magnetorheological and ferrofluids may also be used [M T LOPEZ-LOPEZ, P Kuzhir, S Lacis, G Bossis, F Gonzalez-Caballero and J D G Duran. Magnetorheology for suspensions of solid particles dispersed in ferrofluids. J. Phys.: Condens. Matter 18 (2006) S2803-S2813; Ladislau VEKAS. Ferrofluids and Magnetorheological Fluids. Advances in Science and Technology Vol. 54 (2008) pp 127-136.]. Accordingly, in the preferred embodiment, overheating is minimized by cooling the magnetic stimulator coil 340 with a ferrofluid and/or magnetorheological fluid and/or a mixture or combination of ferrofluid and magnetorheological fluids.

In the preferred embodiment, overheating of the magnetic stimulator coil 340 may also be minimized by optionally restricting the magnetic stimulation to particular phases of the respiratory cycle, allowing the coil to cool during the other phases of the respiratory cycle. Alternatively, greater peak power may be achieved per respiratory cycle by concentrating all the energy of the magnetic pulses into selected phases of the respiratory cycle. Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. After digitizing such signals, the phase of respiration may be determined using open source software such as the one called "puka", which is part of PhysioToolkit, a large published library of open source software and user manuals that are used to process and display a wide range of physiological signals [GOLDBERGER A L, Amaral L A N, Glass L, Hausdorff J M, Ivanov P Ch, Mark R G, Mietus J E, Moody G B, Peng C K, Stanley H E. PhysioBank, PhysioToolkit, and PhysioNet: Components of a New Research Resource for Complex Physiologic Signals. Circulation 101(23):e215-e220 (2000); available from PhysioNet, M.I.T. Room E25-505A, 77 Massachusetts Avenue, Cambridge, Mass. 02139]. In one embodiment of the present invention, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning-points, based upon the frequency with which waveforms from previous breaths match a partial waveform for the current breath. The control unit 330 then controls the impulse generator 310 to stimulate the selected nerve only during a selected phase of respiration, such as all of inspiration or only the first second of inspiration, or only the expected middle half of inspiration.

In the preferred embodiment, physiological signals in addition to those related to the determination of respiratory phase are measured non-invasively. The additional signals comprise the electrocardiogram, measured by one or more chest electrocardiographic leads; the arterial blood pressure measured non-invasively and continuously with an arterial tonometer applied to patient's wrist; and a pulse oximeter applied to the patient's fingertip. The electrocardiographic electrodes may also be used to measure transthoracic impedance, so as to obtain a signal that rises and falls according to the phase of respiration. A respiration signal may also be obtained from the actual electrocardiographic signal, using computer programs available in the PhysioToolkit software library that was mentioned above. In embodiments of the present invention, the control unit 330 contains analog-to-digital converters to receive such analog physiological signals, and software for the analysis of the signal waveforms resides within the control unit 330. In particular, the heart rate is derived from the electrocardiographic signals using open source software such as the QRS detectors and heart rate tachometers that are available in the PhysioToolkit software library, and the systolic, diastolic, and mean blood pressure are derived from the blood pressure waveform using software for pulse detection that is also available in the PhysioToolkit software library.

In our experiments that were summarized above (and will be described in detail below), the location and parameters of the electrical impulses delivered to the vagus nerve were optimized to stimulate the release of hormones into the circulation, at concentrations that produce bronchial smooth muscle relaxation, and that also have little effect on heart rate or blood pressure. For bronchoconstricted patients with normal heart rates and blood pressure, those are the stimulation location and parameters of choice. However, during asthma or COPD attacks or anaphylactic shock, it is sometimes the case that a significant increase or decrease in heart rate accompanies airway constriction. In cases of unsafe or suboptimal heart rates, the teachings of the present invention permit not only prompt airway dilation, but also an improved heart rate, to enable subsequent life saving measures that otherwise would be ineffective or impossible due to severe constriction or other physiological effects. Treatment in accordance with the present invention provides not only bronchodilation, but also optionally improved heart function for a long enough period of time that administered medication such as epinephrine has time to take effect before the patient suffocates. This is because, depending on the placement of the impulse to the selected nerve fiber, the stimulating, blocking and/or modulating signal can also improve the heart function, by potentially elevating or decreasing heart rate. Furthermore, as an option in the present invention, parameters of the stimulation may be modulated by the control unit 330 to control the impulse generator 310 in such a way as to temporally modulate stimulation by the magnetic stimulator coil 340, in such a way as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention, and as described above, the control unit 330 extracts the systolic, diastolic, and mean arterial blood pressure from the blood pressure waveform. The control unit 330 will then control the impulse generator 310 in such a way as to temporally modulate nerve stimulation by the magnetic stimulator coil 340, in such a way as to achieve and maintain the blood pressure within predetermined safe or desired limits, by the same method that was indicated above for the heart rate. Thus, even if one does not intend to treat bronchoconstriction, embodiments of the invention described above may be used to achieve and maintain the heart rate and blood pressure within desired ranges.

If one does not anticipate problems with overheating the magnetic stimulator coil 340, it may nevertheless be therapeutically advantageous to program the control unit 330 to control the impulse generator 310 in such a way as to temporally modulate stimulation by the magnetic stimulator coil 340, depending on the phase of the patient's respiration. In patent application JP2008/081479A, entitled Vagus nerve stimulation system, to Yoshihoto, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to the problem of bronchoconstriction that is addressed herein, but it does consider stimulation during particular phases of the respiratory cycle, for the following reason. Because the vagus nerve is near the phrenic nerve, Yoshihoto indicates that the phrenic nerve will sometimes be electrically stimulated along with the vagus nerve. The present applicants did not experience this problem in the experiments reported below, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual. Patent application publication US2009/0177252, entitled Synchronization of vagus nerve stimulation with the cardiac cycle of a patient, to Arthur D. Craig, discloses a method of treating a medical condition in which the vagus nerve is stimulated during a portion of the cardiac cycle and the respiratory cycle. That disclosure pertains to the treatment of a generic medical condition, so it is not specifically directed to the treatment of bronchoconstriction. In the present application, stimulation of selected nerve fibers during particular phases of respiration for the treatment of bronchoconstriction may be motivated by two physiological considerations. The first is that contraction of bronchial smooth muscle appears to be intrinsically rhythmic. It has been reported that bronchial smooth muscle contracts over two phases, during mid-inspiration and early expiration. When the vagus efferent nerves are repetitively stimulated with electric pulses, the bronchus constricted periodically; tonic constriction is almost absent in the bronchus in response to the vagally mediated descending commands. [KONDO, Tetsuri, Ichiro Kobayashi, Naoki Hayama, Gen Tazaki, and Yasuyo Ohta. Respiratory-related bronchial rhythmic constrictions in the dog with extracorporeal circulation. J Appl Physiol 88: 2031-2036, 2000]. Accordingly, a rationale for stimulating the vagus nerve during particular phases of the respiratory cycle is that such stimulation may be used to counteract or inhibit the constriction that occurs naturally during those specific phases of respiration. If the counteracting or inhibiting effects occur only after a delay, then the timing of the stimulation pulses should precede the phases of respiration during which the contraction would occur, by an interval corresponding to the delay. A second motivation for stimulating the vagus nerve during particular phases of respiration is that an increase or decrease in the duration of subsequent phases of respiration may be produced by applying the stimulation during particular phases of respiration [M. SAMMON, J. R. Romaniuk and E. N. Bruce. Bifurcations of the respiratory pattern produced with phasic vagal stimulation in the rat. J Appl Physiol 75: 912-926, 1993]. In particular, a narrow window may exist at the expiratory-inspiratory transition in which it may be possible to induce bursts of inspiratory activity followed by a prolonged breath. Accordingly, if it is therapeutically beneficial to induce deep breaths, those breaths might be induced by stimulating during that time-window. In fact, the physiologically meaningful cycle of stimulation in this case is not a single respiratory cycle, but is instead a collective sequence of respiratory cycles, wherein it makes sense only to speak of stimulation during particular parts of the sequence.

In some embodiments of the invention, it may also be therapeutically advantageous to program the control unit 330 to control the impulse generator 310 in such a way as to modulate stimulation by the magnetic stimulator coil 340, by modulating the parameters and properties of the applied impulses, depending on the values of frequently measured non-invasive indicators of the magnitude of bronchoconstriction. Because of patient motion, e.g., due to the patient's fidgeting restlessness or contraction of the sternocleidomastoid muscle, there will inevitably be some motion of the magnetic stimulator coil 340 relative to the location of the nerve fibers that are selected for stimulation, no matter how rigidly the coil 340 and conducting container 350 are comfortably held against the patient, using a frame and strap similar to those used for transcranial magnetic stimulation. Therefore, the power of the energy impulse delivered to the selected nerve fibers would fluctuate or drift as a function of the fluctuating or drifting distance and angles between the coil and nerve fiber, unless a method is employed to automatically adjust the power of the energy impulse for such fluctuations or drift. In the preferred embodiment, that method makes the adjustment by measuring a surrogate for $FEV_1$ and then adjusting the power in such a way that the value of the surrogate measurement does not decrease relative to the surrogate's previous value averaged over a predetermined number of prior cycles of respiration. It is understood that the power adjustment may also occur throughout a single respiratory cycle, particularly when there is movement due to changing accessory muscle use. Thus, in one embodiment of the present invention, the control unit 330 contains an analog-to-digital converter to receive an analog signal that is a surrogate for $FEV_1$, or it contains a digital interface to receive a digital signal that is a surrogate for $FEV_1$, and software for the analysis of the digitized $FEV_1$ surrogate data resides within the control unit 330. The control unit 330 then sets parameters of the impulse generation (such as power) to control the impulse generator 310 so as to maintain or move the surrogate $FEV_1$ value to within a desired range, using the same method that was described above for the heart rate and blood pressure. It should be noted also that the patient him/herself may sense an improvement in breathing even before there is a clear improvement in $FEV_1$ or its surrogates, in which case, verbal communication between patient and medical provider may be used for feedback. Accordingly, it is understood that the medical provider may override the automatic feedback and use the verbal feedback of the patient to manually adjust stimulation parameters.

Three types of non-invasive measurements are currently recognized as being surrogates for the measurement of $FEV_1$: pulsus paradoxus, accessory muscle use, and airway resistance. In the preferred embodiment, pulsus paraduxus is measured, which is based on the observation that in asthmatic patients (as well as other patients experiencing bronchoconstriction), the patient's blood pressure waveform will rise and fall as a function of the phase of respiration. In the preferred embodiment, the blood pressure waveform (and the magnitude of any accompanying pulsus paradoxus) is measured non-invasively with an arterial tonometer, that is placed, for example, on the patient's wrist [James RAYNER, Flor Trespalacios, Jason Machan, Vijaya Potluri, George Brown, Linda M. Quattrucci, and Gregory D. Jay. Continuous Noninvasive Measurement of Pulsus Paradoxus Complements Medical Decision Making in Assessment of Acute Asthma Severity. CHEST 2006; 130:754-765]. Digitization and analysis of the blood pressure waveform may be performed in a computer dedicated to that purpose, in which case, the numerical value of the continuously varying pulsus paradoxus signal would be transferred to the control unit 330 through a digital interface connecting the control unit 330 and dedicated computer. Alternatively, the control unit 330 may contain an analog-to-digital converter to receive the analog tonometric signal, and the analysis of the blood pressure waveform would be performed within the control unit 330. Instead of using an arterial tonometer to measure the blood pressure wave form and any accompanying pulsus paradoxus, it is also possible to use a pulse oximeter, attached for example, to the patient's finger tip [Donald H ARNOLD, Cathy A Jenkins, Tina V Hartert. Noninvasive assessment of asthma severity using pulse oximeter plethysmograph estimate of pulsus paradoxus physiology. BMC Pulmonary Medicine 2010, 10:17; U.S. Pat. Nos. 7,044,917 and 6,869,402, entitled Method and apparatus for measuring pulsus paradoxus, to Arnold]. A dedicated computer may be used to acquire and analyze the blood pressure waveform and the magnitude of pulsus paradoxus, which would be transferred to the control unit 330 as indicated above for the tonometrically acquired signal, or the analog pulse oximetry signal may be digitized and processed within the control unit 330, as indicated above.

Accessory muscle use may also be used as a surrogate for the measurement of $FEV_1$ [ARNOLD D H, Gebretsadik T, Minton P A, Higgins S, Hartert T V: Clinical measures associated with FEV1 in persons with asthma requiring hospital admission. Am J Emerg Med 2007, 25:425-429]. The accessory muscles are not used during restful, tidal breathing of a normal patient, but are used during labored breathing. The sternocleidomastoid muscles are the most important accessory muscles of inspiration. They run from the mastoid processes to insert along the medial third of the clavicle. To measure their use, a standard electromyogram may be performed, the signal from which may be digitized and transferred to the control unit 330 as indicated above. [T. DE MAYO, R. Miralles, D. Barrero, A. Bulboa, D. Carvajal, S. Valenzuela, and G. Ormeno. Breathing type and body position effects on sternocleidomastoid and suprahyoid EMG activity. Journal of Oral Rehabilitation, Volume 32, Issue 7, pages 487-494, July 2005; Roberto MERLETTI, Alberto Botter, Amedeo Troiano, Enrico Merlo, Marco Alessandro Minetto. Technology and instrumentation for detection and conditioning of the surface electromyographic signal: State of the art. Clinical Biomechanics 24 (2009) 122-134]. Alternatively, non-invasive plethysmography may be used to measure accessory muscle use, because as ventilatory demands increase, these muscles contract to lift the sternum and increase the anteroposterior diameter of the upper rib cage during inspiration. The anteroposterior diameter may be measured, for example, by respiratory inductance plethysmography (RIP) and electrical impedance tomography (EIT). RIP uses elastic bands around the chest (and abdomen) to assess changes in lung volume. EIT measures regional impedance changes with electrodes around the patient's chest, each of them injecting and receiving small currents. Such impedance changes have been correlated with dimensional changes of the lung. The plethysmography signal may be digitized and transferred to the control unit 330 as indicated above, as a measure of the extent to which rib cage geometry is changing as the result of accessory muscle use.

Another surrogate for the measurement of $FEV_1$ is the measurement of airway resistance [P. D. BRIDGE, H. Lee, M. Silverman. A portable device based on the interrupter technique to measure bronchodilator response in schoolchildren. Eur Respir J, 1996, 9, 1368-1373]. Airway resistance is defined as the ratio of the difference between mean alveolar pressure and airway opening pressure to flow measured at the mouth, and it may be measured using devices that are commercially available [e.g., MicroRint, Catalog No. MR5000 from Micromedical Ltd. and Cardinal Health UK 232 Ltd, The Crescent, Jays Close, Basingstoke, RG22 4BS, U.K.]. Such devices have a serial or USB port that permits the control unit 330 to instruct the device to perform the airway resistance measurement and receive the airway resistance data in return, via a serial or USB port in the control unit 330. Because the measurement is intermittent rather than continuous, and because it prefers the patient to breathe passively through a mouthpiece or face mask, this surrogate for the measurement of FEV1 is not the preferred one.

Figure 2:
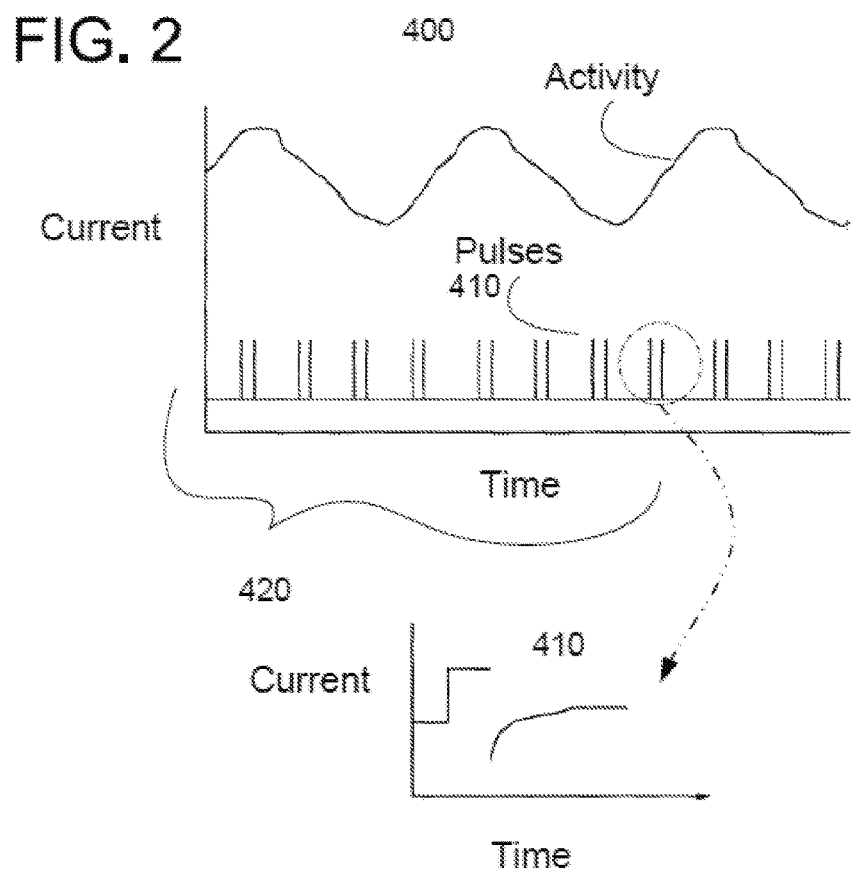
FIG. 2 illustrates an exemplary electrical voltage/current profile for a blocking and/or modulating impulse applied to a portion or portions of a nerve in accordance with an embodiment of the present invention.

FIG. 2 illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively induced within the patient by the magnetic stimulator. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the electrode(s) 340 that deliver the stimulating, blocking and/or modulating impulse 410 to the nerve. Nerve modulating device 300 may be externally powered and/or recharged may have its own power source 320. By way of example, device 300 may be purchased commercially.

The parameters of the modulation signal 400 are preferably programmable, such as the frequency, amplitude, duty cycle, pulse width, pulse shape, etc. An external communication device may modify the pulse generator programming to improve treatment.

In addition, or as an alternative to the devices to implement the modulation unit for producing the electrical voltage/current profile of the stimulating, blocking and/or modulating impulse to the magnetic stimulator coil, the device disclosed in U.S. Patent Publication No.: 2005/0216062 (the entire disclosure of which is incorporated herein by reference), may be employed. U.S. Patent Publication No.: 2005/0216062 discloses a multifunctional electrical stimulation (ES) system adapted to yield output signals for effecting electromagnetic or other forms of electrical stimulation for a broad spectrum of different biological and biomedical applications, including magnetic stimulators, which produce a high intensity magnetic field pulse in order to non-invasively stimulate nerves. The system includes an ES signal stage having a selector coupled to a plurality of different signal generators, each producing a signal having a distinct shape such as a sine, a square or a saw-tooth wave, or simple or complex pulse, the parameters of which are adjustable in regard to amplitude, duration, repetition rate and other variables. Examples of the signals that may be generated by such a system are described in a publication by Liboff [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated. As described above, one aspect of the present invention is that such feedback is provided by non-invasive sensors producing signals that may act as surrogates for the measurement of $FEV_1$.

The use of feedback to generate the modulation signal 400 may result in a signal that is not periodic, particularly if the feedback is produced from sensors that measure naturally occurring, time-varying aperiodic physiological signals from the patient. In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance. In normal respiratory physiology, sighing at irregular intervals is thought to bring about such a resetting of the respiratory control system. Experimentally, noisy artificial ventilation may increase respiration [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41]. So, in one embodiment of the present invention, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

The stimulation device 300, magnetic stimulation coil 340, and electrically conducting container 350 are preferably selected and configured to induce a peak pulse voltage in the range from about 0.2 volts to about 20 volts, at or between points in close proximity to the nerve fibers that are being stimulated.

The stimulating, blocking and/or modulating impulse signal 410 preferably has a frequency, an amplitude, a duty cycle, a pulse width, a pulse shape, etc. selected to influence the therapeutic result, namely stimulating, blocking and/or modulating some or all of the transmission of the selected nerve. For example the frequency may be about 1 Hz or greater, such as between about 15 Hz to 50 Hz, more preferably around 25 Hz. The modulation signal may have a pulse width selected to influence the therapeutic result, such as about 20 microseconds or greater, such as about 20 microseconds to about 1000 microseconds. The modulation signal may have a peak voltage amplitude selected to influence the therapeutic result, such as about 0.2 volts or greater, such as about 0.2 volts to about 20 volts.

In a preferred embodiment of the invention, a method of treating bronchial constriction comprises applying one or more electrical impulse(s) of a frequency of about 15 Hz to 50 Hz to a selected region of the vagus nerve to reduce a magnitude of constriction of bronchial smooth muscle. As discussed in more detail below, applicant has made the unexpected discovered that applying an electrical impulse to a selected region of the vagus nerve within this particular frequency range results in almost immediate and significant improvement in bronchodilation, as discussed in further detail below. Applicant has further discovered that applying electrical impulses outside of the selected frequency range (15 Hz to 50 Hz) does not result in immediate and significant improvement in bronchodilation. Preferably, the frequency is about 25 Hz. In this embodiment, the induced electrical impulse(s) are of an amplitude of between about 0.75 to 12 volts and have a pulsed on-time of between about 50 to 500 microseconds, preferably about 200-400 microseconds.

In accordance with another embodiment, devices in accordance with the present invention are provided in a "pacemaker" type form, in which electrical impulses 410 are generated to a selected region of the nerve by device 300 on an intermittent basis to create in the patient a lower reactivity of the nerve to upregulation signals.

In an alternate embodiment, a mechanical vibrator transmits energy to a nerve, rather than a magnetic stimulator. In 1932, Hill demonstrated that the human vagus nerve in the neck may be excited in some individuals by purely mechanical means [Ian G. W. HILL. Stimulation of the vagus nerve and carotid sinus in man. Experimental Physiology (1932) 22, 79-93]. That demonstration took place during invasive surgical interventions, and the mechanical stimulation involved only manual percussion pressure. His investigations were motivated by the fact that the vagus nerve may be stimulated by carotid massage on the neck near the carotid body (as well as by Valsalva maneuver, ocular pressure, digital rectal massage, and head-up tilting), which is performed in order to investigate causes of syncope or to treat supraventricular tachycardia. Cardioinhibitory responses may result from the massage (decreased heart rate and heart contractility, due to enhanced parasympathetic tone), as well as a drop in blood pressure (due to vasodilation of blood vessels in the legs, probably due to a decrease in sympathetic nervous system tone). Although carotid massage is known to dilate blood vessels in the legs, it is not known to do so in the bronchi and is therefore not used to produce bronchodilation. Subsequent investigators demonstrated that the vagus nerve may be stimulated mechanically at a location where it leaves the brainstem [Vladimir SHUSTERMAN, Peter J. Jannetta, Benhur Aysin, Anna Beigel, Maksim Glukhovskoy, and Irmute Usiene. Direct Mechanical Stimulation of Brainstem Modulates Cardiac Rhythm and Repolarization in Humans. Journal of Electrocardiology Vol. 35 Supplement 2002, pp. 247-256]. That mechanical stimulation also took place during invasive surgery, and the stimulation occurred at 1 to 2 Hertz with a duration of 1 minute. Afferent nerves carried by the auricular branch of the vagus nerve (also known as Arnold nerve and Alderman's nerve) also innervate the external auditory meatus. When mechanically stimulated, in some individuals they may elicit the Arnold's ear-cough reflex that is similar to a reflex that may be elicited by stimulating other branches of the vagus nerve.

[TEKDEMIR I, Aslan A, Elhan A. A clinico-anatomic study of the auricular branch of the vagus nerve and Arnold's ear-cough reflex. Surg Radiol Anat 1998; 20:253-257].

Non-invasive mechanical stimulation of the vagus nerve at the ear is disclosed in patent application US2008/0249439, entitled Treatment of Inflammation by Non-Invasive Stimulation, to Tracey et al., which is directed to stimulating a subject's inflammatory reflex in a manner that significantly reduces proinflammatory cytokines in the subject. To achieve that effect, Tracey et al. disclosed that an effective mechanical stimulation frequency is between about 50 and 500 Hz. They claim their method for treatment of a long list of diseases, including allergy, anaphylactic shock, bronchitis, emphysema, and adult respiratory distress syndrome. However, they make no mention of bronchial constriction or bronchodilation. They also say that the effect that their method has on smooth muscle cells (among many other cell types in a list) is to modulate their production of proinflammatory cytokines, but their application makes no mention of their method modulating the contractile properties of smooth muscle cells. Thus, if the non-invasive method that they disclose is useful for the treatment of asthma, anaphylactic shock, or chronic obstructive pulmonary disease, there is no motivation or suggestion that such usefulness would be related to relaxation of the bronchial smooth muscle. In fact, in a review article concerning the inflammatory reflex [Kevin J. TRACEY. The inflammatory reflex. NATURE Vol. 420 (19/26 Dec. 2002) 853-859], the author of the review article and co-applicant for patent application US2008/0249439, Kevin J. Tracey, makes no mention of bronchoconstriction, and he only refers to smooth muscle implicitly in reference to the smooth muscle of arterioles, when he states that stimulation of the vagus nerve to dilate arterioles is distinct from stimulation of the vagus nerve to inhibit the inflammatory reflex. Thus, in that review, Tracey writes (p. 585): "Stimulation of efferent vagus nerve activity has been associated classically with slowing heart rate, induction of gastric motility, dilation of arterioles and constriction of pupils. Inhibition of the inflammatory response can now be added to this list."

U.S. Pat. No. 4,966,164, entitled Combined sound generating device and electrical acupuncture device and method for using the same, to Colsen et al., discloses sound/electroacupuncture that also stimulates the ear mechanically, using a buzzer operating in the range of 0.5 to 20 Hz. However, the buzzer is provided in order to provide auditory stimulation, rather than the stimulation of acupuncture meridian points. Furthermore, the disclosure by Colsen et al. does not mention use of their invention to treat bronchoconstriction. Of note is the fact that U.S. Pat. No. 4,966,164 discloses stimulation in the ear with mechanical frequencies in the range 0.5 to 20 Hz, and the aforementioned application US2008/0249439 discloses stimulation in the ear with mechanical frequencies in range of between 50 and 500 Hz, but neither discloses the use of mechanical vibrations in the intervening range of greater than 20 Hz and less than 50 Hz.

Figure 3:
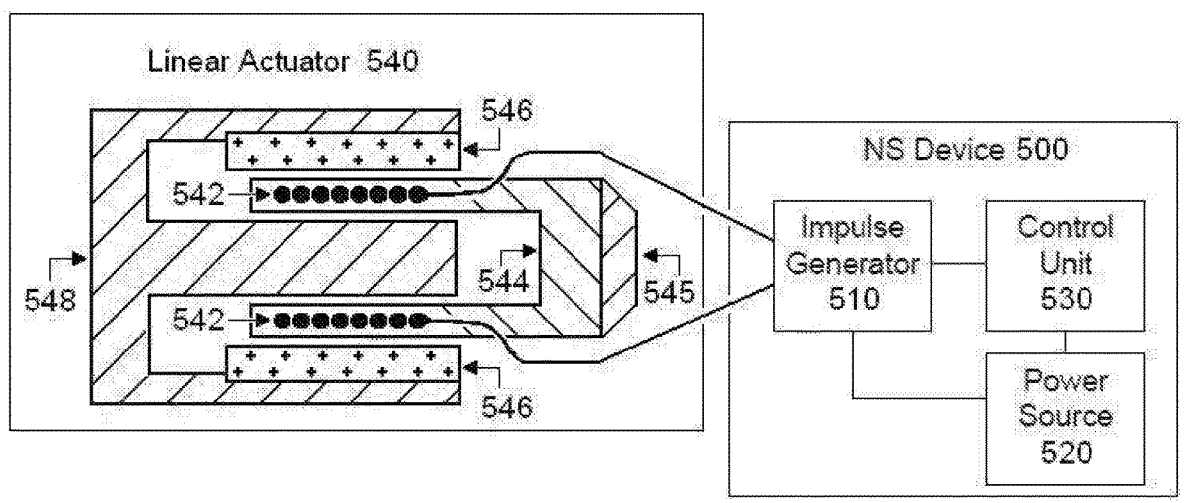
FIG. 3 is a schematic view of an alternate embodiment of a nerve modulating device according to the present invention, which supplies controlled pulses of electrical current to a linear actuator that is used as a mechanical vibrator.

FIG. 3 illustrates an alternate embodiment of the invention, in which a mechanical vibrator transmits energy to a nerve. The figure contains a schematic diagram of a nerve modulating device 500 for delivering impulses of mechanical energy to nerves for the treatment of bronchial constriction or hypotension associated with anaphylactic shock, COPD or asthma. As shown, device 500 may include an impulse generator 510; a power source 520 coupled to the impulse generator 510; a control unit 530 in communication with the impulse generator 510 and coupled to the power source 520; and a linear actuator 540 coupled via wires to the impulse generator coil 510. The control unit 530 may control the impulse generator 510 for generation of a signal suitable for amelioration of the bronchial constriction or hypotension, when mechanical vibrations are applied to the nerve non-invasively using a linear actuator 540.

It is noted that nerve modulating device 500 may be referred to by its function as a pulse generator. U.S. Patent Application Publications 2005/0075701 and 2005/0075702, both to Shafer, both of which are incorporated herein by reference, relating to stimulation of neurons of the sympathetic nervous system to attenuate an immune response, contain descriptions of pulse generators that may be applicable to the present invention, when adapted to drive a mechanical vibrator.

In the preferred embodiment, mechanical vibrations are produced by a linear actuator 540 as shown in FIG. 3 [BOLDEA, I. and Nasar, S. A. Linear electric actuators and generators. IEEE Transactions on Energy Conversion. Vol. 14 Issue: 3 (September 1999): 712-717; Bill BLACK, Mike Lopez, and Anthony Marcos. Basics of voice coil actuators. Power Conversion and Intelligent Motion (PCIM) July 1993: 44-46]. In alternate embodiments, vibrations that are applied to the nerve may be produced by any device that is known in the art to be capable of generating appropriate mechanical vibration, including (but not limited to): an electromagnet, a bimorph, a piezo crystal, an electrostatic actuator, a speaker coil, and a rotating magnet or mass. Ultrasound may also be used to produce vibrations at frequencies lower than ultrasonic frequencies [U.S. Pat. No. 5,903,516, entitled Acoustic force generator for detection, imaging and information transmission using the beat signal of multiple intersecting sonic beams, to Greenleaf et al.; U.S. Pat. No. 7,753,847, entitled Ultrasound vibrometry, to Greenleaf et al.; U.S. Pat. No. 7,699,768, entitled Device and method for non-invasive, localized neural stimulation utilizing hall effect phenomenon, to Kishawi]. In some embodiments, mechanical vibration is delivered non-invasively using devices like those that are applied to the skin to reduce pain (vibratory analgesia) [Elizabeth A. ROY, Mark Hollins, William Maixner. Reduction of TMD pain by high-frequency vibration: a spatial and temporal analysis. Pain 101 (2003) 267-274; Kevin C SMITH, Stephen L Comite, Suprina Balasubramanian, Alan Carver and Judy F Liu. Vibration anesthesia: A noninvasive method of reducing discomfort prior to dermatologic procedures. Dermatology Online Journal 10 (2): 1 (2004).]. Multiple sources of vibration may also be used and applied at one or more locations on the surface of the body.

The linear actuator 540 shown in FIG. 3 comprises two separable parts: a coil holder that is PI (Π)-shaped in cross-section (544), and a magnet-holder that is E-shaped in cross-section (548). The coil holder 544 is a cylinder (shown in FIG. 3 as legs of the Π in cross section) that is open on one end and typically closed on the other end. The closed part is shown in FIG. 3 as the middle member connecting the legs of the Π in cross section. A coil of wire 542 is wrapped around or embedded within the cylindrical part of the coil holder. The coil 542 is shown in cross section in FIG. 3 as a series of blackened circles along both legs of the Π. A pair of lead wires emerge from the coil 542 and then from the coil holder 544. They are attached to the impulse generator 510, such that electrical current may pass into one of the lead wires, through the coil, and out the other lead wire.

Air-gaps separate the coil holder 544 from magnet-holder 548, so that the two parts may slide relative to one another. The outside part of the magnet holder 584 is cylindrical (shown in cross section in FIG. 3 as the top and bottom horizontal lines of an E), and permanent magnets 546 are embedded on the inside diameter of that outer cylinder, such that the magnets facing the coil 542 across an air gap are all of the same polarity. In the preferred embodiment, the magnets are made of rare-earth materials. The outer cylinder is ferromagnetic, and an inner core of ferromagnetic material is attached to it (shown in cross section in FIG. 3 as the middle horizontal line of an E, attached to the outer cylinder of the magnet holder by the vertical line of an E). The magnetic field generated by the permanent magnets 546 is oriented radially, and the ferromagnetic components of the magnet holder complete the magnetic circuit. A Lorentz force is generated axially on the coil (and coil holder), whenever current is passed through the coil, which will be proportional to the current multiplied by the magnetic flux density produced by the magnets. Therefore, when the impulse generator 510 produces pulses of current in the coil that alternate in sign, the coil holder will move alternately in opposite directions along its axis, i.e., vibrate. The frequency and amplitude of that mechanical vibration are therefore determined by the frequency and amplitude of current pulses that are generated by the impulse generator 510.

An actuator-tip 545 is attached to the closed part of the coil holder 544. The linear actuator is placed into physical contact with the surface of the patient's body on the outer surface of the actuator-tip, which is opposite to the surface of the actuator-tip that is connected to the coil holder. A stationary surround is used to limit the spread of vibration across the skin, as follows: a stationary ring is attached, by an adjustable metal arm, to a table that is mechanically isolated from the vibratory stimulator. The heavy ring (deformable metal, covered by a thermal insulator) is positioned onto the patient around the area on the surface of the skin that is vibrated by the actuator tip, thereby limiting vibration across the skin. The shape of the actuator-tip surface that contacts the patient need not be circular, and need not even lie in a plane, but may instead be selected to have some other shape such as rectangular or hemi-spherical or even threaded for attachment to another piece. The actuator-tip is preferably detachable so as to accommodate different tip shapes for different applications. In the preferred embodiment of the invention, the actuator tip will be rectangular with a dimension of approximately 5 mm by 40 mm, with rounded edges so as to press comfortably against a patient's neck above the vagus nerve, as now described. Consider the plane of the skin on the neck to define an X-Y axis, where the X axis is vertical and the Y axis is horizontal for a standing patient. A Z axis is perpendicular to the X-Y axis, so that if the actuator tip is straight, and the actuator is positioned parallel to the Z axis (perpendicular to the skin of the neck), vibrations will push the skin in the Z axis, perpendicular to the plane of the skin of the neck. In another embodiment, the actuator tip is L shaped, and the actuator is positioned parallel to the X-Y axis. When the actuator tip is then pressed against the skin, it will vibrate the skin within the X-Y plane. As the actuator is rotated about the point of skin-tip contact, it will vibrate the skin in the direction of the X axis, the Y axis, and intermediate angles within the X-Y plane. In the preferred embodiment, vibration is in the Z axis, perpendicular to the skin of the neck.

Proceeding from the skin of the neck above the sternocleidomastoid muscle to the vagus nerve, a line would pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein is the preferred location for non-invasive stimulation of the vagus nerve. In the preferred embodiment, the mechanical vibrator would be centered on such a point, at the level of about the fifth to sixth cervical vertebra. For a rectangular actuator-tip, the long sides of the rectangle will be placed parallel to the route of the vagus nerve in the neck. Typically, the location of the carotid sheath or jugular veins in a patient (and therefore the location of the vagus nerve) will be ascertained in any manner known in the art, e.g., by feel or ultrasound imaging.

Considering that the nerve stimulating device 300 in FIG. 1 and the nerve stimulating device 500 in FIG. 3 both control electrical currents within a coil of wire, their functions are analogous, except that one stimulates nerves via the pulse of a magnetic field, and the other stimulates nerves via a pulse of vibration. Accordingly, the features recited for the nerve stimulating device 300, such as its use for feedback involving $FEV_1$ surrogates, control of the heart rate and blood pressure, stimulation during selected phases of the respiratory cycle, and preferred frequency of stimulation, apply as well to the nerve stimulating device 500 and will not be repeated here. The preferred parameters for each nerve stimulating device are those that produce the effects described below in connection with the detailed description our experiments.

In another embodiment of the invention, a selected nerve is stimulated by delivering to it impulses of light and/or heat energy. Because absorption and scattering of light increases exponentially with depth, little irradiated light at wavelengths below 800 nm can traverse pale human skin, which has a thickness that varies from 1 to 3 mm depending upon location. At wavelengths above 1,400 nm, there is also almost no light transmission because of water absorption. Therefore, infrared wavelengths are ordinarily preferred to irradiate the skin surface, which can penetrate up to about 4 to 5 millimeters. To stimulate a nerve non-invasively with light, the nerve should therefore lie very near the surface of the skin (e.g., vagus nerve at the ear), and infrared light is preferred. Otherwise, the nerve would have to be irradiated invasively, using a fiber optic probe.

The ear canal (external auditory meatus, external acoustic meatus), is a tube running from the outer ear to the middle ear. The human ear canal extends from the pinna (auricula, external portion of the ear) to the eardrum and is about 26 mm in length and 7 mm in diameter. Afferent nerves carried by the auricular branch of the vagus nerve (ABVN, also known as Arnold's nerve and Alderman's nerve) innervate the external auditory meatus. Mechanical stimulation of the ABVN in some individuals may elicit the Arnold's ear-cough reflex that is similar to a reflex that may be elicited by stimulating other branches of the vagus nerve. [TEKDEMIR I, Asian A, Elhan A. A clinico-anatomic study of the auricular branch of the vagus nerve and Arnold's ear-cough reflex. Surg Radiol Anat 1998; 20:253-257]. The ABVN exits the skull base via the tympanomastoid fissure (auricular fissure), approximately 4 mm superior to the stylomastoid foramen. It divides into two branches outside the cranium, with one branch running anteriorly to the facial nerve and extending in the posterior wall of the external acoustic meatus. In dissections of human cadavers, TEKDEMIR et al. found it to be distributed either superiorly (in 5 cadavers) or inferiorly (in 3 cadavers) in the external acoustic meatus. Considering such anatomical variability in the location of the ABVN that exists between individuals, a device for stimulating the ABVN should be positionable with two degrees of freedom—a variable distance of insertion within the external auditory meatus, and a variable angle of rotation about the line of insertion.

Stimulation of nerves by light can be separated primarily into three mechanistic categories: photochemical, photothermal, and photomechanical. Photochemical effects ordinarily require that a dye be injected into tissue before applying the light. Photothermal effects rely on the transformation of absorbed light into heat. Photomechanical effects rely on laser-induced pressure waves disrupting tissues. After considering these potential mechanisms, Wells et al. concluded that direct neural stimulation with laser light is due to photothermal effects, at least when using infrared light sources. [Jonathon WELLS, Chris Kao, Peter Konrad, Tom Milner, Jihoon Kim, Anita Mahadevan-Jansen, and E. Duco Jansen. Biophysical Mechanisms of Transient Optical Stimulation of Peripheral Nerve. Biophysical Journal Volume 93 October 2007 2567-2580.] Accordingly, is useful to consider the stimulation of nerves by heat (thermal pulses) in conjunction with the stimulation of nerves by light.

In U.S. Pat. No. 7,657,310, entitled Treatment of reproductive endocrine disorders by vagus nerve stimulation, to William R. Buras, there is mention of the stimulation of the vagus nerve "by light such as a laser." However, that patent is concerned with invasive nerve stimulation and is unrelated to the treatment of bronchoconstriction. As indicated above, non-invasive stimulation of the vagus nerve using light (or heat) might be attempted at the ear. However, stimulation at the ear with light has apparently been attempted only using laser acupuncture [Peter WHITTAKER. Laser acupuncture: past, present, and future. Lasers in Medical Science (2004) 19: 69-80], which stimulates acupuncture meridian points, not nerves. Furthermore, those meridian points are located on the front and back of the outer ear flap (pinna), not within the external auditory meatus. Those laser acupuncture applications were successful when directed to the treatment of pain, smoking cessation, and weight loss, but as indicated above, acupuncture (including laser acupuncture) is not considered to be effective for the treatment of asthma or other disorders associated with bronchoconstriction.

Figure 4:
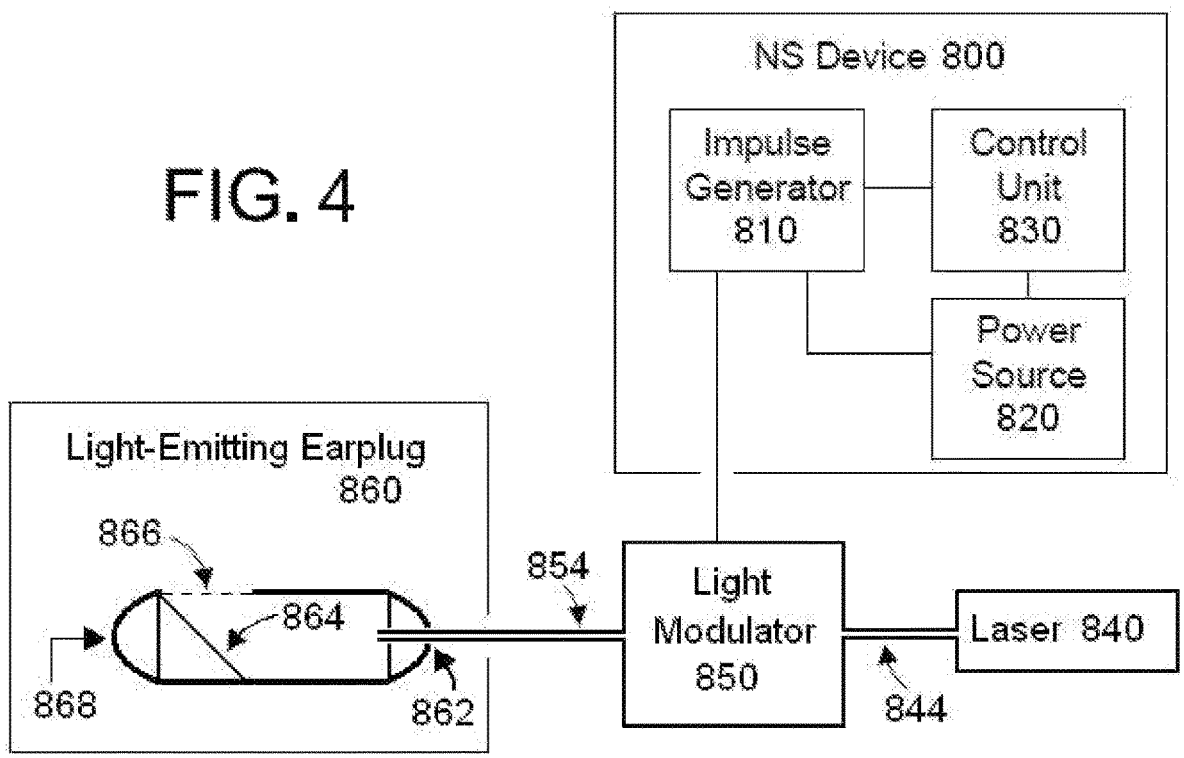
FIG. 4 is a schematic view of an alternate embodiment of a nerve modulating device according to the present invention, which controls the emission of pulses of light from an earplug.

FIG. 4 is a schematic diagram of a nerve modulating device 800 for delivering impulses of light and/or heat energy to nerves for the treatment of bronchial constriction or hypotension associated with anaphylactic shock, COPD or asthma. As shown, device 800 may include an impulse generator 810; a power source 820 coupled to the impulse generator 810; and a control unit 830 in communication with the impulse generator 810 and coupled to the power source 820. The impulse generator 810 is connected to a light modulator 850 that attenuates the maximum intensity of a beam of light that is produced by a light source, such that the intensity of light exiting the light modulator 850 tracks the magnitude of the electrical signals that are produced by the impulse generator 810. The light emerging from the light modulator 850 is directed non-invasively to a selected surface of the external auditory meatus of a patient, via an optical fiber 854 that is inserted into the light-emitting earplug 860 at its entrance port 862. The earplug 860 may be rotated about the optical fiber 854 at the entrance port 862, so that light reflected by a mirror 864 may pass through a window 866 at a variable angle of rotation about the line of earplug insertion. The earplug 860 has an outer diameter that is selected to fit snugly within the patient's ear canal and is constructed from a material selected for its flexibility, biocompatability, and ease of insertion and rotation, such as polytetrafluoroethylene. However, the terminal end of the earplug 868 may be constructed from soft rubber to protect the eardrum from inadvertent over-insertion of the earplug.

The light source may be any appropriate source of light having wavelengths in the range 10-8 meters to 10-3 meters, inclusive, including (but not limited to): a laser, an incandescent bulb, an arc lamp, a fluorescent lamp, a light-emitting diode (LED), a super-luminescent diode (SLD), a laser diode (LD), a cathodoluminescent phosphor that is excited by an electron beam, a light source such as a fluorescent dye that is excited by another light source, or a mixture of such light sources (e.g., cluster probe). In the preferred embodiment, shown in FIG. 4, the light source is a laser 840. In particular, the preferred light source is a laser that emits light in the infrared region of the electromagnetic spectrum, such as a gallium aluminum arsenide laser (wavelength 830 nm) or a gallium arsenide laser (wavelength 904 nm).

The light modulator 850 may be any appropriate device for temporally attenuating the intensity of light that impinges on the light modulator, including (but not limited to): a movable variable neutral density filter, a mechanical light chopper wheel, a deformable membrane-mirror, an acousto-optic light modulator (Bragg cell), an electro-optic light modulator such as a Pockels cell, a ferroelectric liquid crystal light modulator, a magneto-optic light modulator, a multiple quantum well light modulator, rotating crossed polarizers, and a vibrating mirror, diffraction grating, or hologram. It is also understood that the light source itself may be rapidly switched on and off or modulated in its supplied power, in which case the light source and light modulator 840/850 would be combined into a single light modulator and light-source device. The light modulator may attenuate all rays of the impinging light by the same amount, or the light modulator may selectively attenuate some rays of the impinging light so as to shape the beam, as well as to temporally modulate the intensity of the impinging light.

For the low-frequency applications described herein (less than approximately 500 Hz), the light modulator 850 may consist of an internally blackened (light-absorbing) box with a light-entrance port, to which one end of optical fiber 844 is attached; a light-exit port, to which one end of another optical fiber 854 is attached; and within the box, a positionable, linear variable neutral density filter (e.g., Reynard Corp., 1020 Calle Sombra, San Clemente, Calif., USA 92673, Model R0221Q-10, with useable wavelength range from 200 nm to 2600 nm) having a position (i.e., neutral density) that is controlled by the impulse generator 810. For example, the linear variable neutral density filter may be attached to the tip of a linear actuator like the one shown in FIG. 3, except that in the present application, the actuator is attached to the edge of the variable neutral density filter, rather than being applied to a patient. It is understood that if the light beam has a width that would cover multiple densities of the variable neutral density filter, then the light beam may first be focused with a lens onto a single point of the filter, then collected behind the filter using another lens.

In this embodiment, light passes from the laser 840 through the optical fiber 844 and then enters the modulator box 850 at its entrance port. When the filter is moved to its open position by the actuator, the light is essentially unattenuated by the filter, so that a fixed lens can focus a maximum intensity of light onto the end of optical fiber 854 at the light-exit port of the light modulator. When the filter is moved to a closed position by the actuator, light emerging from the optical fiber 844 at the entrance port is attenuated in such a way that essentially no light enters the optical fiber 854. As the actuator moves the variable neutral density filter continuously from the open position to the closed position, the intensity of light entering the optical fiber 854 varies from a maximum to a minimum, depending on the position of the variable neutral density filter, which is controlled by the actuator, which is in turn controlled by the impulse generator 810, which is in turn controlled by the control unit 830. Thus, by controlling the position of the filter within the light modulator, the control unit 830 may control the intensity of the light that enters the optical fiber 854, thereby controlling the intensity of light entering the light-emitting earplug 860 at its entrance port 862. It is understood in the art that instead of using a linear actuator, one could use a rotary motor in conjunction with a mirror or a circular variable neutral density filter that is mounted on the rotary motor shaft, wherein the angle of the motor shaft is controlled by an impulse generator; or one could use other light modulating methods that were mentioned above. It is also understood that when the light entering the earplug is blocked by the light modulator 850, infrared light may be collected from the surface of the external auditory meatus by the mirror 864 and optical fiber 862. In one embodiment of the invention, a beam-splitter is interposed between the optical fiber 862 and light modulator 850 so that light (black-body radiation) passing backwards from the ear and through the optical fiber 862 is reflected into an infrared-sensing thermometer [U.S. Pat. No. 6,272,375, entitled Mid infrared transmitting fiber optic based otoscope for non contact tympanic membrane thermometry, to Katzir et al.; U.S. Pat. No. 5,167,235, entitled Fiber optic ear thermometer, to Seacord et al.; U.S. Pat. No. 5,381,796, entitled Ear thermometer radiation detector, to Francesco Pompei; U.S. Pat. No. 5,790,586, entitled Method and apparatus for simultaneously illuminating, viewing and measuring the temperature of a body, to Hilton, Jr. et al.]. When such a thermometer is present, over-irradiation of the external auditory meatus may be prevented by sending an auditory meatus-temperature signal to the control unit 830. In that case, the control unit 830 would attenuate the light by controlling the light modulator 850 so as to keep the temperature within a specified safe range. The control unit 830 may also allow light to pass only during selected phases of the respiratory cycle, so that during other phases of respiration, excess heat may be transported from the area of light stimulation by blood vessels of the ear. In another embodiment, a tube is inserted into the earplug along its side-wall to inject air that cools the external auditory meatus at the window 866, with another tube inserted into the earplug near the entrance port 862 to carry or suck return air from earplug chamber. The air can be injected so as to maintain constant air pressure within the earplug; or the air pressure can also pulsate, so as to provide mechanical stimulation to the external auditory meatus at the window 855, becoming another embodiment of the mechanical nerve stimulation that was disclosed above.

The control unit 830 may control the impulse generator 810 for generation of a signal suitable for amelioration of the bronchial constriction or hypotension when the signal is applied to the nerve non-invasively via the light-emitting earplug 860. It is noted that nerve modulating device 800 may be referred to by its function as a pulse generator. U.S. Patent Application Publications 2005/0075701 and 2005/0075702, both to Shafer, both of which are incorporated herein by reference, relating to stimulation of neurons of the sympathetic nervous system to attenuate an immune response, contain descriptions of pulse generators that may be applicable to the present invention, when adapted for use with an optical modulator.

Considering that the nerve stimulating device 300 in FIG. 1 controls electrical currents within a coil of wire, and as described in the embodiment above concerning use of a linear actuator to control movement of a variable light filter, the nerve stimulating device 800 in FIG. 4 also controls electrical currents within a coil of wire in the actuator, their functions are analogous, except that one stimulates nerves via the pulse of a magnetic field, and the other stimulates nerves via a pulse of light. Accordingly, the features recited for the nerve stimulating device 300, such as its use for feedback involving $FEV_1$ surrogates, control of the heart rate and blood pressure, stimulation during selected phases of the respiratory cycle, and preferred frequency of stimulation, apply as well to the nerve stimulating device 800 and will not be repeated here. The preferred parameters for each nerve stimulating device are those that produce the effects described below in connection with the detailed description our experiments.

In yet another embodiment of the invention, electrodes applied to the surface of the neck, or to some other surface of the body, are used to non-invasively deliver electrical energy to a nerve, instead of delivering the energy to the nerve via a magnetic coil, mechanical vibrations and/or pulses of light. In particular, the vagus nerve may be been stimulated non-invasively using electrodes applied via leads to the surface of the skin. For example, U.S. Pat. No. 7,340,299, entitled Methods of indirectly stimulating the vagus nerve to achieve controlled asystole, to John D. Puskas, discloses the stimulation of the vagus nerve using electrodes placed on the neck of the patient, but that patent is unrelated to the treatment of bronchoconstriction. Non-invasive electrical stimulation of the vagus nerve has also been described in Japanese patent application JP2009233024A with a filing date of Mar. 26, 2008, entitled Vagus Nerve Stimulation System, to Fukui Yoshihito, in which a body surface electrode is applied to the neck to stimulate the vagus nerve electrically. However, that application pertains to the control of heart rate and is unrelated to the treatment of bronchoconstriction.

Patent application US2010/0057154, entitled Device and Method for the Transdermal Stimulation of a Nerve of the Human Body, to Dietrich et al., discloses a non-invasive transcutaneous/transdermal method for stimulating the vagus nerve, at an anatomical location where the vagus nerve has paths in the skin of the external auditory canal. Their non-invasive method involves performing electrical stimulation at that location, using surface stimulators that are similar to those used for peripheral nerve and muscle stimulation for treatment of pain (transdermal electrical nerve stimulation), muscle training (electrical muscle stimulation) and electroacupuncture of defined meridian points. The method used in that application is similar to the ones used in U.S. Pat. No. 4,319,584, entitled Electrical pulse acupressure system, to McCall, for electroacupuncture; U.S. Pat. No. 5,514,175 entitled Auricular electrical stimulator, to Kim et al., for the treatment of pain; and U.S. Pat. No. 4,966,164, entitled Combined sound generating device and electrical acupuncture device and method for using the same, to Colsen et al., for combined sound/electroacupuncture. A related application is US2006/0122675, entitled Stimulator for auricular branch of vagus nerve, to Libbus et al. Similarly, U.S. Pat. No. 7,386,347, entitled Electric stimulator for alpha-wave derivation, to Chung et al., described electrical stimulation of the vagus nerve at the ear. Patent application US2008/0288016, entitled Systems and Methods for Stimulating Neural Targets, to Amurthur et al., also discloses electrical stimulation of the vagus nerve at the ear. However, none of the disclosures in these patents or patent applications for electrical stimulation of the vagus nerve at the ear are used to treat bronchoconstriction.

The present embodiment of the invention uses some of the methods and devices for delivery of electrical energy to nerves via electrodes that were previously disclosed in the commonly assigned co-pending U.S. patent application Ser. No. 12/422,483, entitled Percutaneous Electrical Treatment of Tissue, which is hereby incorporated by reference in its entirety. FIG. 1 of that application illustrates a nerve stimulating device that functions in a manner that is analogous to the nerve stimulating device shown in FIG. 1 of the present invention, except that electrical energy is applied to electrodes rather than to a coil.

In the present embodiment of the invention, a nerve stimulating device delivers electrical impulses to nerves. The device may include an electrical impulse generator; a power source coupled to the electrical impulse generator; a control unit in communication with the electrical impulse generator and coupled to the power source; and an electrode assembly coupled to the electrical impulse generator for attachment via lead to one or more selected regions of the patient's body. The control unit may control the electrical impulse generator for generation of a signal suitable for amelioration of a patient's condition when the signal is applied via the electrode assembly to the nerve. It is noted that the nerve modulating device may be referred to by its function as a pulse generator. U.S. Patent Application Publications 2005/0075701 and 2005/0075702, both to Shafer, both of which are incorporated herein by reference, relating to stimulation of neurons of the sympathetic nervous system to attenuate an immune response, contain descriptions of pulse generators that may be applicable to various embodiments of the present invention.

The present invention differs from the one disclosed in the above-mentioned commonly assigned co-pending U.S. patent application Ser. No. 12/408,131 because in the present invention, the electrodes or their corresponding leads are applied non-invasively to the surface of the neck of the patient, or to some other surface of the body, thereby delivering electrical energy to a nerve through the skin and through underlying tissue that surrounds the nerve. Accordingly, what follows is a disclosure of the configuration of the electrodes and their corresponding leads when applied non-invasively to the surface of the skin. Preferred embodiments of other aspects of the invention are as described below in connection with the experiments that were conducted by the applicant and that were disclosed in the co-pending U.S. patent application Ser. No. 12/408,131.

Proceeding from the skin of the neck above the sternocleidomastoid muscle to the vagus nerve, a line would pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein is the preferred location for non-invasive stimulation of the vagus nerve. In the preferred embodiment, the electrode configuration would be centered on such a point, at the level of about the fifth to sixth cervical vertebra. Typically, the location of the carotid sheath or jugular veins in a patient (and therefore the location of the vagus nerve) will be ascertained in any manner known in the art, e.g., by feel or ultrasound imaging.

Embodiments of the present invention differ with regard to the number of electrodes that are used, the distance between electrodes, and whether disk or ring electrodes are used. In the preferred embodiment of the method, one selects the electrode configuration for individual patients, in such a way as to optimally focus electric fields and currents onto the selected nerve, without generating excessive currents on the surface of the skin. The method describing this tradeoff between focality and surface currents is as described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. The present invention uses the electrode configurations that are listed in that publication (bipolar, tripolar, concentric ring, and double concentric ring, each having multiple separations and radii), except that in our invention, elliptical ring electrodes are also used rather than just circular ring electrodes, in which elliptical electrodes may have a major axis that may be as large as ten times the length of the ellipse's minor axis. When elliptical electrodes are used, the major axis of the ellipse is aligned to be parallel with the axis of the nerve that is selected for stimulation. Furthermore, the electrodes may fit the curvature of patient's body surface, rather than be only planar. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

To implement the preferred embodiment, the user endeavors to stimulate the selected nerve with a succession of electrode configurations, beginning with the most focal configuration (e.g., the one with the highest value of mDESCD/CSCD in Table 1 of the article by DATTA et al.). For the initial configuration, the electrodes are centered on the patient's neck at the above-mentioned preferred location, and the maximum pulse current is slowly increased until the patient first feels an uncomfortable sensation at the surface of the skin. The maximum pulse current is then reduced by about 5 percent, and after about ten minutes of stimulation, the effect of the stimulation is ascertained by measuring the patient's $FEV_1$ or any of its surrogate measurements that were described above. If stimulation with that electrode configuration is not successful in significantly increasing the patient's $FEV_1$, the electrode configuration is replaced with one that is less focal (e.g., the one with second to the highest value of mDESCD/CSCD in Table 1 of the article by DATTA et al.). Again, the maximum pulse current is slowly increased until the patient first feels an uncomfortable sensation at the surface of the skin; the maximum pulse current is reduced by about 5 percent; and the effect of the stimulation is ascertained by measuring the patient's $FEV_1$ or any of the surrogate measurements described above. If stimulation with that second electrode configuration is not successful in significantly increasing the patient's $FEV_1$, the electrode configuration is again replaced with one that is less focal (e.g., the one with third to the highest value of mDESCD/CSCD in Table 1 of the article by DATTA et al.). Proceeding in this manner, one may eventually determine that there is an electrode configuration that produces a significant increase in the patient's $FEV_1$, without generating excessive currents on the surface of the skin. In alternate embodiments or the invention, the electrode configurations may be successively more focal, or the electrode configurations may be restricted to only one type (such as concentric ring), or distances and diameters other than those listed by DATTA et al. may be used, or one may select electrode configurations based on previous experience with a patient.

Considering that the nerve stimulating device 300 in FIG. 1 and the nerve stimulating device described above for use with electrodes both control the shape of electrical impulses, their functions are analogous, except that one stimulates nerves via a pulse of a magnetic field, and the other stimulates nerves via an electrical pulse applied through surface electrodes. Accordingly, the features recited for the nerve stimulating device 300, such as its use for feedback involving $FEV_1$ surrogates, control of the heart rate and blood pressure, stimulation during selected phases of the respiratory cycle, and preferred frequency of stimulation, apply as well to the latter stimulating device and will not be repeated here. The preferred parameters for each nerve stimulating device are those that produce the effects described below in connection with the detailed description our experiments.

A general approach to treating bronchial constriction in accordance with one or more embodiments of the invention is now described, before discussing the details of applicant's experiments that were summarized above. The general approach may include a method of (or apparatus for) treating bronchial constriction associated with anaphylactic shock, COPD or asthma, comprising applying at least one impulse of energy to one or more selected nerve fibers of a mammal in need of relief of bronchial constriction. The method may include applying one or more stimulation signals to produce at least one impulse of energy, wherein the one or more stimulation signals are of a frequency between about 15 Hz to 50 Hz.

The one or more stimulation signals may be of an amplitude equivalent to between about 1-12 joules per coulomb of displaced charged particles. The one or more stimulation signals may be one or more of a full or partial sinusoid, square wave, rectangular wave, and/or triangle wave. The one or more stimulation signals may have a pulsed on-time of between about 50 to 500 microseconds, such as about 100, 200 or 400 microseconds. The polarity of the pulses may be maintained either positive or negative. Alternatively, the polarity of the pulses may be positive for some periods of the wave and negative for some other periods of the wave. By way of example, the polarity of the pulses may be altered about every second.

In one particular embodiment of the present invention, impulses of energy are delivered to one or more portions of the vagus nerve. The vagus nerve is composed of motor and sensory fibers. The vagus nerve leaves the cranium and is contained in the same sheath of dura matter with the accessory nerve. The vagus nerve passes down the neck within the carotid sheath to the root of the neck. The branches of distribution of the vagus nerve include, among others, the superior cardiac, the inferior cardiac, the anterior bronchial and the posterior bronchial branches. On the right side, the vagus nerve descends by the trachea to the back of the root of the lung, where it spreads out in the posterior pulmonary plexus. On the left side, the vagus nerve enters the thorax, crosses the left side of the arch of the aorta, and descends behind the root of the left lung, forming the posterior pulmonary plexus.

In mammals, two vagal components have evolved in the brainstem to regulate peripheral parasympathetic functions. The dorsal vagal complex (DVC), consisting of the dorsal motor nucleus (DMNX) and its connections, controls parasympathetic function below the level of the diaphragm, while the ventral vagal complex (VVC), comprised of nucleus ambiguus and nucleus retrofacial, controls functions above the diaphragm in organs such as the heart, thymus and lungs, as well as other glands and tissues of the neck and upper chest, and specialized muscles such as those of the esophageal complex.

The parasympathetic portion of the vagus innervates ganglionic neurons which are located in or adjacent to each target organ. The VVC appears only in mammals and is associated with positive as well as negative regulation of heart rate, bronchial constriction, bronchodilation, vocalization and contraction of the facial muscles in relation to emotional states. Generally speaking, this portion of the vagus nerve regulates parasympathetic tone. The VVC inhibition is released (turned off) in states of alertness. This in turn causes cardiac vagal tone to decrease and airways to open, to support responses to environmental challenges.

The parasympathetic tone is balanced in part by sympathetic innervations, which generally speaking supplies signals tending to relax the bronchial muscles so overconstriction does not occur. Overall, airway smooth muscle tone is dependent on several factors, including parasympathetic input, inhibitory influence of circulating epinephrine, iNANC nerves and sympathetic innervations of the parasympathetic ganglia. Stimulation of certain nerve fibers of the vagus nerve (upregulation of tone), such as occurs in asthma or COPD attacks or anaphylactic shock, results in airway constriction and a decrease in heart rate. In general, the pathology of severe asthma, COPD and anaphylaxis appear to be mediated by inflammatory cytokines that overwhelm receptors on the nerve cells and cause the cells to massively upregulate the parasympathetic tone.

The methods described herein of applying an impulse of energy to a selected region of the vagus nerve may further be refined such that the at least one region may comprise at least one nerve fiber emanating from the patient's tenth cranial nerve (the vagus nerve), and in particular, at least one of the anterior bronchial branches thereof, or alternatively at least one of the posterior bronchial branches thereof. Preferably the impulse is provided to at least one of the anterior pulmonary or posterior pulmonary plexuses aligned along the exterior of the lung. As necessary, the impulse may be directed to nerves innervating only the bronchial tree and lung tissue itself. In addition, the impulse may be directed to a region of the vagus nerve to stimulate, block and/or modulate both the cardiac and bronchial branches. As recognized by those having skill in the art, this embodiment should be carefully evaluated prior to use in patients known to have preexisting cardiac issues.

Experiments were performed to identify exemplary methods of how signals, such as electrical signals, can be supplied to the peripheral nerve fibers that innervate and/or control the bronchial smooth muscle to (i) reduce the sensitivity of the muscle to the signals to constrict, and (ii) to blunt the intensity of, or break the constriction once it has been initiated. In particular, specific signals were applied to the selected nerves in guinea pigs to produce selective stimulation, interruption or reduction in the effects of nerve activity leading to attenuation of histamine-induced bronchoconstriction.

Male guinea pigs (400 g) were transported to the lab and immediately anesthetized with an i.p. injection of urethane 1.5 g/kg. Skin over the anterior neck was opened and the carotid artery and both jugular veins were cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with the nerve stimulation. In these experiments, vagus nerves were exposed and connected to electrodes to allow selective stimuli of these nerves. Following 15 minutes of stabilization, baseline hemodynamic and airway pressure measurements were made before and after the administration of repetitive doses of i.v. histamine.

Following the establishment of a consistent response to i.v. histamine, nerve stimulation was attempted at variations of frequency, voltage and pulse duration to identity parameters that attenuate responses to i.v. histamine. Bronchoconstriction in response to i.v. histamine is known to be due both to direct airway smooth muscle effects and to stimulation of vagal nerves to release acetylcholine.

At the end of vagal nerve challenges, atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

In order to measure the bronchoconstriction, the airway pressure was measured in two places. The blood pressure and heart rate were measured to track the subjects' vital signs. In all the following graphs, the top line BP shows blood pressure, second line AP1 shows airway pressure, third line AP2 shows airway pressure on another sensor, the last line HR is the heart rate derived from the pulses in the blood pressure.

In the first animals, the signal frequency applied was varied from less than 1 Hz through 2,000 Hz, and the voltage was varied from 1V to 12V. Initial indications seemed to show that an appropriate signal was 1,000 Hz, 400 µs, and 6-10V.

Figure 5:
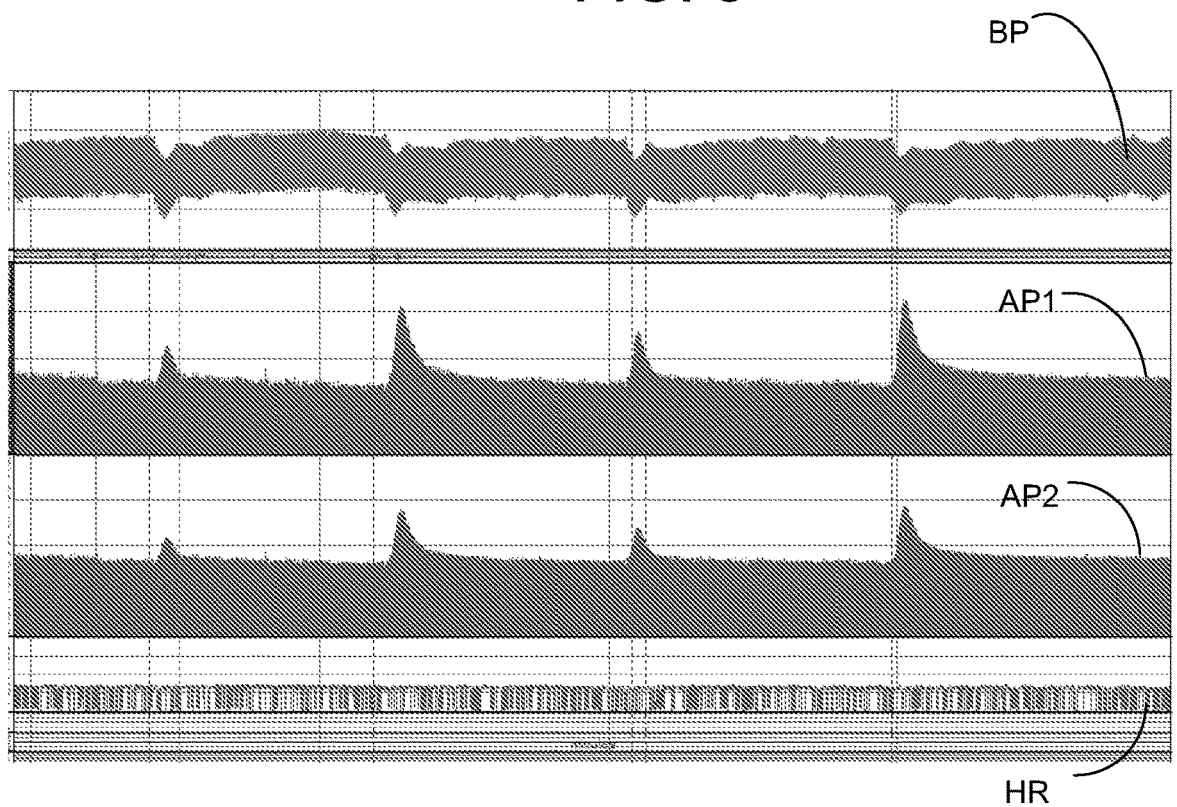
FIGS. 5-14 graphically illustrate exemplary experimental data obtained on guinea pigs in accordance with multiple embodiments of the present invention.

FIG. 5 graphically illustrates exemplary experimental data on guinea pig #2. More specifically, the graphs of FIG. 5 show the effect of a 1000 Hz, 400 µS, 6V square wave signal applied simultaneously to both left and right branches of the vagus nerve in guinea pig #2 when injected with 12 µg/kg histamine to cause airway pressure to increase. The first peak in airway pressure is histamine with the electric signal applied to the vagus, the next peak is histamine alone (signal off), the third peak is histamine and signal again, fourth peak is histamine alone again. It is clearly shown that the increase in airway pressure due to histamine is reduced in the presence of the 1000 Hz, 400 µS and 6V square wave on the vagus nerve. The animal's condition remained stable, as seen by the fact that the blood pressure and heart rate are not affected by this electrical signal.

After several attempts on the same animal to continue to reproduce this effect with the 1,000 Hz signal, however, we observed that the ability to continuously stimulate and suppress airway constriction was diminished, and then lost. It appeared that the nerve was no longer conducting. This conclusion was drawn from the facts that (i) there was some discoloration of the nerve where the electrode had been making contact, and (ii) the effect could be resuscitated by moving the lead distally to an undamaged area of the nerve, i.e. toward the organs, but not proximally, i.e., toward the brain. The same thing occurred with animal #3. It has been hypothesized that the effect seen was, therefore, accompanied by a damaging of the nerve, which would not be clinically desirable.

To resolve the issue, in the next animal (guinea pig #4), we fabricated a new set of electrodes with much wider contact area to the nerve. With this new electrode, we started investigating signals from 1 Hz to 3,000 Hz again. This time, the most robust effectiveness and reproducibility was found at a frequency of 25 Hz, 400 µs, 1V.

Figure 6:
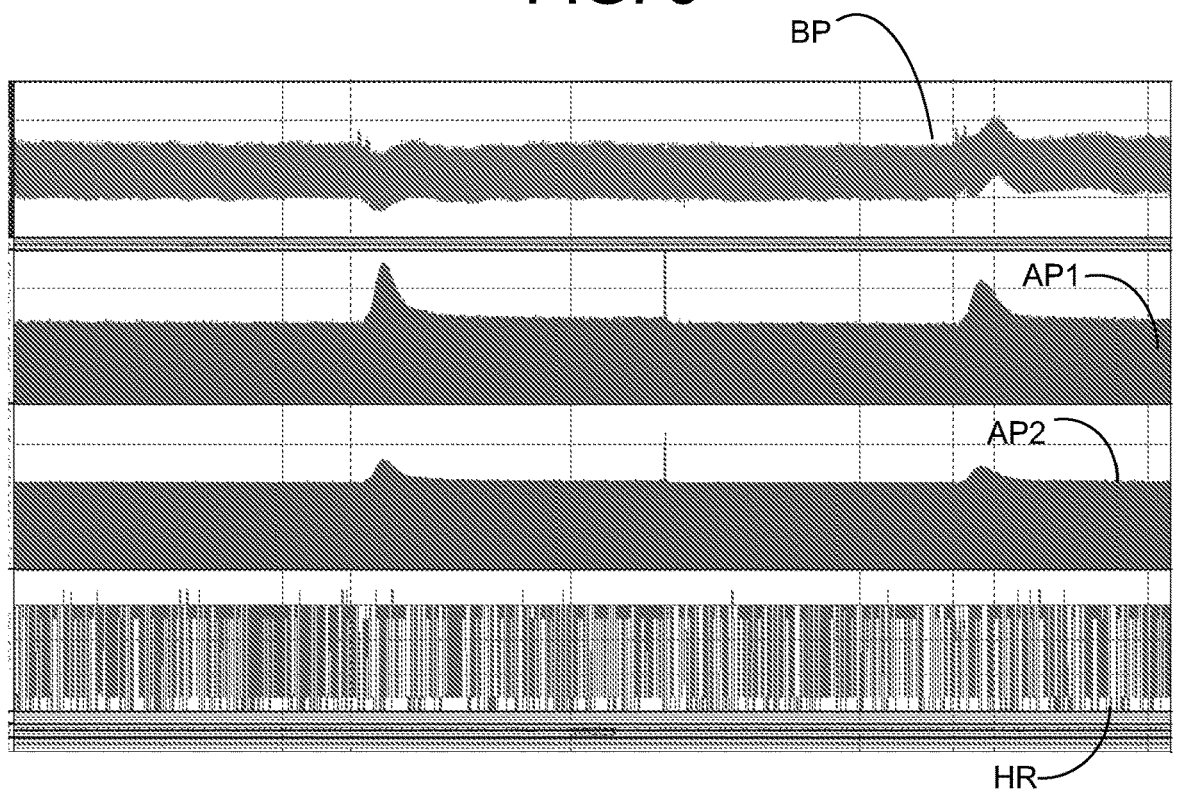

FIG. 6 graphically illustrates exemplary experimental data on guinea pig #5. The graphs of FIG. 6 show the effect of a 25 Hz, 400 µS, 1V square wave signal applied to both left and right vagus nerve in guinea pig #5 when injected with 8 µg/kg histamine to cause airway pressure to increase. The first peak in airway pressure is from histamine alone, the next peak is histamine and signal applied. It is clearly shown that the increase in airway pressure due to histamine is reduced in the presence of the 25 Hz, 400 µS, 1V square wave on the vagus nerve.

Figure 7:
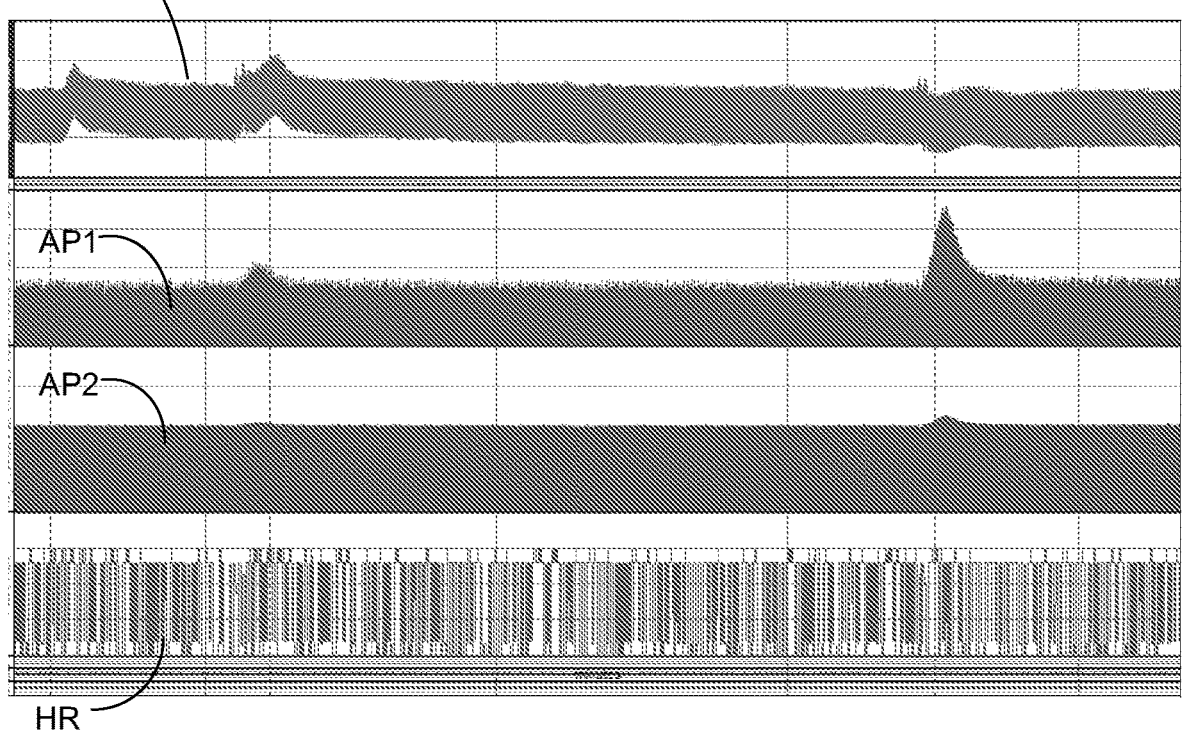

FIG. 7 graphically illustrates additional exemplary experimental data on guinea pig #5. The graphs of FIG. 7 show the effect of a 25 Hz, 200 µS, 1V square wave signal applied to both of the left and right vagus nerves in guinea pig #5 when injected with 8 µg/kg histamine to cause airway pressure to increase. The second peak in airway pressure is from histamine alone, the first peak is histamine and signal applied. It is clearly shown that the increase in airway pressure due to histamine is reduced in the presence of the 25 Hz, 200 µS, 1V square wave on the vagus nerve. It is clear that the airway pressure reduction is even better with the 200 µS pulse width than the 400 µS signal.

Figure 8:
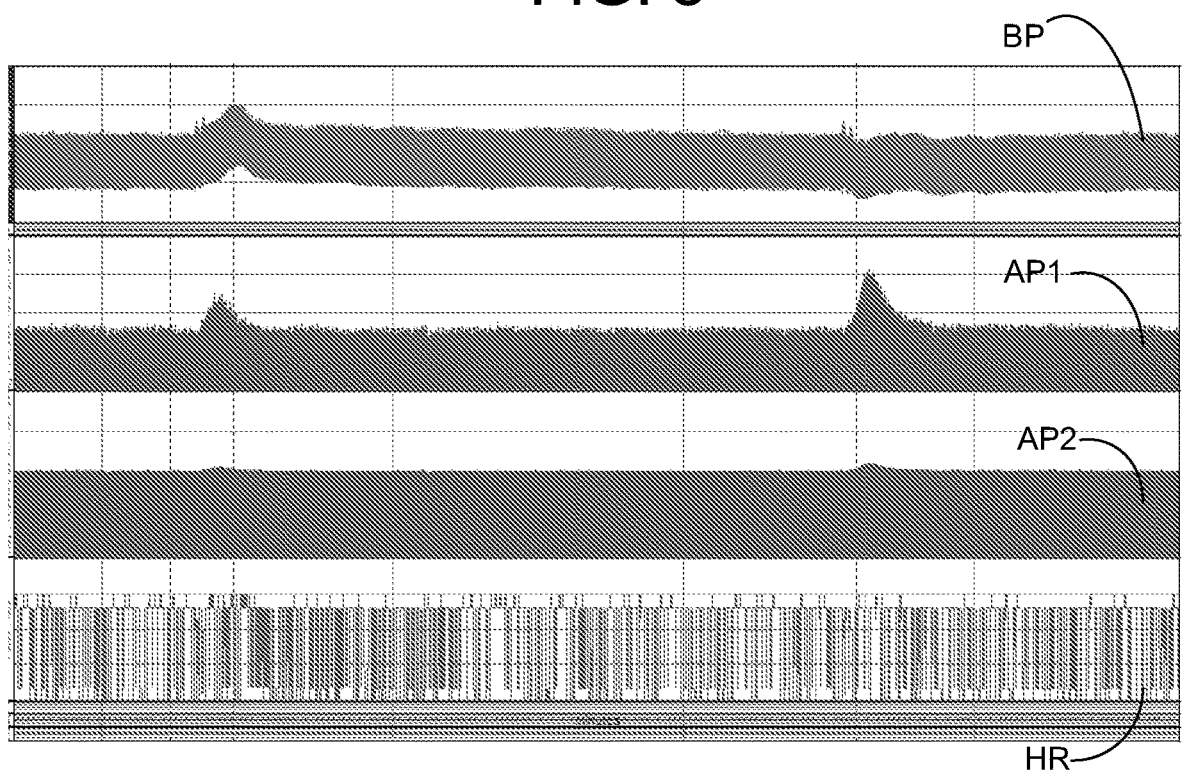

FIG. 8 graphically illustrates further exemplary experimental data on guinea pig #5. The graphs of FIG. 8 show repeatability of the effect seen in the previous graph. The animal, histamine and signal are the same as the graphs in FIG. 7.

It is significant that the effects shown above were repeated several times with this animal (guinea pig #5), without any loss of nerve activity observed. We could move the electrodes proximally and distally along the vagus nerve and achieve the same effect. It was, therefore, concluded that the effect was being achieved without damaging the nerve.

Figure 9:
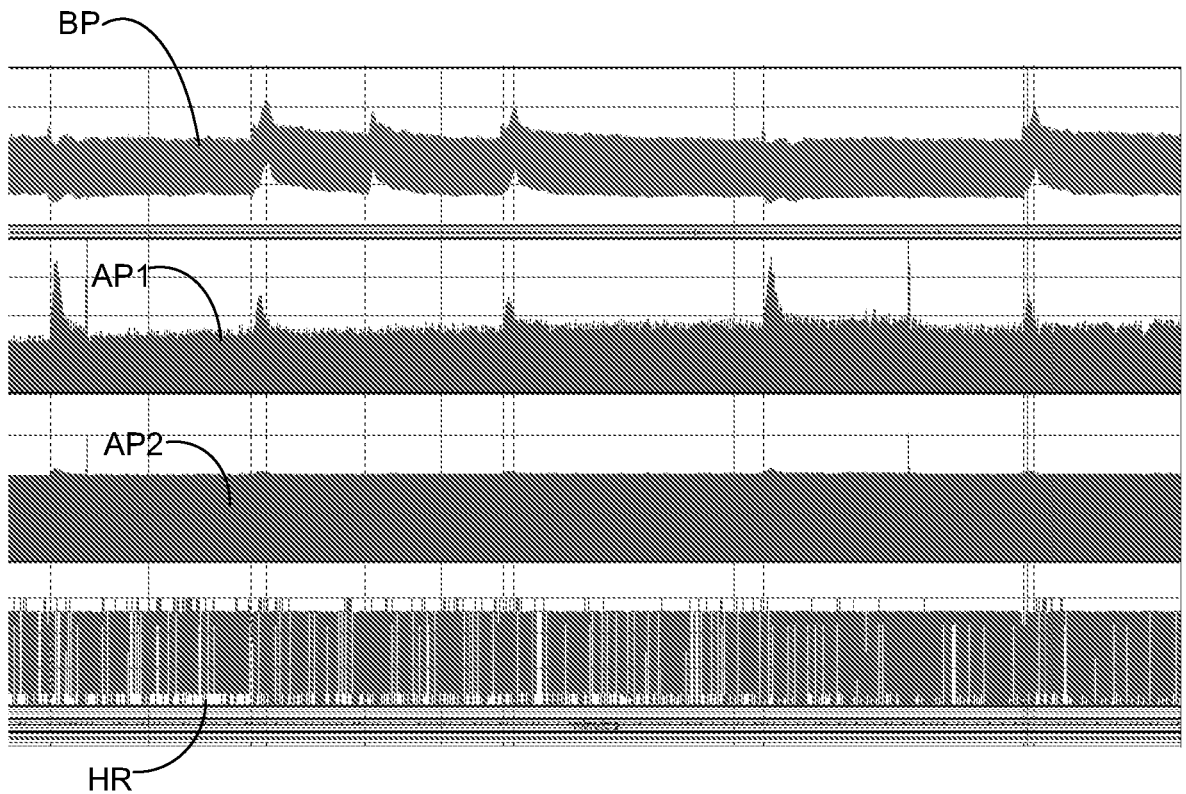

FIG. 9 graphically illustrates subsequent exemplary experimental data on guinea pig #5. The graphs of FIG. 9 show the effect of a 25 Hz, 100 µS, 1V square wave that switches polarity from + to − voltage every second. This signal is applied to both left and right vagus nerve in guinea pig #5 when injected with 8 µg/kg histamine to cause airway pressure to increase. From left to right, the vertical dotted lines coincide with airway pressure events associated with: (1) histamine alone (large airway spike—followed by a very brief manual occlusion of the airway tube); (2) histamine with a 200 µS signal applied (smaller airway spike); (3) a 100 µS electrical signal alone (no airway spike); (4) histamine with a 100 uS signal applied (smaller airway spike again); (5) histamine alone (large airway spike); and (6) histamine with the 100 µS signal applied.

This evidence strongly suggests that the increase in airway pressure due to histamine can be significantly reduced by the application of a 25 Hz, 100 µS, 1V square wave with alternating polarity on the vagus nerve.

Figure 10:
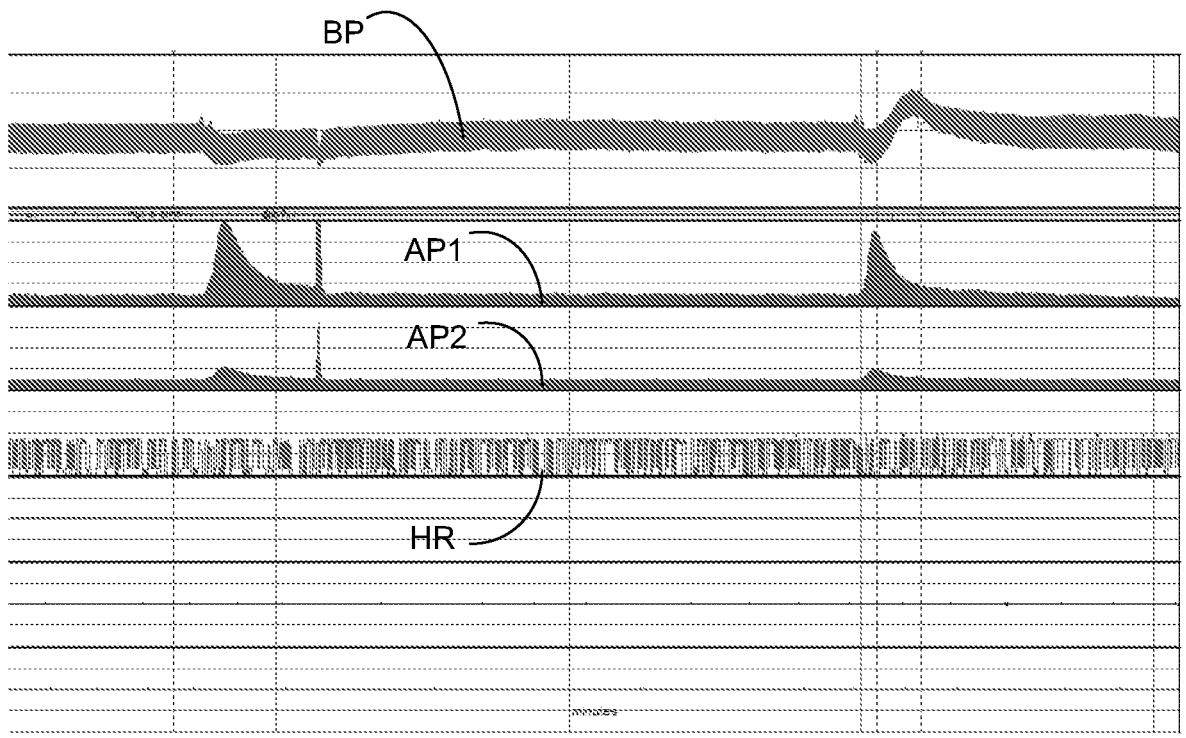

FIG. 10 graphically illustrates exemplary experimental data on guinea pig #6. The graphs in FIG. 10 show the effect of a 25 Hz, 200 µS, 1V square wave that switches polarity from + to − voltage every second. This signal is applied to both left and right vagus nerve in guinea pig #6 when injected with 16 µg/kg histamine to cause airway pressure to increase. (Note that this animal demonstrated a very high tolerance to the effects of histamine, and therefore was not an ideal test subject for the airway constriction effects, however, the animal did provide us with the opportunity to test modification of other signal parameters.)

In this case, the first peak in airway pressure is from histamine alone, the next peak is histamine with the signal applied. It is clearly shown that the increase in airway pressure due to histamine is reduced moderately in its peak, and most definitely in its duration, when in the presence of the 25 Hz, 200 µS, 1V square wave with alternating polarity on the vagus nerve.

Figure 11:
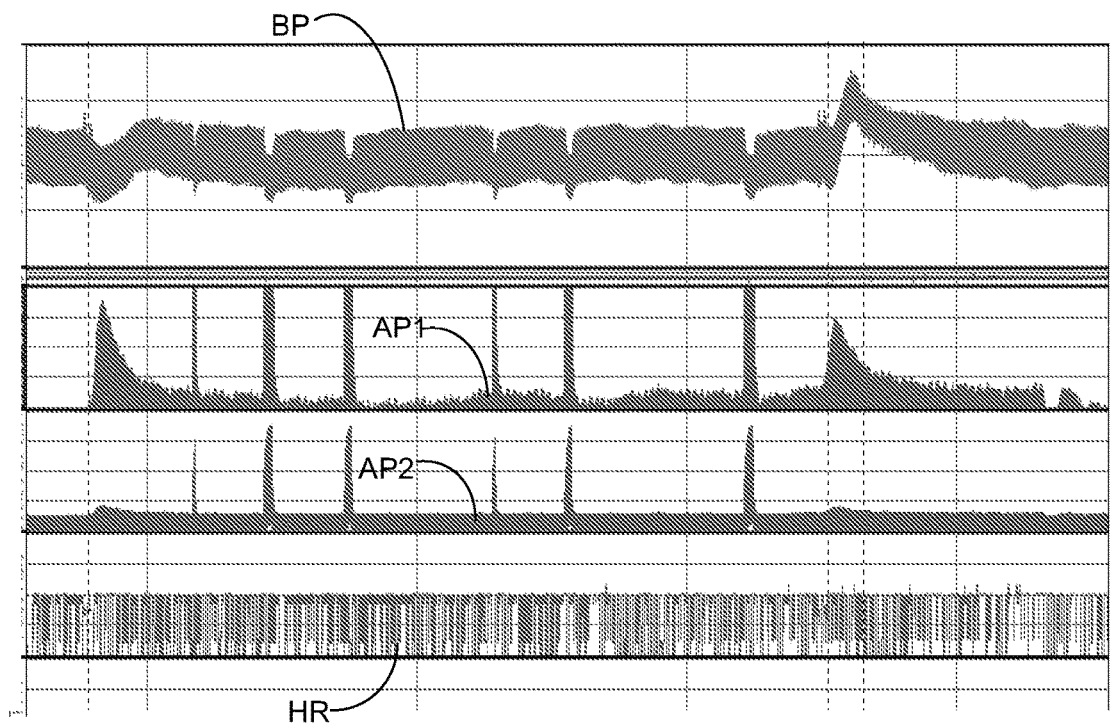

FIG. 11 graphically illustrates additional exemplary experimental data on guinea pig #6. As mentioned above, guinea pig #6 in the graphs of FIG. 10 above needed more histamine than other guinea pigs (16-20 µg/kg vs 8 µg/kg) to achieve the desired increase in airway pressure. Also, the beneficial effects of the 1V signal were less pronounced in pig #6 than in #5. Consequently, we tried increasing the voltage to 1.5V. The first airway peak is from histamine alone (followed by a series of manual occlusions of the airway tube), and the second peak is the result of histamine with the 1.5V, 25 Hz, 200 µS alternating polarity signal. The beneficial effects are seen with slightly more impact, but not substantially better than the 1V.

Figure 12:
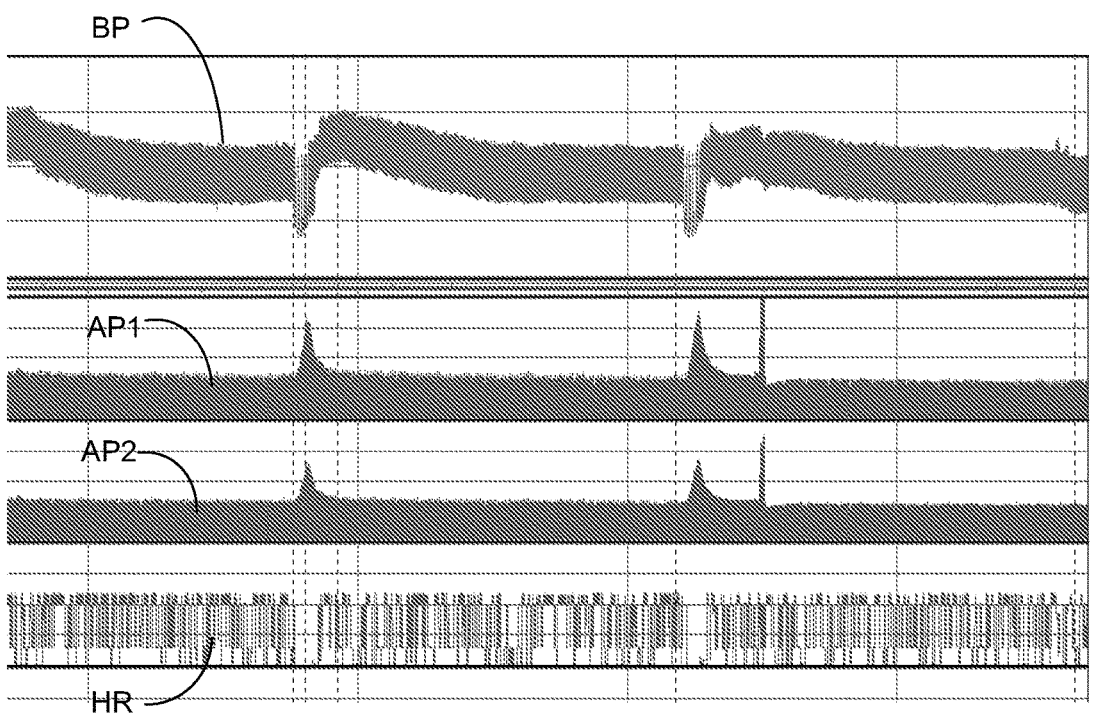

FIG. 12 graphically illustrates further exemplary experimental data on guinea pig #6. Since guinea pig #6 was losing its airway reaction to histamine, we tried to determine if the 25 Hz, 200 µS, 1V, alternating polarity signal could mitigate the effects of a 20V, 20 Hz airway pressure stimulating signal that has produced a simulated asthmatic response. The first airway peak is the 20V, 20 Hz stimulator signal applied to increase pressure, then switched over to the 25 Hz, 200 µS, 1V, alternating polarity signal. The second peak is the 20V, 20 Hz signal alone. The first peak looks modestly lower and narrower than the second. The 25 Hz, 200 µS, 1V signal may have some beneficial airway pressure reduction after electrical stimulation of airway constriction.

Figure 13:
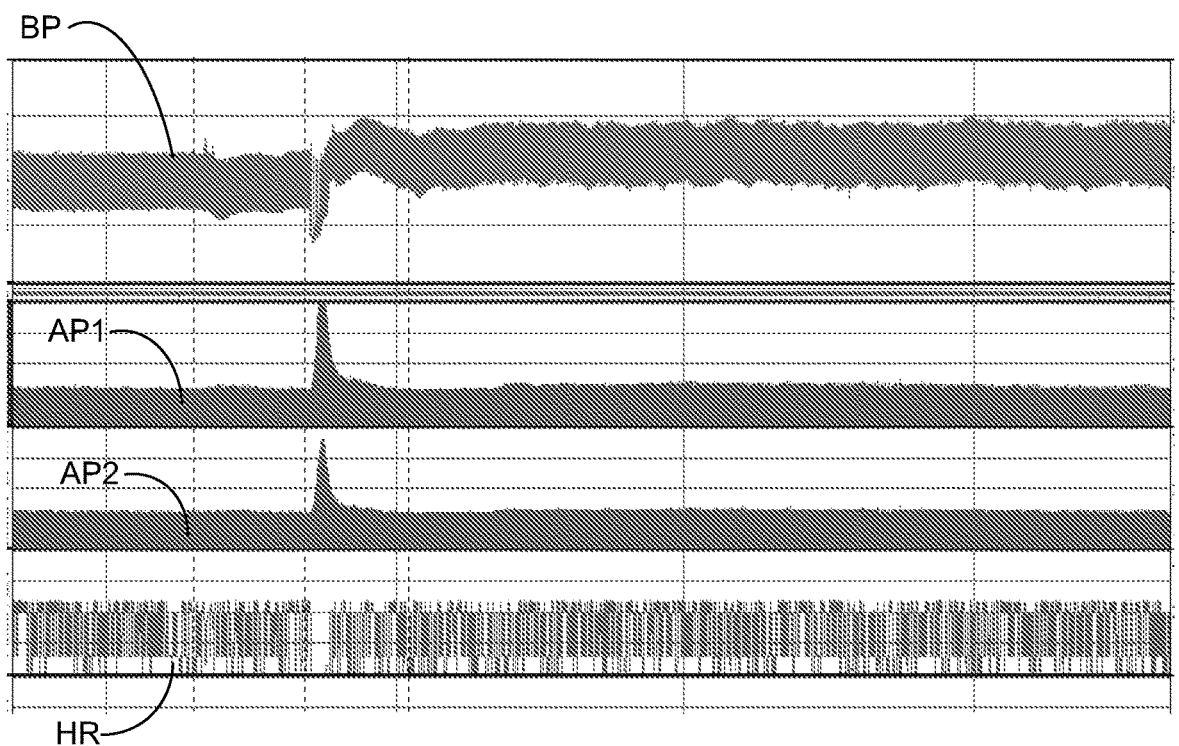

FIG. 13 graphically illustrates subsequent exemplary experimental data. On guinea pig #6 we also investigated the effect of the 1V, 25 Hz, and 200 µS alternating polarity signal. Even after application of the signal for 10 minutes continuously, there was no loss of nerve conduction or signs of damage.

Figure 14:
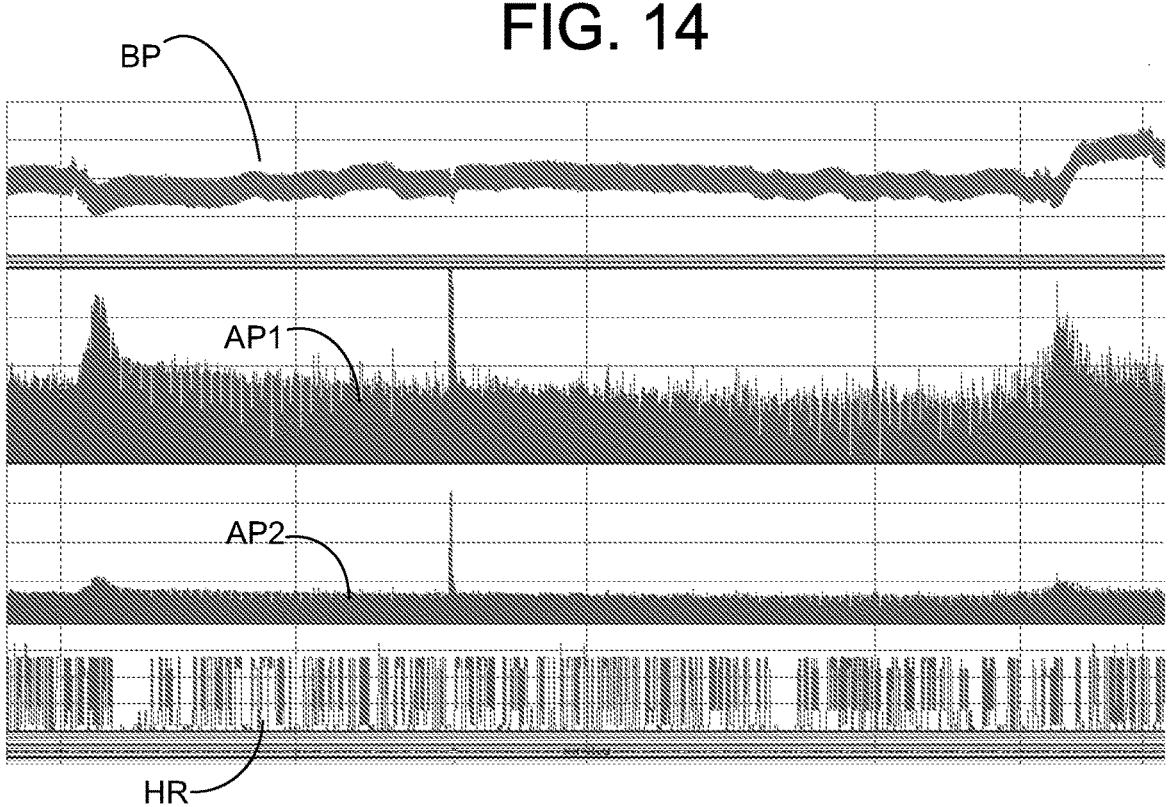
Figure 15:
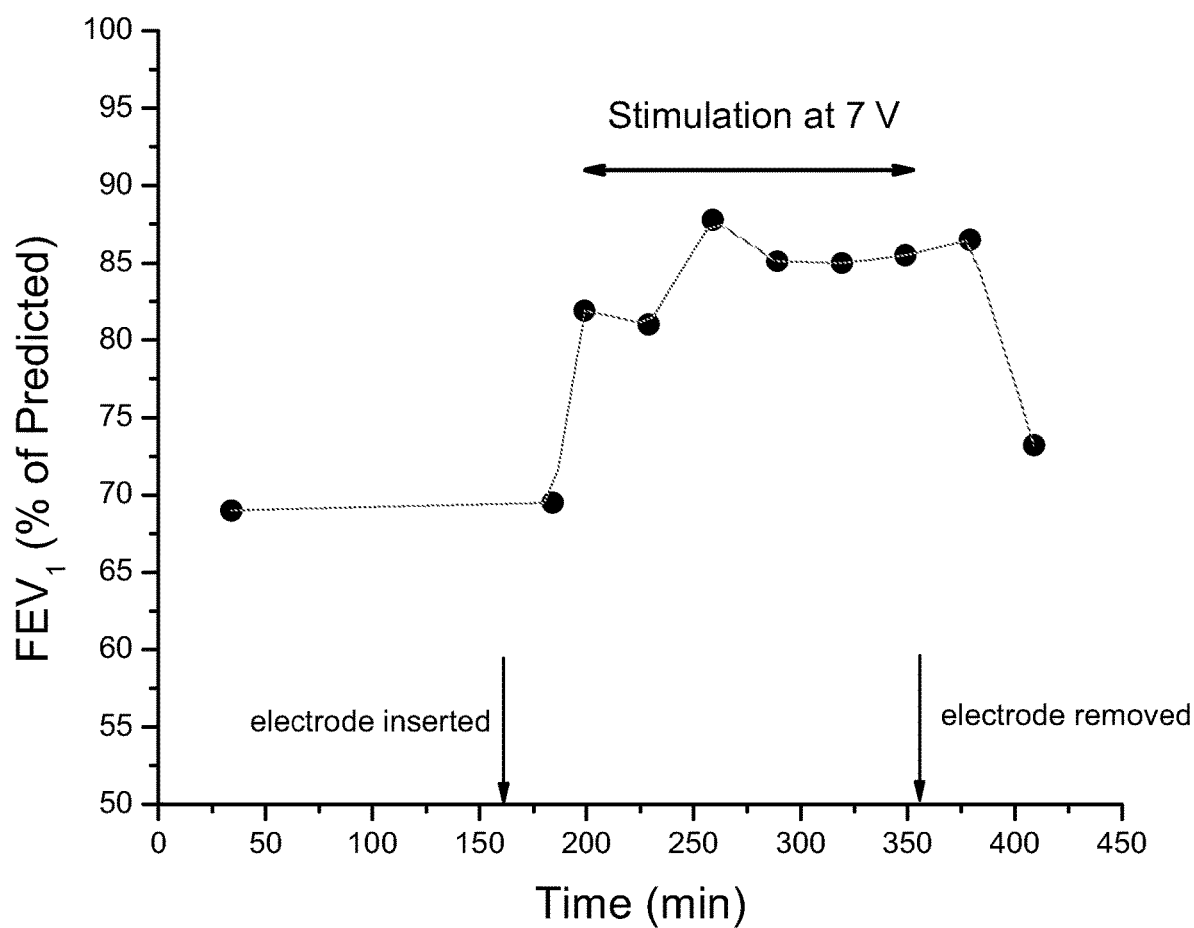
Figure 16:
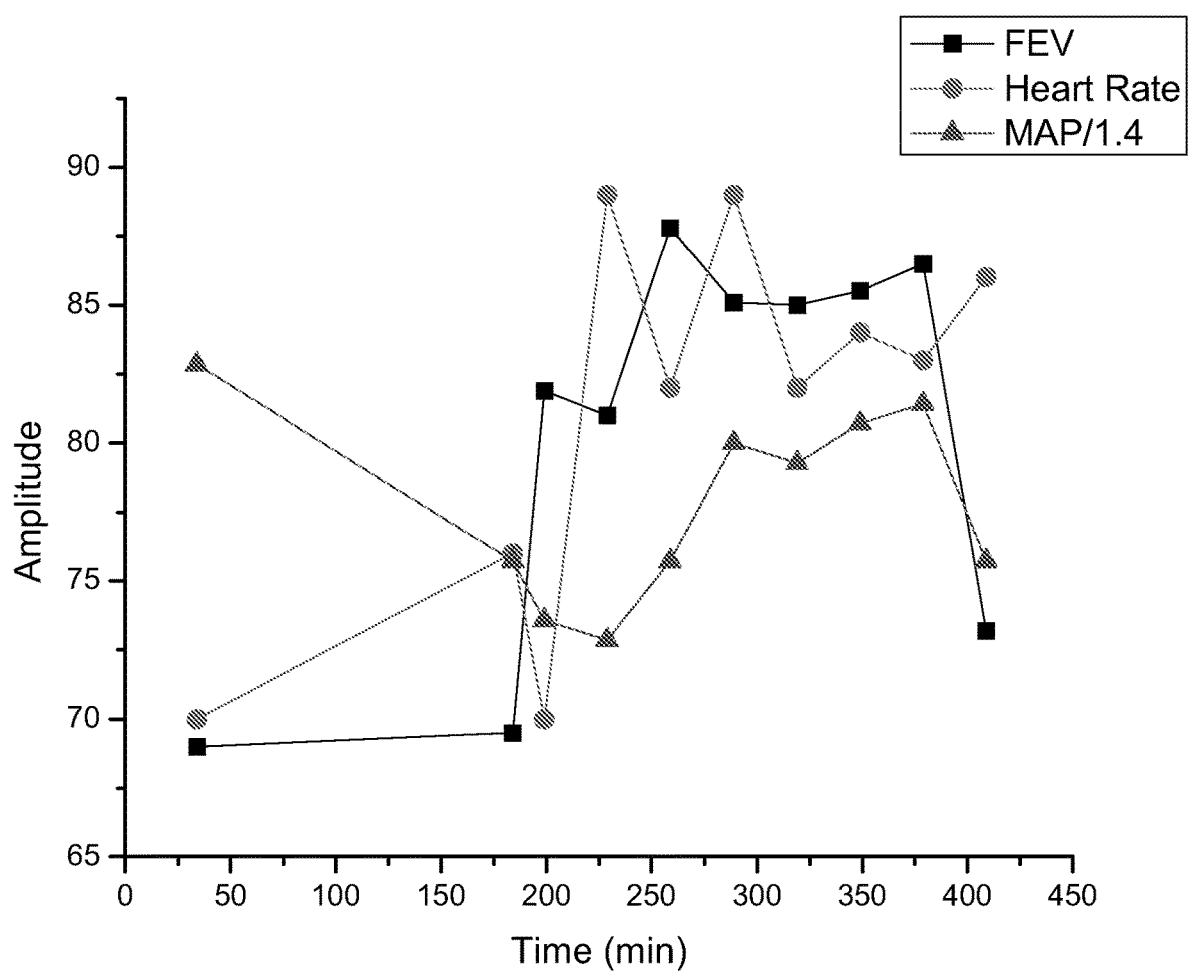

FIG. 14 graphically illustrates exemplary experimental data on guinea pig #8. The graph below shows the effect of a 25 Hz, 200 µS, 1V square wave that switches polarity from + to − voltage every second. This signal is applied to both left and right vagus nerve in guinea pig #8 when injected with 12 µg/kg histamine to cause airway pressure to increase. The first peak in airway pressure is from histamine alone, the next peak is histamine with the signal applied. It is clearly shown that the increase in airway pressure due to histamine is reduced in the presence of the 25 Hz, 200 µS, 1V square wave with alternating polarity on the vagus nerve. We have reproduced this effect multiple times, on 4 different guinea pigs, on 4 different days.

The airway constriction induced by histamine in guinea pigs can be significantly reduced by applying appropriate electrical signals to the vagus nerve. We found at least 2 separate frequency ranges that have this effect. At 1000 Hz, 6V, 400 µS the constriction is reduced, but there is evidence that this is too much power for the nerve to handle. This may be mitigated by different electrode lead design in future tests. Different types of animals also may tolerate differently differing power levels.

With a 25 Hz, 1V, 100-200 µS signal applied to the vagus nerve, airway constriction due to histamine is significantly reduced. This has been repeated on multiple animals many times. There is no evidence of nerve damage, and the power requirement of the generator is reduced by a factor of between 480 (40×6×2) and 960 (40×6×4) versus the 1000 Hz, 6V, 400 µS signal.

In addition to the exemplary testing described above, further testing on guinea pigs was made by applicant to determine the optimal frequency range for reducing bronchoconstriction. These tests were all completed similarly as above by first establishing a consistent response to i.v. histamine, and then performing nerve stimulation at variations of frequency, voltage and pulse duration to identity parameters that attenuate responses to i.v. histamine. The tests were conducted on over 100 animals at the following frequency values: 1 Hz, 10 Hz, 15 Hz, 25 Hz, 50 Hz, 250 Hz, 500 Hz, 1000 Hz, 2000 Hz and 3000 Hz at pulse durations from 0.16 ms to 0.4 ms with most of the testing done at 0.2 ms. In each of the tests, applicant attempted to achieve a decrease in the histamine transient. Any decrease was noted, while a 50% reduction in histamine transient was considered a significant decrease.

The 25 Hz signal produced the best results by far with about 68% of the animals tested (over 50 animals tested at this frequency) achieving a reduction in histamine transient and about 17% of the animals achieving a significant (i.e., greater than 50%) reduction. In fact, 25 Hz was the only frequency in which any animal achieved a significant decrease in the histamine transient. About 30% of the animals produced no effect and only 2% (one animal) resulted in an increase in the histamine transient.

The 15 Hz signal was tested on 18 animals and showed some positive effects, although not as strong as the 25 Hz signal. Seven of the animals (39%) demonstrated a small decrease in histamine transient and none of the animals demonstrated an increase in histamine transient. Also, none of the animals achieved a significant (greater than 50%) reduction as was seen with the 25 Hz signal.

Frequency ranges below 15 Hz had little to no effect on the histamine transient, except that a 1 Hz signal had the opposite effect on one animal (histamine transient actually increased indicating a further constriction of the bronchial passages). Frequency ranges at or above 50 Hz appeared to either have no effect or they increased the histamine transient and thus increased the bronchoconstriction.

These tests demonstrate that applicant has made the surprising and unexpected discovery that a signal within a small frequency band will have a clinically significant impact on reducing the magnitude of bronchial constriction on animals subject to histamine. In particular, applicant has shown that a frequency range of about 15 Hz to about 50 Hz will have some positive effect on counteracting the impact of histamine, thereby producing bronchodilation. Frequencies outside of this range do not appear to have any impact and, in some case, make the bronchoconstriction worse. In particular, applicant has found that the frequency signal of 25 Hz appears to be the optimal and thus preferred frequency as this was the only frequency tested that resulted in a significant decrease in histamine transient in at least some of the animals and the only frequency tested that resulted in a positive response (i.e., decrease in histamine transient) in at least 66% of the treated animals.

FIGS. 15-18 graphically illustrate exemplary experimental data obtained on five human patients in accordance with multiple embodiments of the present invention. In the first patient (see FIGS. 15 and 16), a 34 year-old, Hispanic male patient with a four year history of severe asthma was admitted to the emergency department with an acute asthma attack. He reported self treatment with albuterol without success. Upon admission, the patient was alert and calm but demonstrated bilateral wheezing, elevated blood pressure (BP) (163/92 mmHg) related to chronic hypertension, acute bronchitis, and mild throat hyperemia. All other vital signs were normal. The patient was administered albuterol (2.5 mg), prednisone (60 mg PO), and zithromax (500 mg PO) without improvement. The spirometry assessment of the lung function revealed a Forced Expiratory Volume in 1 second ($FEV_1$) of 2.68 l/min or 69% of predicted. Additional albuterol was administered without benefit and the patient was placed on supplemental oxygen (2 l/min).

A study entailing a new investigational medical device for stimulating the selected nerves near the carotid sheath was discussed with the patient and, after review, the patient completed the Informed Consent. Following a 90 minute observational period without notable improvement in symptoms, the patient underwent placement of a percutaneous, bipolar electrode to stimulate the selected nerves (see FIG. 16). Using anatomical landmarks and ultrasound guidance, the electrode was inserted to a position near the carotid sheath, and parallel to the vagus nerve.

The electrode insertion was uneventful and a subthreshold test confirmed the device was functioning. Spirometry was repeated and $FEV_1$ remained unchanged at 2.68 l/min. Stimulation (25 Hz, 300 microsecond pulse width signal) strength was gradually increased until the patient felt a mild muscle twitch at 7.5 volts then reduced to 7 volts. This setting achieved therapeutic levels without discomfort and the patient was able to repeat the $FEV_1$ test without difficulty. During stimulation, the $FEV_1$ improved immediately to 3.18 l/min and stabilized at 3.29 l/min (85% predicted) during 180 minutes of testing. The benefit remained during the first thirty minutes after terminating treatment, then decreased. By 60 minutes post stimulation, dyspnea returned and $FEV_1$ decreased to near prestimulation levels (73% predicted) (FIG. 2). The patient remained under observation overnight to monitor his hypertension and then discharged. At the 1-week follow-up visit, the exam showed complete healing of the insertion site, and the patient reported no after effects from the treatment.

This was, to the inventor's knowledge, the first use of nerve stimulation in a human asthma patient to treat bronchoconstriction. In the treatment report here, invasive surgery was not required. Instead a minimally invasive, percutaneous approach was used to position an electrode in close proximity to the selected nerves. This was a relatively simple and rapid procedure that was performed in the emergency department and completed in approximately 10 minutes without evidence of bleeding or scarring.

Figure 17:
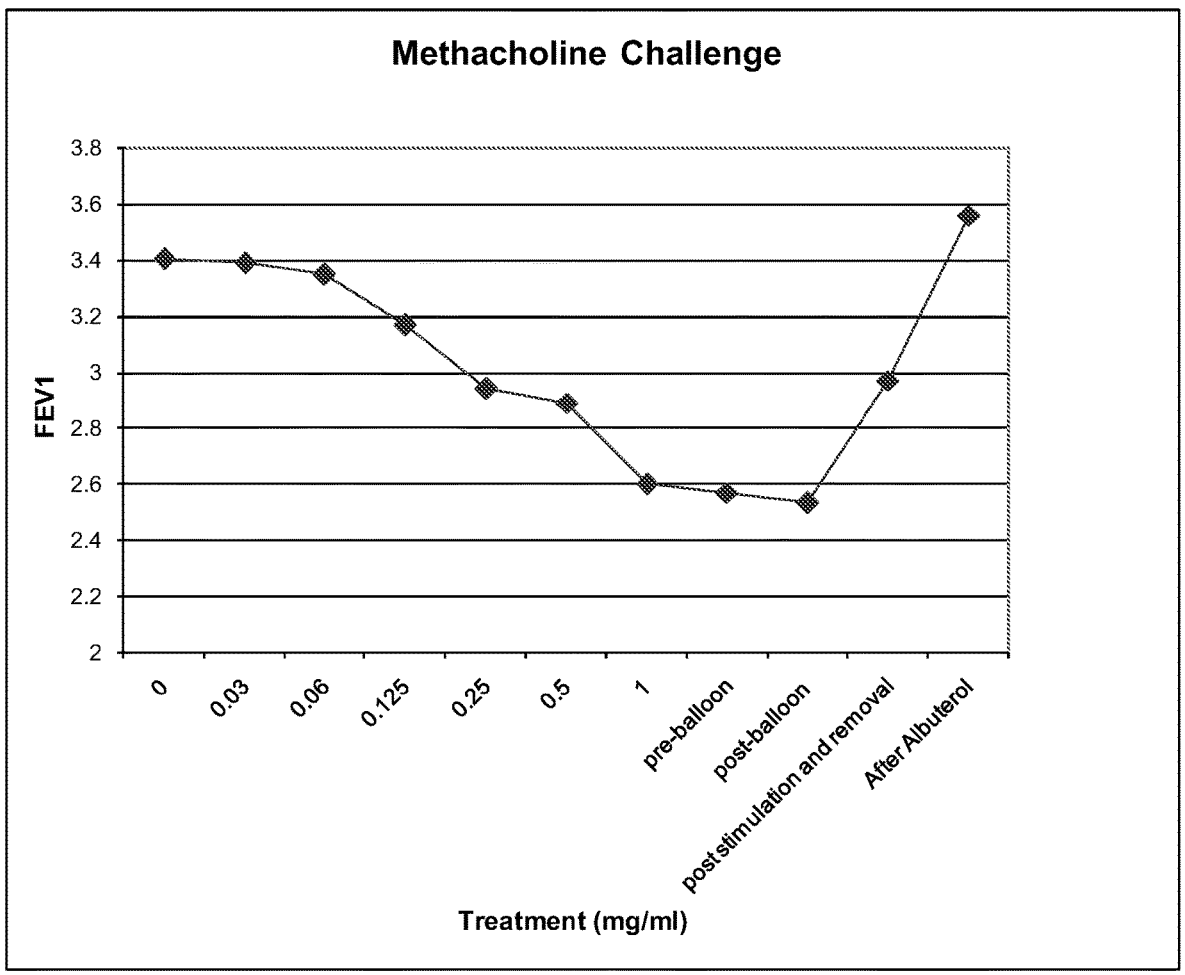

FIG. 17 graphically illustrates another patient treated according to the present invention. Increasing doses of methacholine were given until a drop of 24% in $FEV_1$ was observed at 1 mg/ml. A second $FEV_1$ was taken prior to insertion of the electrode. The electrode was then inserted and another $FEV_1$ taken after electrode insertion and before stimulation. The stimulator was then turned on to 10 V for 4 minutes, the electrode removed and a post-stimulation $FEV_1$ taken showing a 16% increase. A final rescue albuterol treatment restored normal $FEV_1$.

FIG. 18 is a table summarizing the results of all five human patients. In all cases, $FEV_1$ values were measured prior to administration of the electrical impulse delivery to the patient according to the present invention. In addition, $FEV_1$ values were measures at every 15 minutes after the start of treatment. A 12% increase in $FEV_1$ is considered clinically significant. All five patients achieved a clinically significant increase in $FEV_1$ of 12% or greater in 90 minutes or less, which represents a clinically significant increase in an acute period of time. In addition, all five patients achieved at least a 19% increase in $FEV_1$ in 150 minutes or less.

As shown, the first patient initially presented with an $FEV_1$ of 61% of predicted. Upon application of the electrical impulse described above, the first patient achieved at least a 12% increase in $FEV_1$ in 15 minutes or less and achieved a peak increase in $FEV_1$ of 43.9% after 75 minutes. The second patient presented with an $FEV_1$ of 51% of predicted, achieved at least a 12% increase in $FEV_1$ in 30 minutes or less and achieved a peak increase in $FEV_1$ of 41.2% after 150 minutes. The third patient presented with an $FEV_1$ of 16% of predicted, achieved at least a 12% increase in $FEV_1$ in 15 minutes or less and achieved a peak increase in $FEV_1$ of about 131.3% in about 150 minutes. However, it should be noted that this patient's values were abnormal throughout the testing period. The patient was not under extreme duress as a value of 16% of predicted would indicate. Therefore, the exact numbers for this patient are suspect, although the patient's symptoms clearly improved and the $FEV_1$ increased in any event. The fourth patient presented with an $FEV_1$ of predicted of 66%, achieved at least a 12% increase in $FEV_1$ in 90 minutes or less and achieved a peak increase in $FEV_1$ of about 19.7% in 90 minutes or less. Similarly, the fifth patient presented with an $FEV_1$ of predicted of 52% and achieved a 19.2% peak increase in $FEV_1$ in 15 minutes or less. The electrode in the fifth patient was unintentionally removed around 30 minutes after treatment and, therefore, a true peak increase in $FEV_1$ was not determined.

In U.S. patent application Ser. No. 10/990,938 filed Nov. 17, 2004 (Publication Number US2005/0125044A1), Kevin J. Tracey proposes a method of treating many diseases including, among others, asthma, anaphylactic shock, sepsis and septic shock by electrical stimulation of the vagus nerve. However, the examples in the Tracey application use an electrical signal that is 1 to 5V, 1 Hz and 2 mS to treat endotoxic shock, and no examples are shown that test the proposed method on an asthma model, an anaphylactic shock model, or a sepsis model. The applicants of the present application performed additional testing to determine if Tracey's proposed method has any beneficial effect on asthma or blood pressure in the model that shows efficacy with the method used in the present application. The applicants of the present application sought to determine whether Tracey's signals can be applied to the vagus nerve to attenuate histamine-induced bronchoconstriction and increase in blood pressure in guinea pigs.

Male guinea pigs (400 g) were transported to the lab and immediately anesthetized with an i.p. injection of urethane 1.5 g/kg. Skin over the anterior neck was opened and the carotid artery and both jugular veins are cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with vagal nerve stimulation. Both vagus nerves were exposed and connected to electrodes to allow selective stimuli of these nerves. Following 15 minutes of stabilization, baseline hemodynamic and airway pressure measurements were made before and after the administration of repetitive doses of i.v. histamine.

Following the establishment of a consistent response to i.v. histamine, vagal nerve stimulation was attempted at variations of 1 to 5 volts, 1 Hz, 2 mS to identity parameters that attenuate responses to i.v. histamine. Bronchoconstriction in response to i.v. histamine is known to be due to both direct airway smooth muscle effects and due to stimulation of vagal nerves to release acetylcholine.

At the end of vagal nerve challenges atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

In order to measure the bronchoconstriction, the airway pressure was measured in two places. The blood pressure and heart rate were measured to track the subjects' vital signs.

In all the following graphs, the top line BP (red) shows blood pressure, second line AP1 shows airway pressure, third line AP2 shows airway pressure on another sensor, the last line HR is the heart rate derived from the pulses in the blood pressure.

Figure 19:
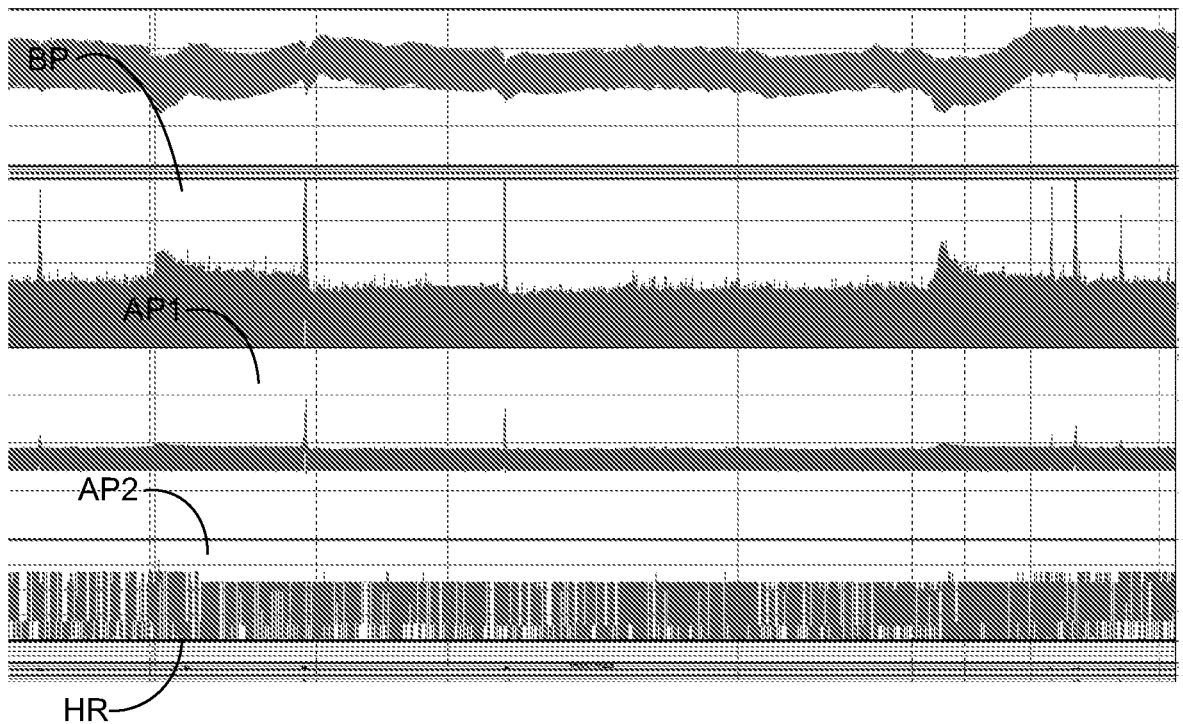
FIGS. 19-24 graphically illustrate the inability of signals taught by U.S. patent application Ser. No. 10/990,938 to achieve the results of the present invention.

FIG. 19 graphically illustrates exemplary experimental data from a first experiment on another guinea pig. The graph shows the effects of Tracey's 1V, 1 Hz, 2 mS waveform applied to both vagus nerves on the guinea pig. The first peak in airway pressure is from histamine alone, after which Tracey's signal was applied for 10 minutes as proposed in Tracey's patent application. As seen from the second airway peak, the signal has no noticeable effect on airway pressure. The animal's vital signs actually stabilized, seen in the rise in blood pressure, after the signal was turned off.

Figure 20:
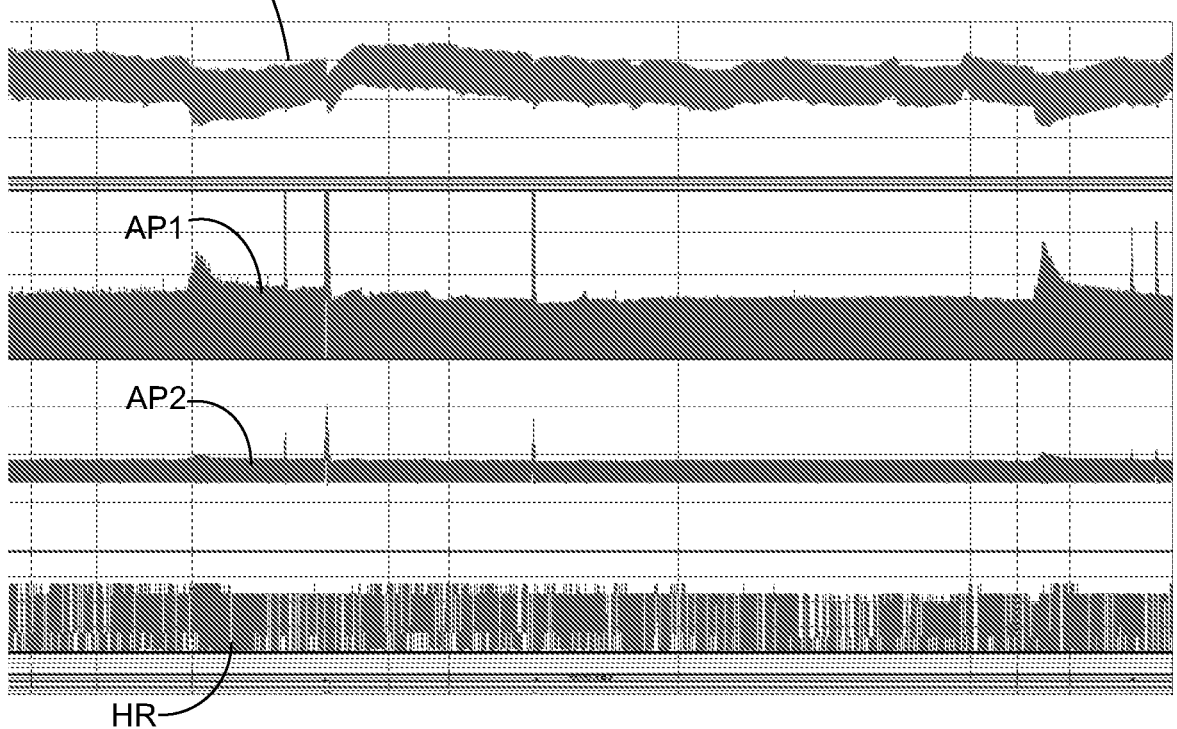

FIG. 20 graphically illustrates exemplary experimental data from a second experiment on the guinea pig in FIG. 19. The graph shows the effects of Tracey's 1V, 1 Hz, 2 mS waveform with the polarity reversed (Tracey did not specify polarity in the patent application) applied to both vagus nerves on the guinea pig. Again, the signal has no beneficial effect on airway pressure. In fact, the second airway peak from the signal and histamine combination is actually higher than the first peak of histamine alone.

Figure 21:
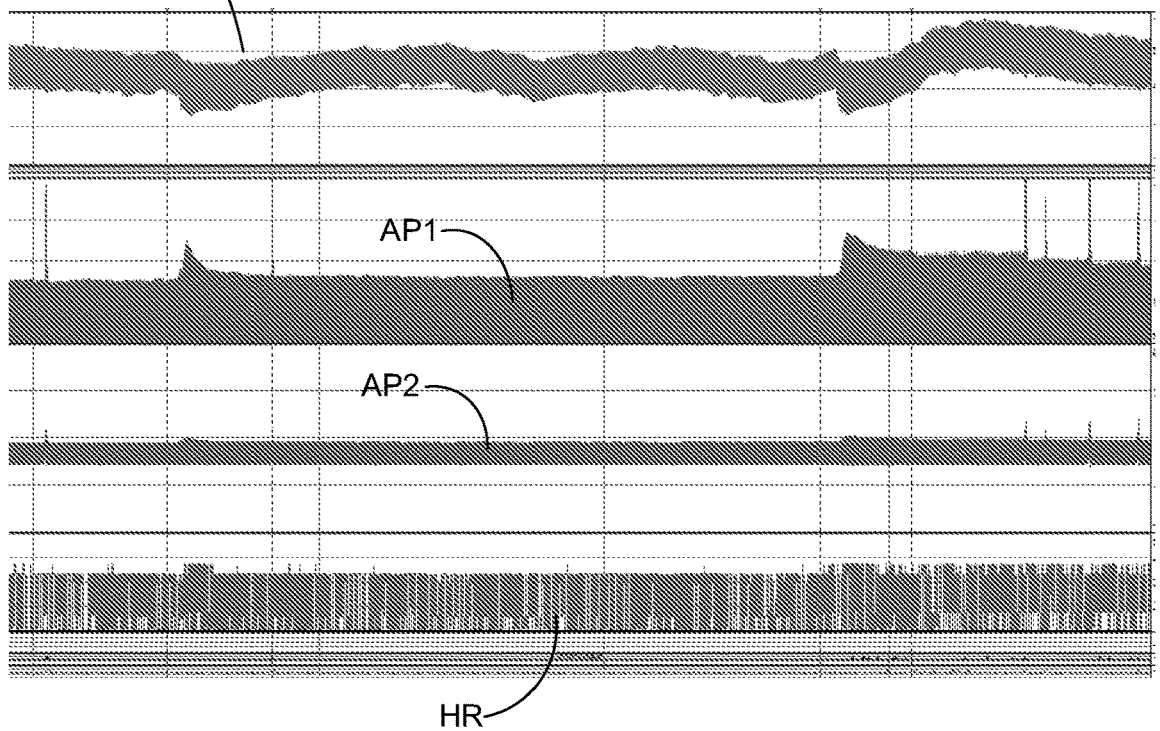

FIG. 21 graphically illustrates exemplary experimental data from a third experiment on the guinea pig in FIG. 19. The graph shows the effects of Tracey's 1V, 1 Hz, 2 mS waveform applied to both vagus nerves on the guinea pig. Again, the signal has no beneficial effect on airway pressure. Instead, it increases airway pressure slightly throughout the duration of the signal application.

Figure 22:
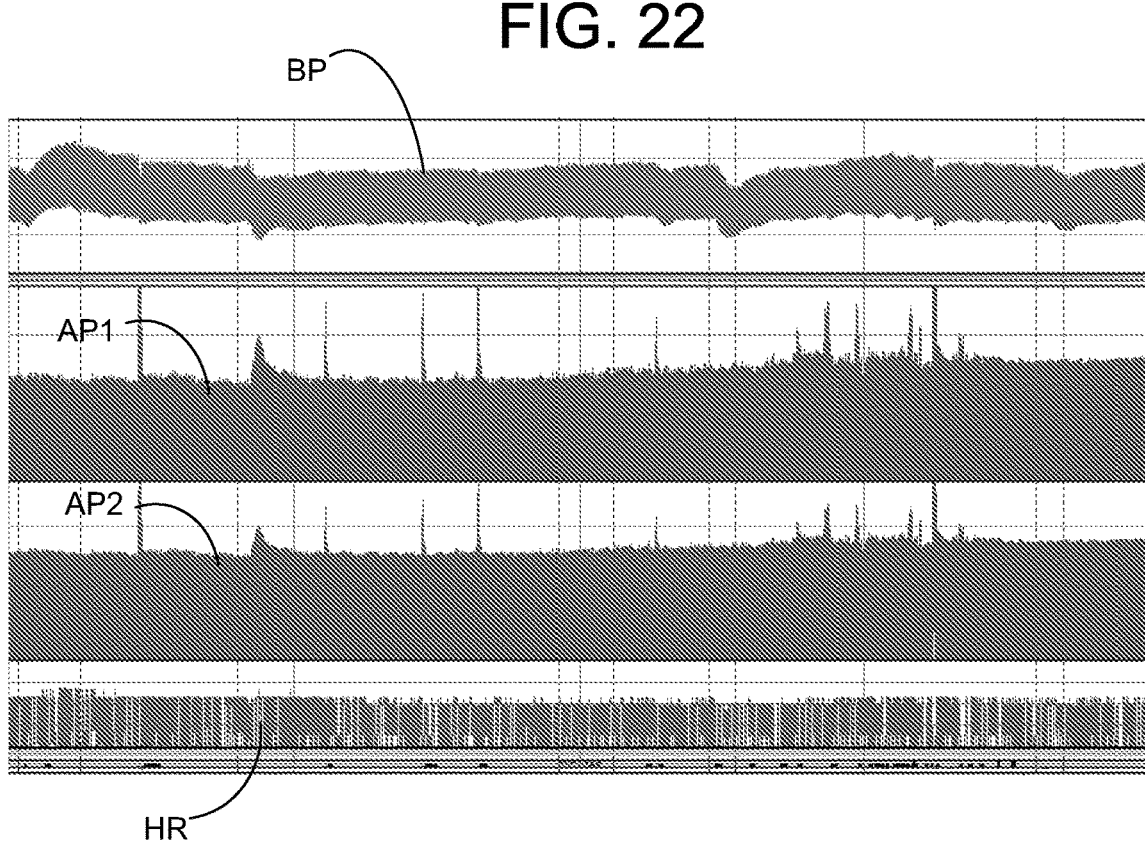

FIG. 22 graphically illustrates additional exemplary experimental data from an experiment on a subsequent guinea pig. The graph shows, from left to right, application of the 1.2V, 25 Hz, 0.2 mS signal disclosed in the present application, resulting in a slight decrease in airway pressure in the absence of additional histamine. The subsequent three electrical stimulation treatments are 1V, 5V, and 2.5V variations of Tracey's proposed signal, applied after the effects of a histamine application largely had subsided. It is clear that the Tracey signals do not cause a decrease in airway pressure, but rather a slight increase, which remained and progressed over time.

Figure 23:
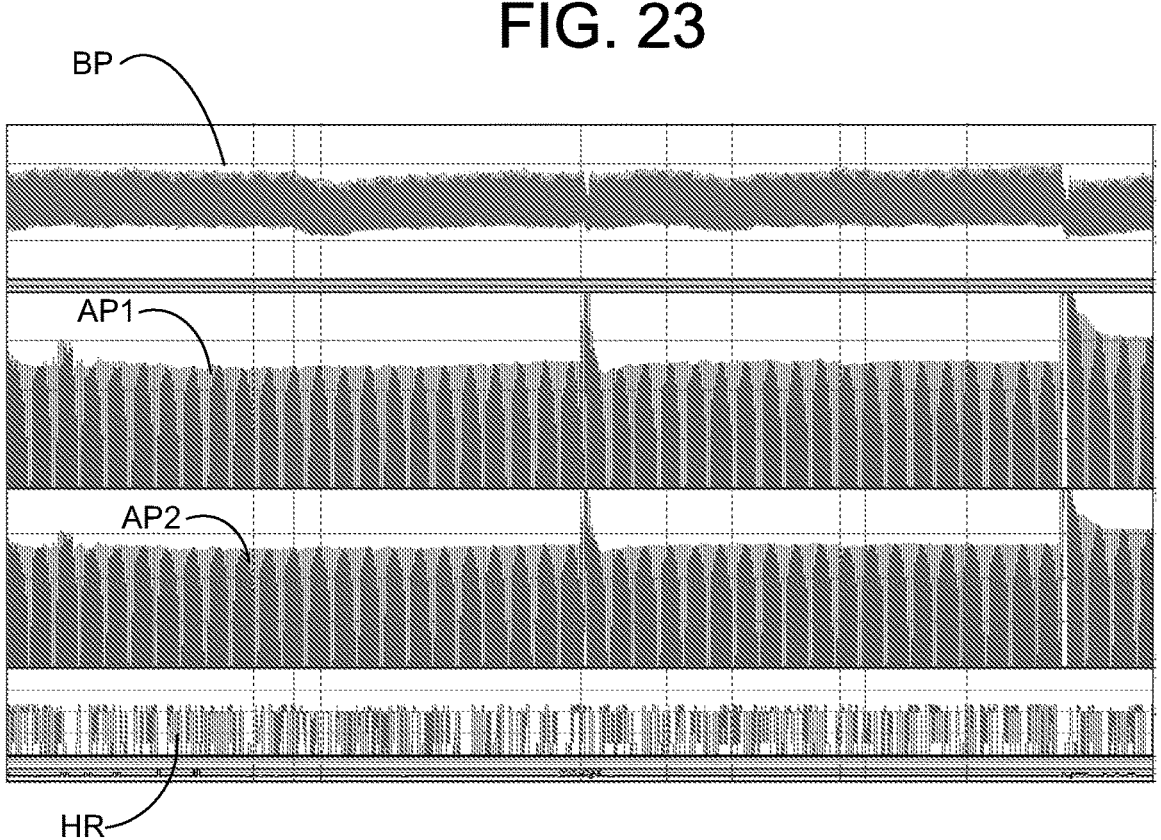

FIG. 23 graphically illustrates further exemplary experimental data from additional experiments using signals within the range of Tracey's proposed examples. None of the signals proposed by Tracey had any beneficial effect on airway pressure. Factoring in a potential range of signals, one experiment used 0.75V, which is below Tracey's proposed range, but there was still no beneficial effect on airway pressure.

Figure 24:
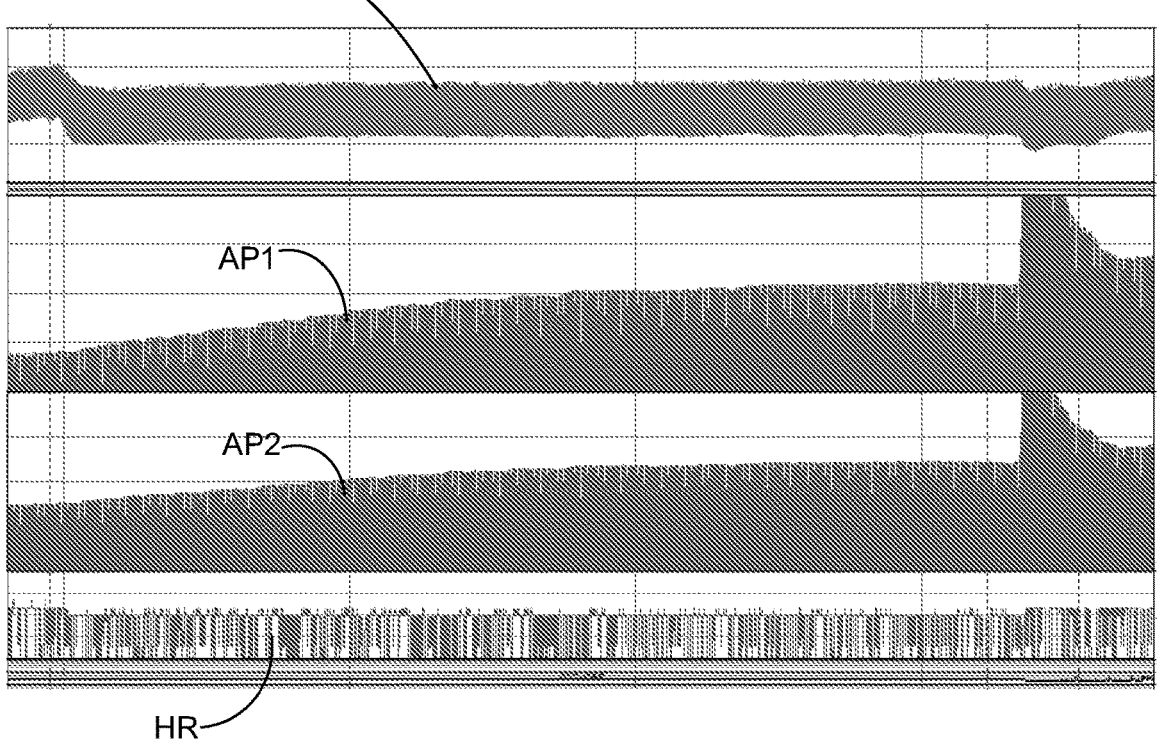

FIG. 24 graphically illustrates exemplary experimental data from subsequent experiments showing the effect of Tracey's 5V, 1 Hz, 2 mS signal, first without and then with additional histamine. It is clear that the airway pressure increase is even greater with the signal, as the airway pressure progressively increased during the course of signal application. Adding the histamine after prolonged application of the Tracey signal resulted in an even greater increase in airway pressure.

The full range of the signal proposed by Tracey in his patent application was tested in the animal model of the present application. No reduction in airway pressure was seen. Most of the voltages resulted in detrimental increases in airway pressure and detrimental effects to vital signs, such as decreases in blood pressure.

In International Patent Application Publication Number WO 93/01862, filed Jul. 22 1992, Joachim Wernicke and Reese Terry (hereinafter referred to as "Wernicke") propose a method of treating respiratory disorders such as asthma, cystic fibrosis and apnea by applying electric signals to the patient's vagus nerve. However, Wernicke specifically teaches to apply a signal that blocks efferent activity in the vagus nerve to decrease the activity of the vagus nerve to treat asthma. Moreover, the example disclosed in Wernicke for the treatment of asthma is an electrical impulse having a frequency of 100 Hz, a pulse width of 0.5 ms, an output current of 1.5 mA and an OFF time of 10 seconds for every 500 seconds of ON time (see Table 1 on page 17 of Wernicke). The applicants of the present application performed additional testing to determine if Wernicke's proposed method has any beneficial effect on bronchodilation or blood pressure in the model that shows efficacy with the method used in the present application. The applicants of the present application sought to determine whether Wernicke's signal can be applied to the vagus nerve to attenuate histamine-induced bronchoconstriction and increase in blood pressure in guinea pigs.

Similar to the Tracey testing, male guinea pigs (400 g) were transported to the lab and immediately anesthetized with an i.p. injection of urethane 1.5 g/kg. Skin over the anterior neck was opened and the carotid artery and both jugular veins are cannulated with PE50 tubing to allow for blood pressure/heart rate monitoring and drug administration, respectively. The trachea was cannulated and the animal ventilated by positive pressure, constant volume ventilation followed by paralysis with succinylcholine (10 ug/kg/min) to paralyze the chest wall musculature to remove the contribution of chest wall rigidity from airway pressure measurements.

Guanethidine (10 mg/kg i.v.) was given to deplete norepinephrine from nerve terminals that may interfere with vagal nerve stimulation. Both vagus nerves were exposed and connected to electrodes to allow selective stimuli of these nerves. Following 15 minutes of stabilization, baseline hemodynamic and airway pressure measurements were made before and after the administration of repetitive doses of i.v. histamine.

Following the establishment of a consistent response to i.v. histamine, vagal nerve stimulation was attempted at variations of 100 Hz, 0.5 ms and 1.5 mA output current to identity parameters that attenuate responses to i.v. histamine. Bronchoconstriction in response to i.v. histamine is known to be due to both direct airway smooth muscle effects and due to stimulation of vagal nerves to release acetylcholine.

At the end of vagal nerve challenges atropine was administered i.v. before a subsequent dose of histamine to determine what percentage of the histamine-induced bronchoconstriction was vagal nerve induced. This was considered a 100% response. Success of electrical interruption in vagal nerve activity in attenuating histamine-induced bronchoconstriction was compared to this maximum effect. Euthanasia was accomplished with intravenous potassium chloride.

In order to measure the bronchoconstriction, the airway pressure was measured in two places. The blood pressure and heart rate were measured to track the subjects' vital signs. In all the following graphs, the top line BP (red) shows blood pressure, second line AP1 shows airway pressure, third line AP2 shows airway pressure on another sensor, the last line HR is the heart rate derived from the pulses in the blood pressure.

Figure 25:
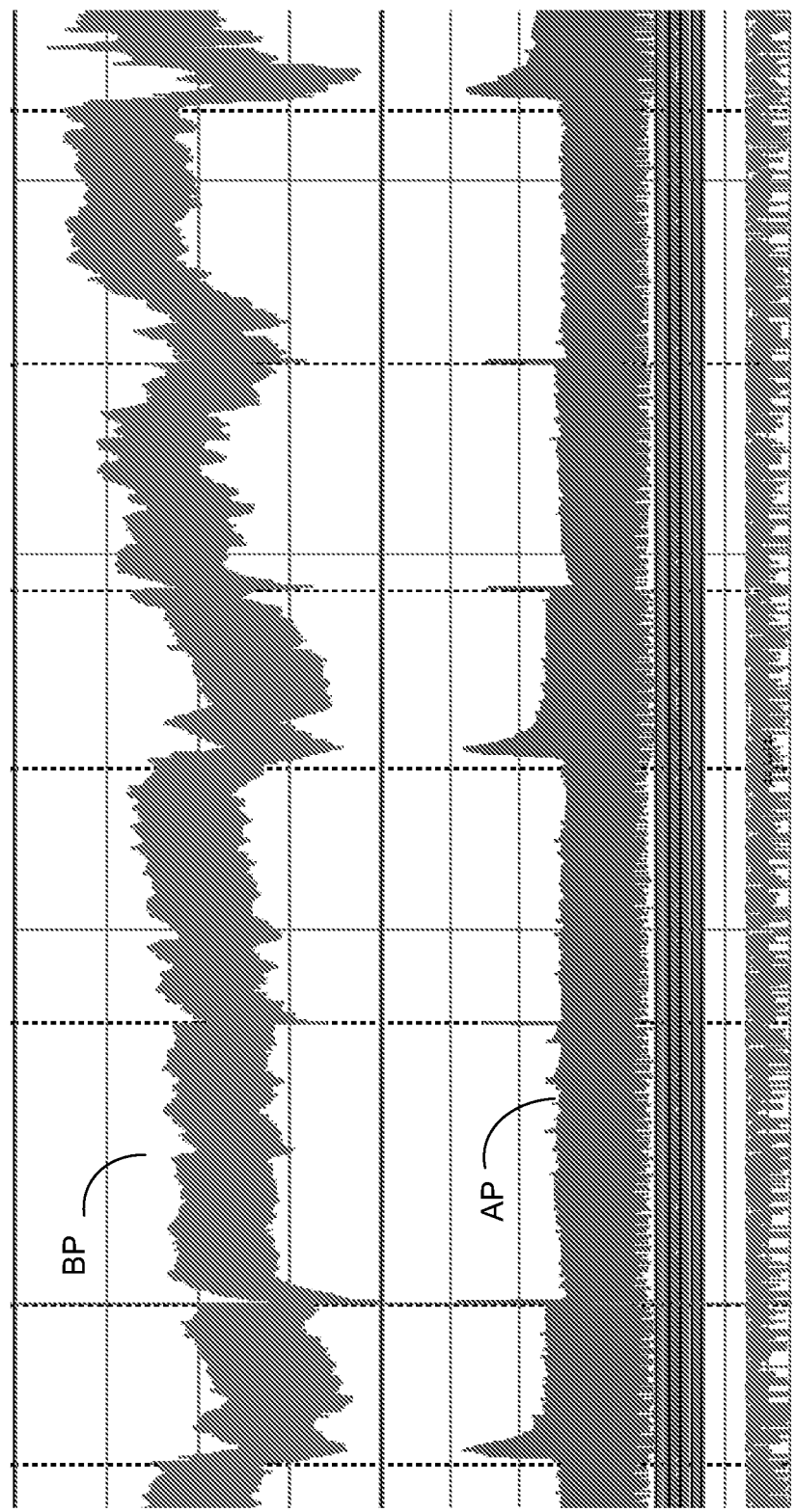
FIGS. 25 and 26 graphically illustrates the inability of signals taught by International Patent Application Publication Number WO 93/01862 to achieve the results of the present invention.
Figure 26:
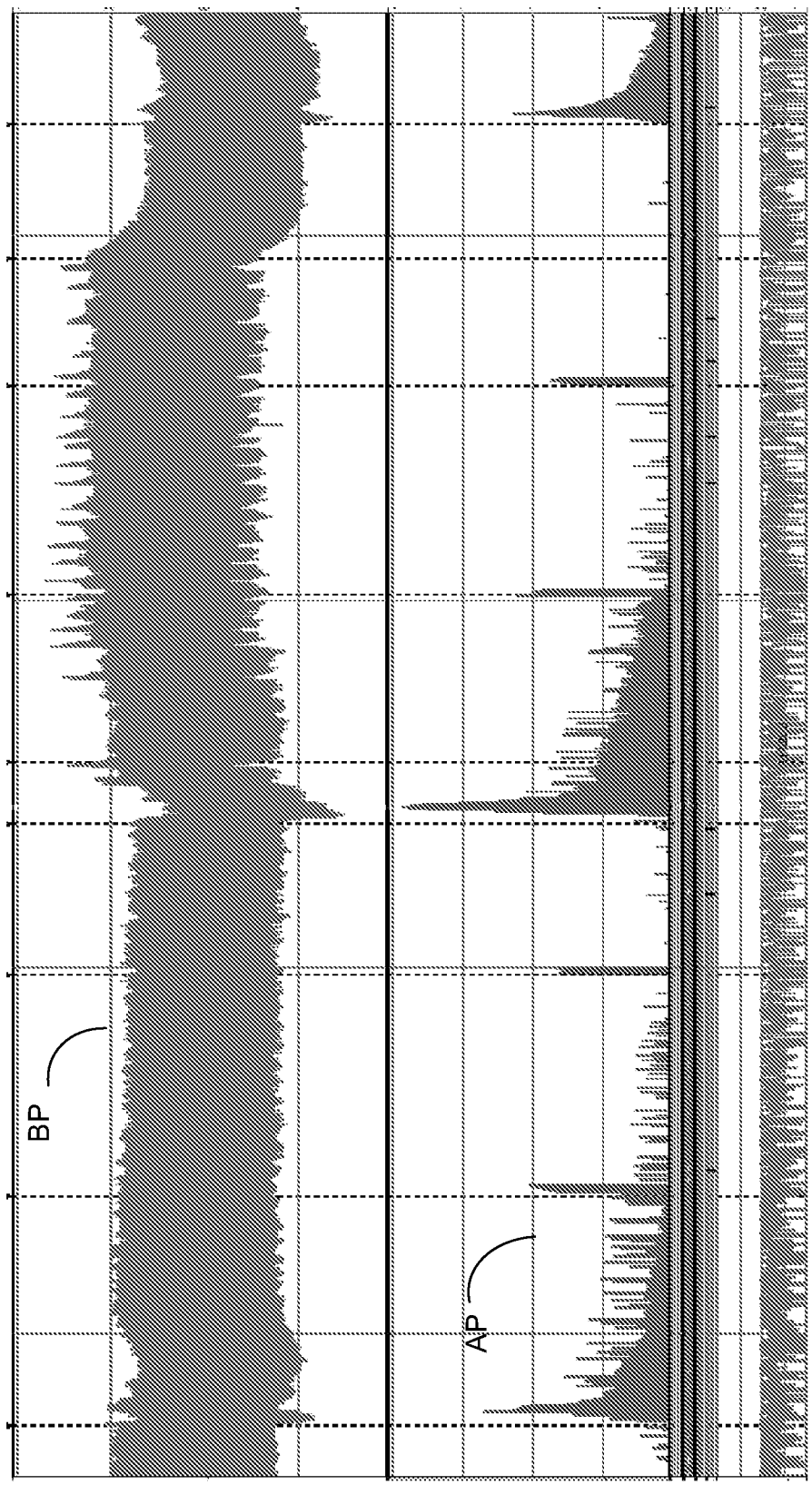

FIGS. 25 and 26 graphically illustrate exemplary experimental data from the experiment on another guinea pig. The graph shows the effects of Wernicke's 100 Hz, 1.5 mA, 0.5 mS waveform applied to both vagus nerves on the guinea pig. FIG. 25 illustrates two peaks in airway pressure (AP) from histamine alone with no treatment (the first two peaks) and a third peak at the right of the graph after which Wernicke's signal was applied at 1.2 mA. As shown, the results show no beneficial result on the histamine-induced airway pressure increase or the blood pressure at 1.2 mA. In FIG. 26, the first and third peaks in airway pressure (AP) are from histamine along with no treatment and the second peak illustrates airway pressure after Wernicke's signal was applied at 1.8 mA. As shown, the signal actually increased the histamine-induced airway pressure at 2.8 mA, making it clinically worse. Thus, it is clear the Wernicke signals do not cause a decrease in airway pressure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating a disease or disorder in a patient, the method comprising:
    positioning a surface of a housing in contact with an outer skin surface of the patient, wherein the housing is coupled to a power supply and the housing comprises a magnetic coil located within an interior of the housing; and
    applying a sufficient magnetic field via the power supply and the magnetic coil to generate an electrical impulse at or near a vagus nerve of the patient, wherein the electrical impulse is sufficient to modulate fibers of the vagus nerve and treat the disease or disorder.

2. The method of claim 1, wherein the electrical impulse is sufficient to stimulate a release of catecholamines within the patient.

3. The method of claim 1, wherein the electrical impulse is sufficient to stimulate a release of neurotransmitters within the patient.

4. The method of claim 2, wherein the catecholamines comprise endogenous B-agonists, epinephrine or norepinephrine.

5. The method of claim 1 further comprising positioning the surface of the housing in contact with the outer skin surface of a neck of the patient.

6. The method of claim 1, wherein the disease or disorder comprises bronchoconstriction and the electrical impulse is sufficient to cause a release of catecholamines into a circulation of the patient at concentrations sufficient to product bronchial smooth muscle relaxation.

7. The method of claim 1, wherein the magnetic coil comprises a toroid.

8. The method of claim 1, wherein the electrical impulse comprises a frequency from about 15 Hz to about 50 Hz.

9. The method of claim 1, wherein the electrical impulse comprises a pulse width from about 10 to about 1,000 microseconds.

10. The method of claim 1, wherein the housing comprises a volume of electrically conductive fluid within the interior of the housing, wherein the energy transmitter is at least partially surrounded by and in contact with a portion of the electrically conductive fluid.

11. The method of claim 10, wherein the electrically conductive fluid comprises an electrically conductive gel.

12. A device for treating a disease or disorder in a patient, the device comprising:
    a power source;
    a housing coupled to the power source and having an interior, and an outer contact surface for contacting an outer skin surface of the patient;
    a magnetic coil positioned within the interior of the housing; and
    wherein the power source supplies energy to the magnetic coil to generate an electrical impulse at a vagus nerve of the patient when the outer contact surface of the housing is in contact with the outer skin surface of the patient, wherein the electrical impulse is sufficient to modulate fibers of the vagus nerve to treat the disease or disorder, wherein the magnetic coil comprises a toroid.

13. The device of claim 12, wherein the electrical impulse is sufficient to stimulate a release of catecholamines within the patient.

14. The device of claim 12, wherein the electrical impulse is sufficient to stimulate a release of neurotransmitters within the patient.

15. The device of claim 13, wherein the catecholamines comprise endogenous B-agonists, epinephrine or norepinephrine.

16. The device of claim 12 wherein the disease or disorder comprises bronchoconstriction and the electrical impulse is sufficient to cause a release of catecholamines into a circulation of the patient at concentrations sufficient to product bronchial smooth muscle relaxation.

17. The device of claim 12, wherein the power source is located within the interior of the housing.

18. The device of claim 12, wherein the interior of the housing is at least partially filled with an electrically conductive fluid that is in contact with, and at least partially surrounds, the energy transmitter.

19. The device of claim 12, wherein the electrical impulse comprises a frequency from about 15 Hz to about 50 Hz.

20. The device of claim 12, wherein the electrical impulse comprises a pulse width from about 10 to about 1,000 microseconds.

* * * * *